(12) United States Patent
Böhm et al.

(10) Patent No.: US 6,455,671 B1
(45) Date of Patent: Sep. 24, 2002

(54) THROMBIN INHIBITORS, THE PREPARATION AND USE THEREOF

(75) Inventors: Hans-Joachim Böhm, Limburgerhof; Stefan Koser; Helmut Mack, both of Ludwigshafen; Thomas Pfeiffer, Böhl-Iggelheim; Werner Seitz, Plankstadt; Hans Wolfgang Höffken, Ludwigshafen; Wilfried Hornberger, Neustadt, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 08/682,604

(22) PCT Filed: Jun. 6, 1995

(86) PCT No.: PCT/EP95/02135

§ 371 (c)(1),
(2), (4) Date: Dec. 16, 1996

(87) PCT Pub. No.: WO95/35309

PCT Pub. Date: Dec. 28, 1995

(30) Foreign Application Priority Data

Jun. 17, 1994 (DE) .......................................... 44 21 052

(51) Int. Cl.$^7$ ................................................. C07K 5/08
(52) U.S. Cl. ............................ 530/331; 514/18; 514/19
(58) Field of Search ...................... 514/18, 19; 530/331

(56) References Cited

U.S. PATENT DOCUMENTS

| 4,346,078 A | 8/1982 | Bajusz et al. ................ 424/177 |
| 4,703,036 A | 10/1987 | Bajusz et al. .................. 514/18 |
| 5,705,487 A | 1/1998 | Schacht et al. ................ 514/19 |
| 5,710,130 A | 1/1998 | Schacht et al. ................ 514/19 |
| 5,723,444 A | 3/1998 | Antonsson et al. ........... 514/19 |
| 5,726,159 A | 3/1998 | Schacht et al. ................ 514/19 |
| 5,744,487 A | 4/1998 | Ohshima et al. ............. 514/326 |
| 5,780,631 A | 7/1998 | Antonsson et al. ............. 546/1 |
| 5,783,563 A | 7/1998 | Antonsson et al. ........... 514/19 |
| 5,856,307 A * | 1/1999 | Autonsson .................... 514/18 |
| 5,939,392 A * | 8/1999 | Autonsson .................... 514/18 |

FOREIGN PATENT DOCUMENTS

| AU | 16086/92 | 11/1992 |
| DE | 31 08810 | 3/1981 |
| EP | 118 280 | 9/1984 |
| EP | 185 390 | 6/1985 |
| EP | 195 212 | 9/1986 |
| EP | 293 881 | 12/1988 |
| EP | 362 002 | 4/1990 |
| EP | 364 344 | 4/1990 |
| EP | 410 411 | 1/1991 |
| EP | 471 651 | 2/1992 |
| EP | 479 489 | 4/1992 |
| EP | 503 203 | 9/1992 |
| EP | 504 064 | 9/1992 |
| EP | 526 877 | 2/1993 |
| EP | 530 167 | 3/1993 |
| EP | 542 525 | 5/1993 |
| EP | 589 741 | 3/1994 |
| EP | 601 459 | 6/1994 |
| EP | 648 780 | 4/1995 |
| EP | 669 317 | 8/1995 |
| WO | 92/07868 | 5/1992 |
| WO | 93/11152 | 6/1993 |
| WO | 93/15756 | 8/1993 |
| WO | 93/18060 | 8/1993 |
| WO | 9/08941 | 4/1994 |
| WO | 94/29336 | 12/1994 |
| WO | 95/23609 | 9/1995 |

OTHER PUBLICATIONS

Symposia Biologica Hungarica, 25, 277, 1984.
Stürzebecher et al., *Pharmazie*, vol. 43, No. 11, Nov. 1988, pp. 782–783.
Voight et al., *Pharmazie*, vol. 43, No. 6, Jun. 1988, pp. 412–414.
Wagner et al., *Pharmazie*, vol. 39, No. 5, May 1984, pp. 315–317.
Voight et al., *Pharmazie*, vol. 39, No. 6 Jun. 1984, pp. 379–381.
Voight et al., *Pharmazie*, vol. 40, No. 8, Aug. 1985, pp. 527–529.
Stürzebecher et al., *Pharmazie*, vol. 42, No. 2, Feb. 1987, pp. 114–116.
Tsunematsu et al., *Chem. Abst.*, vol. 103, No. 11, Sep. 16, 1985, AN 84003j.
Mattson et al., *Folia Haematol.*, 1982, pp. 43–51.
Oleksyszyn et al., *J. Med. Chem.*, vol. 37, 1994, pp. 226–231.
Voight et al., *Pharmazie*, vol. 41, No. 6, 1986, pp. 378–381.

* cited by examiner

*Primary Examiner*—Christopher S. F. Low
*Assistant Examiner*—David Lukton
(74) *Attorney, Agent, or Firm*—Keil & Weinkauf

(57) ABSTRACT

Compounds of the formula

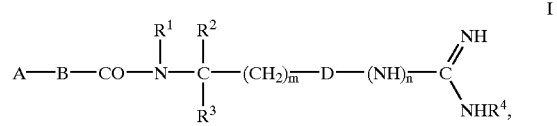

and the salts thereof with physiologically tolerated acids and the stereoisomers thereof, in which the substituents have the meanings stated in the description, are described. Also disclosed are intermediates for their preparation. The compounds are suitable for controlling diseases.

1 Claim, No Drawings

THROMBIN INHIBITORS, THE PREPARATION AND USE THEREOF

BACKGROUND OF THE INVENTION

Thrombin belongs to the group of serine proteases and plays a central part in the blood coagulation cascade as terminal enzyme. Both the intrinsic and the extrinsic coagulation cascade lead, via several amplifying stages, to the production of thrombin from prothrombin. The thrombin-catalyzed cleavage of fibrinogen to fibrin then initiates blood coagulation and platelet aggregation, which in their turn enhance thrombin formation by the binding of platelet factor 3 and coagulation factor XIII as well as a whole series of highly active mediators.

The formation and effect of thrombin are central events in the production both of white, arterial and of red, venous thrombi and therefore potentially effective points of attack for drugs. Thrombin inhibitors contrast with heparin in being able completely to inhibit, independently of cofactors, simultaneously the effects of thrombin both in the coagulation cascade and on platelets. They are able to prevent in the acute phase thromboembolic events after percutaneous transluminal coronary angioplasty (PTCA) and lysis and to serve as anticoagulants in extracorporeal circulation (heart-lung machine, hemodialysis). They can also be used generally for thrombosis prophylaxis, for example after surgical interventions.

It is known that synthetic arginine derivatives influence the enzymic activity of thrombin by interacting with the active serine residue of the protease. Peptides based on Phe-Pro-Arg in which the N-terminal amino acid is in the D form have proved to be particularly beneficial. D-Phe-Pro-Arg isopropyl ester has been described as a competitive thrombin inhibitor (C. Mattson et al., Folia Haematol. 109 (1982) 43–51).

Derivatization of the C-terminal arginine to the aldehyde leads to an enhancement of the inhibitory action. Thus, a large number of arginals able to bind the hydroxyl group of the "active" serine as hemiacetal have been described (EP 185,390, 479,489, 526,877, 542,525; WO 93 15 756, 93 18 060).

The thrombin inhibitory activity of peptide ketones, fluorinated alkyl ketones and of keto esters, boric acid derivatives, phosphoric esters and α-keto carboxamides can likewise be explained by this serine interaction (EP 118,280, 195,212, 362,002, 364,344, 410,411, 471,651, 589,741, 293,881, 503,203, 504,064, 530,167; WO 92 07 869; 94 08 941).

DE 31 08 810 and WO 93 11 152 describe ω-aminoalkylguanidine di-peptides.

The peptide 4-amidinophenylglycinephosphonate diphenyl esters described by J. Oleksyszyn et al. in J. Med. Chem. 37 (1994) 226–231 are irreversible thrombin inhibitors with inadequate selectivity for other serine proteases.

EP 601,459 and WO 94/29336, which are not prior publications, describe thrombin inhibitory peptides.

BRIEF SUMMARY OF THE INVENTION

The present invention relates to novel thrombin inhibitors, to the preparation thereof and to the use thereof for controlling diseases.

DETAILED DESCRIPTION OF THE INVENTION

The present invention relates to compounds of the formula

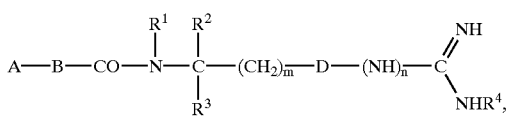

and the salts thereof with physiologically tolerated acids and the stereoisomers thereof, in which the substituents have the following meanings:

A:

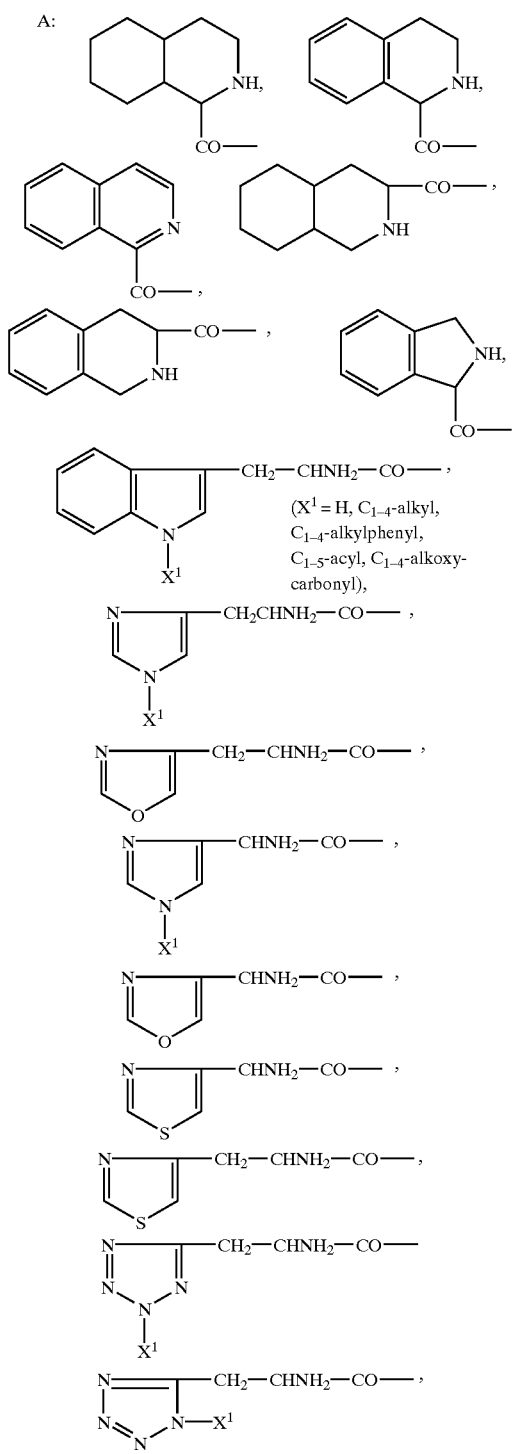

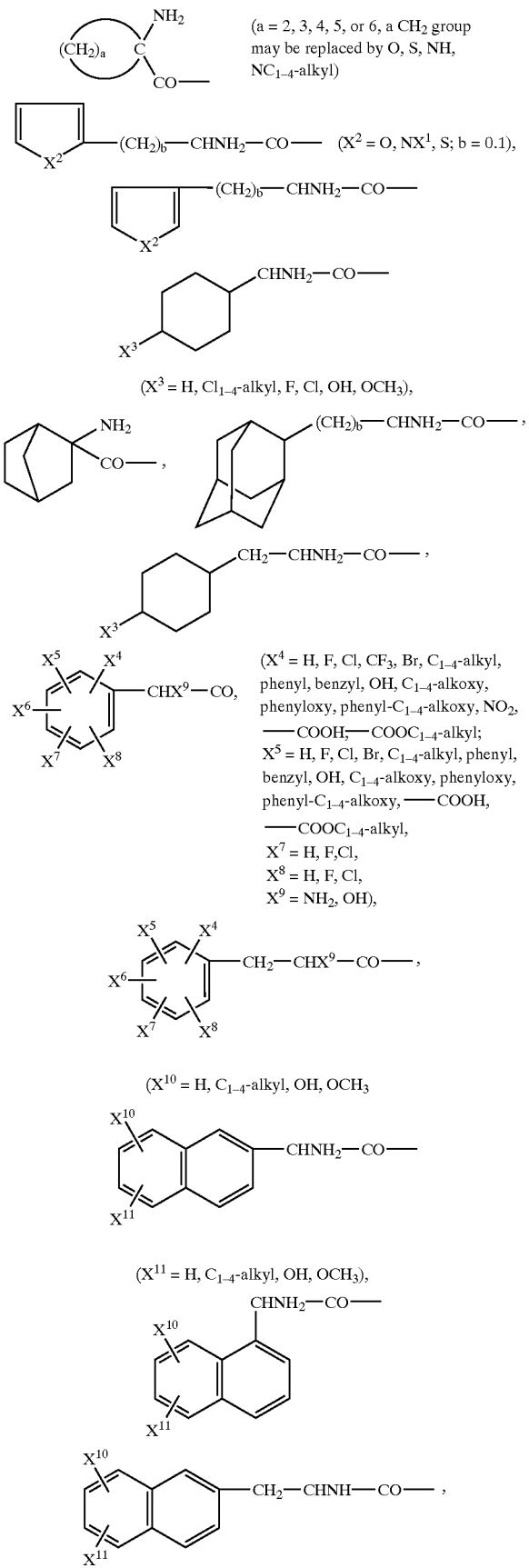
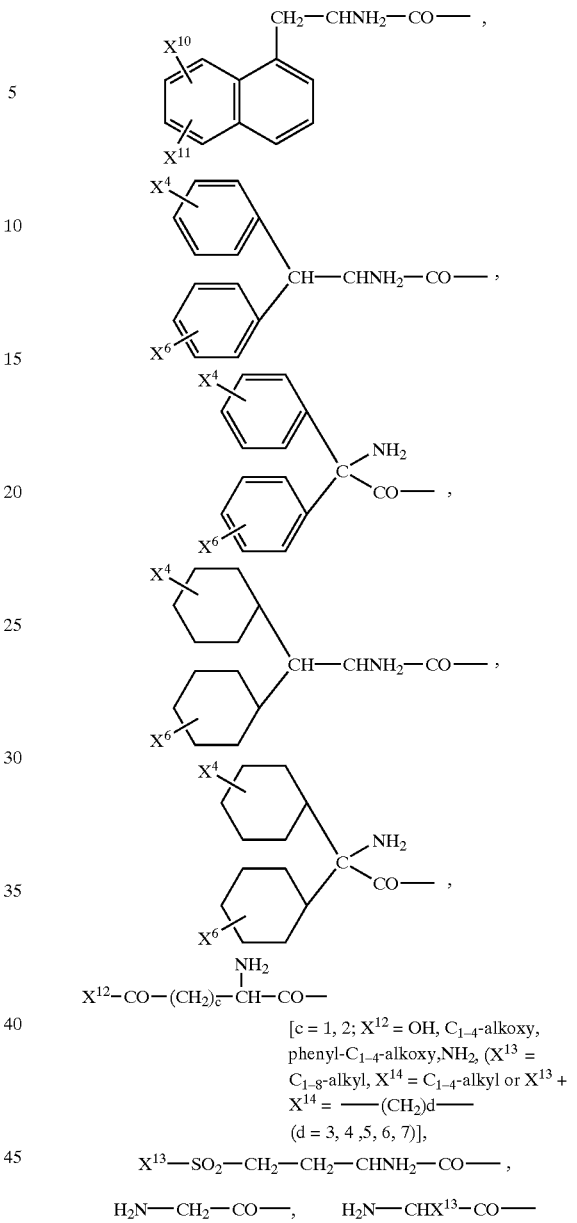

where in all the abovementioned A radicals the α-NH or α-NH$_2$ group can be mono- or disubstituted by $C_{1-12}$-alkyl, phenyl-$C_{1-4}$-alkylene, $X^{12}$OC—$C_{1-6}$-alkylene, $X^{12}$OC—$C_{1-6}$-alkylcarbonyl, -α- or β-naphthyl-$C_{1-4}$-alkylene, $C_{1-12}$-alkylcarbonyl, phenyl-$C_{1-4}$-alkylcarbonyl, $C_{1-7}$-alkoxycarbonyl, phenyl-$C_{1-5}$-alkoxycarbonyl, -α- or β-naphthyl-$C_{1-4}$-alkylcarbonyl-, $C_{1-6}$-alkylaminocarbonyl or phenyl-$C_{1-4}$-alkylaminocarbonyl also A: $X^1$—NH—CH$_2$—CH$_2$—CO—, $X^1$—NH—CH$_2$—CH$_2$—CH$_2$—CO—

$X^{15}$—(CH$_2$)$_f$—SO$_2$—(f=0,1,2,3,4, $X^{15}$=a phenyl or α- or β-naphthyl radical which is unsubstituted or substituted by 1–3 CH$_3$ and/or CH$_3$O groups, or one of the radicals

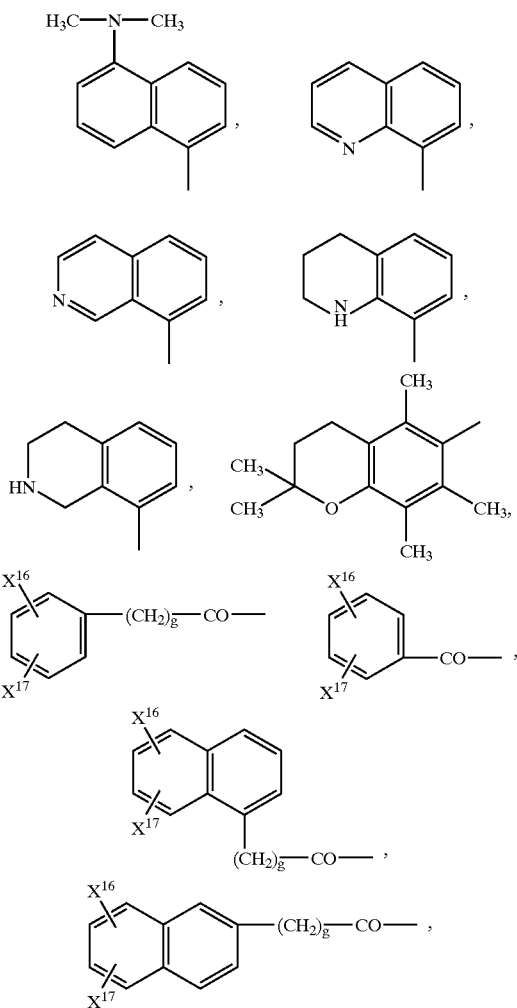

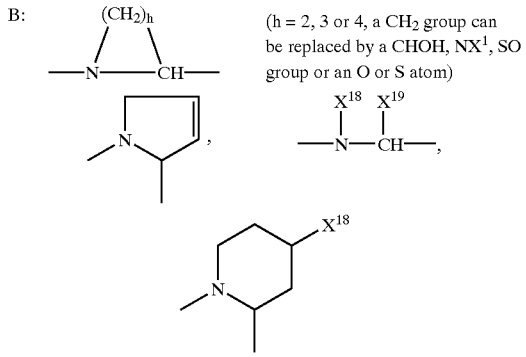

($X^{18}$=H or $C_{1-4}$-alkyl,
$X^{19}$=H, $C_{1-6}$-alkyl, phenyl, benzyl, cyclohexyl or cyclohexylmethyl)

$R^1$: H or $C_{1-4}$-alkyl $R^2$: H or $C_{1-4}$-alkyl $R^3$: H, $C_{1-8}$-alkyl, phenyl, phenyl-$C_{1-4}$-alkylene, $CH_2OH$, —CO—$X^{20}$, —CO—CO—$X^{20}$, ($X^{20}$=H, $C_{1-4}$-alkoxy, $C_{1-4}$-alkyl, phenyl, phenyl-$C_{1-4}$-alkylene, phenyl-$C_{1-4}$-alkoxy, $CF_3$, $C_2F_5$, an N-terminally linked natural amino acid, $CH_2OH$, —$CH_2$—O—$C_{1-4}$-alkyl, NH—($C_{1-4}$-alkylene)-phenyl or NH—$C_{1-6}$-alkyl), m: 0,1,2 or 3

D: phenylene on which $(CH_2)_m$ and $(NH)_n$ are linked in the para or meta position to one another and which can be substituted in the ortho position to $(CH_2)_m$ by F, Cl, Br, HO—$CH_2$—, OH, $NH_2$, $NO_2$, $C_{1-4}$-alkoxy, $C_{1-6}$-alkyl or $COX^{21}$ ($X^{21}$=H, $C_{1-4}$-alkyl, $C_{1-4}$-alkoxy, OH, $NH_2$, NH—$C_{1-4}$-alkyl) —O—$(CH_2)_{1-3}$—CO—$X^{21}$ or —$(CH_2)_{1-3}$—CO—$X^{21}$, pyridinylene, pyrimidinylene, pyrazinylene or pyridazinylene, on which $(CH_2)_m$ and $(NH)_n$ are linked in the para or meta position to one another and which can be substituted in the ortho position to $(CH_2)_m$ by F, Cl, Br, OH, $NH_2$, $C_{1-4}$-alkoxy or $C_{1-4}$-alkyl, 1,4- or 1,3-cyclohexylene, in which one $CH_2$ group in the ortho position to $(CH_2)_m$ can be replaced by NH, O, S or SO, or piperidinylene which is connected in the 3 or 4 position to the nitrogen to $(CH_2)_m$, and in which the nitrogen atom itself carries the C(=NH) $NHR^4$ group, n: 0 or 1

$R^4$: H, —CO—$C_{1-20}$-alkyl, —CO—O—$C_{1-20}$-alkyl, OH or $NH_2$.

The alkyl radicals present in the formula I may be straight-chain or branched.

Preferred compounds of the formula I are those where the substituents have the following meanings:

A:

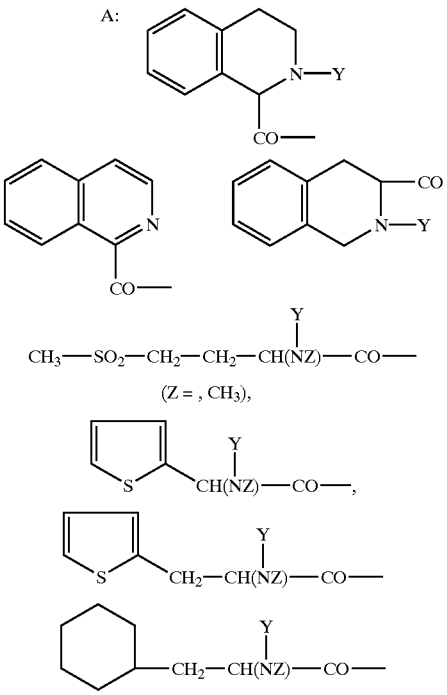

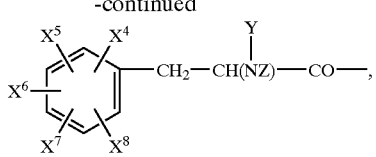

(Y = H, C$_{1-6}$-alkyl, phenyl-C$_{1-4}$-alkylene, a- or b-naphthyl——CH$_2$——, 3,4-dimethoxyphenyl——CH$_2$——, X$^{12}$—CO—C$_{1-4}$-alkylene, [X$^{12}$ = OH, C$_{1-4}$-alkoxy, NH$_2$, C$_{1-4}$-alkyl—NH—, phenyl-C$_{1-4}$-alkylene—NH—, NX$^{13}$X$^{14}$(X$^{13}$ = C$_{1-6}$-alkyl, X$^{14}$ = C$_{1-4}$-alkyl or X$^{13}$ + X$^{14}$ = (CH$_2$)$_d$——(d = 4,5,6))], X$_{12}$—CO—C$_{1-4}$-alkylene- (X$^4$=H, F, Cl, Br, CF$_3$, C$_{1-4}$-alkyl, OH, OCH$_3$, NO$_2$, phenyl, preferably H, F, Cl, Br, CH$_3$, t-butyl, OH, OCH$_3$, NO$_2$, X$^5$=H, F, Cl, Br, CH$_3$, OH, OCH$_3$, phenyl, preferably H, F, OH, OCH$_3$, phenyl, X$^6$=H, F, Cl, Br, CH$_3$, OH, OCH$_3$, preferably H, F, OH, OCH$_3$, X$^7$=H, F, X$^8$=H, F),

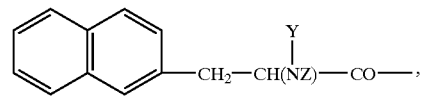
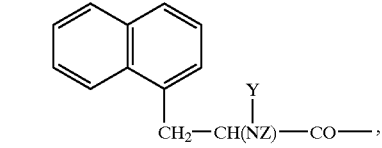
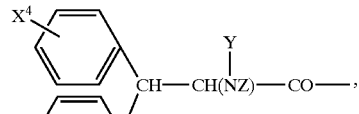
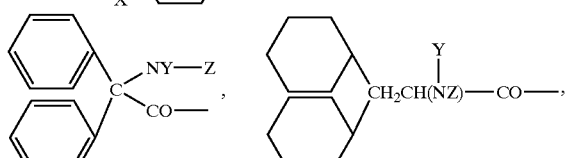
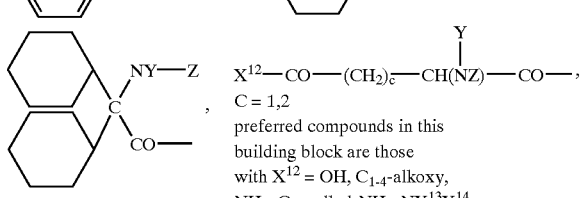
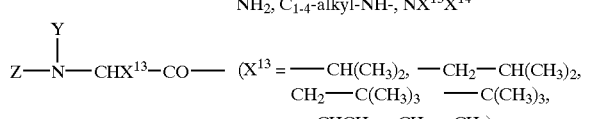
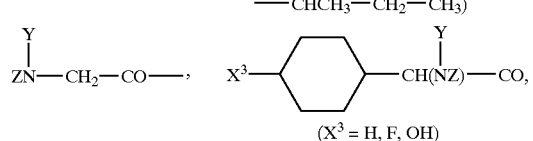

(X$^3$ = H, F, OH)

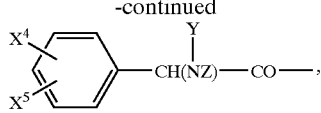
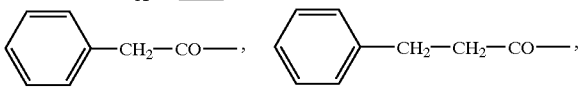
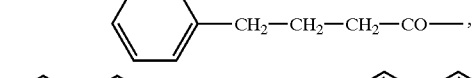
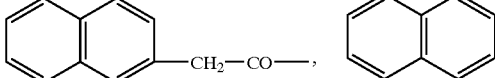
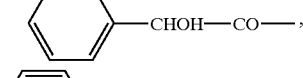
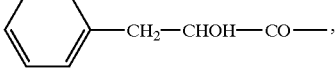
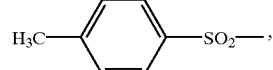
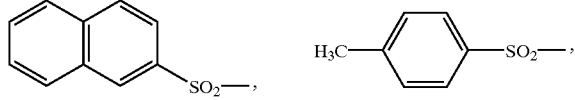
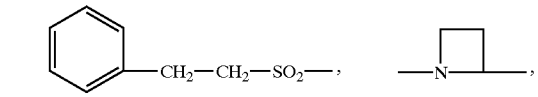
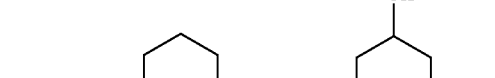
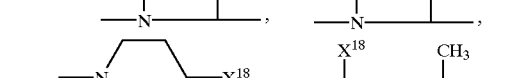
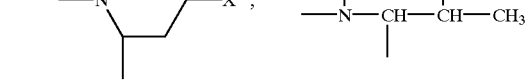

X$^{18}$ = H, CH$_3$

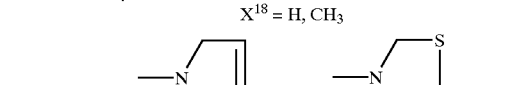

R$^1$: H, CH$_3$
R$^2$: H
R$^3$: H, CH$_3$, CHO, COCF$_3$, COC$_2$F$_5$, CO—CH$_2$OH, CO—CH$_3$, CO—CH$_2$-phenyl, CH$_2$OH,
R$^4$: H, OH, NH$_2$
m: 0, 1 a preferred group of D building blocks is

preferred building blocks of the combination —(CH$_2$)$_m$-D-(NH)$_n$— in the general formula I are:

for ──(CH$_2$)$_{\overline{m}}$──D──(NH)$_{\overline{n}}$── with m = 0, n = 0

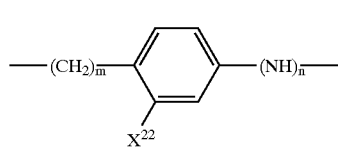

$X^{22}$ =
H, F, Cl, Br, CH$_2$──OH,
OH, NH$_2$, NO$_2$, C$_{1-4}$-alkoxy, C$_{1-6}$-alkyl,
$X^{21}$──CO──, ($X^{21}$ = OH, NH$_2$, C$_{1-4}$-alkyl-NH──, C$_{1-4}$-alkoxy),
$X^{21}$──CO──C$_{1-3}$-alkoxy, for ──(CH$_2$)$_{\overline{m}}$──D──(NH)$_{\overline{n}}$── with m = 0,1, n = 0, 1

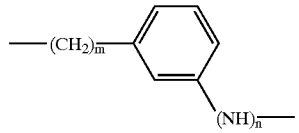

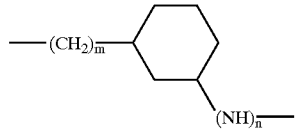

for ──(CH$_2$)$_{\overline{m}}$──D──(NH)$_{\overline{n}}$── with m = 0, n = 0, 1

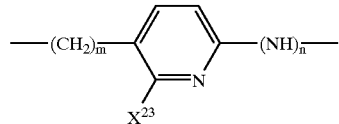

$X^{23}$ = H, F, Cl, OH, NH$_2$, C$_{1-4}$-alkoxy, C$_{1-6}$-alkyl

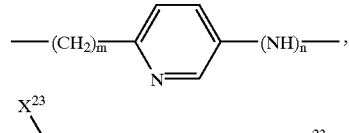

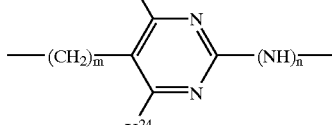

where $X^{23}$ and $X^{24}$ are independent of one another and are each H, F, Cl, OH, NH$_2$, C$_{1-4}$-alkoxy, C$_{1-6}$-alkyl,

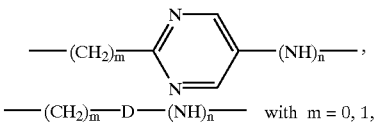

for ──(CH$_2$)$_{\overline{m}}$──D──(NH)$_{\overline{n}}$── with m = 0, 1, n = 0

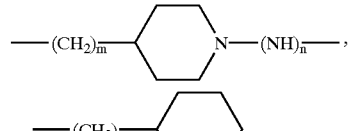

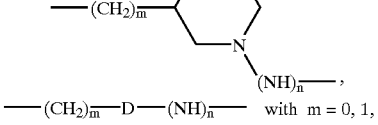

for ──(CH$_2$)$_{\overline{m}}$──D──(NH)$_{\overline{n}}$── with m = 0, 1, n = 0

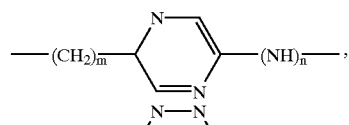

Particularly preferred compounds of the formula I are those in which the substituents have the following meanings:

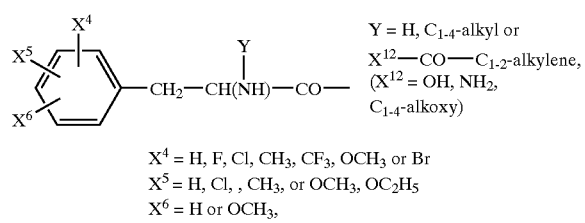

Y = H, C$_{1-4}$-alkyl or
$X^{12}$──CO──C$_{1-2}$-alkylene,
($X^{12}$ = OH, NH$_2$, C$_{1-4}$-alkoxy)

$X^4$ = H, F, Cl, CH$_3$, CF$_3$, OCH$_3$ or Br
$X^5$ = H, Cl, , CH$_3$, or OCH$_3$, OC$_2$H$_5$
$X^6$ = H or OCH$_3$,

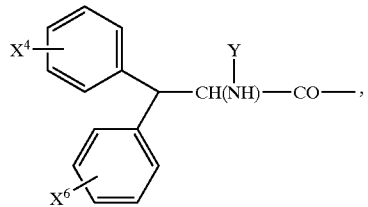

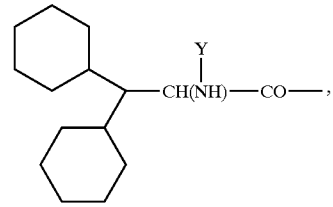

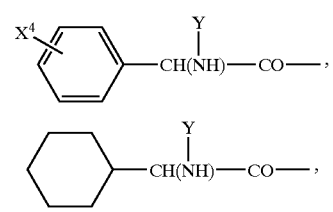

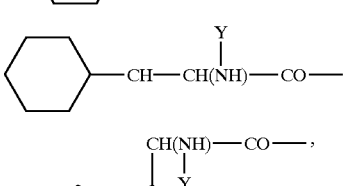

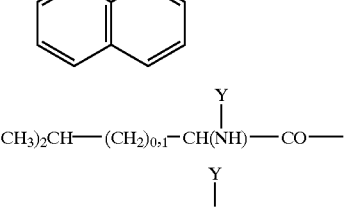

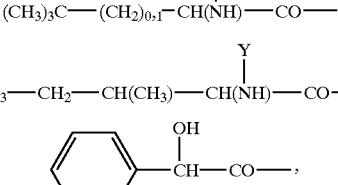

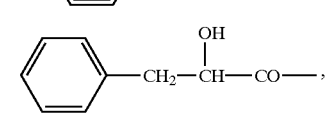

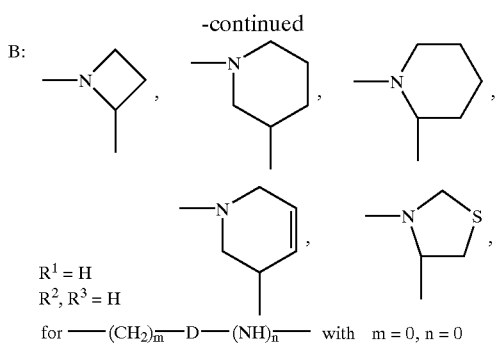
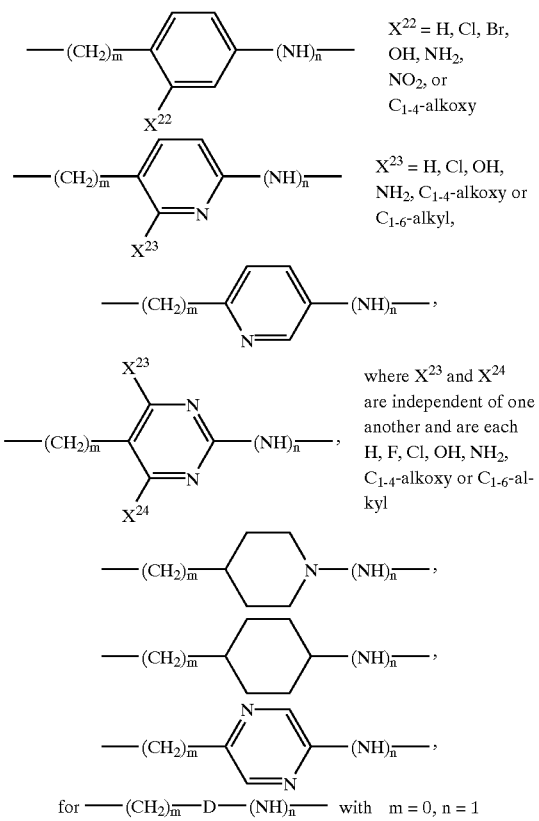

Among the particularly preferred compounds, the following combinations should be emphasized, where A and B have the meanings described as particularly preferred:

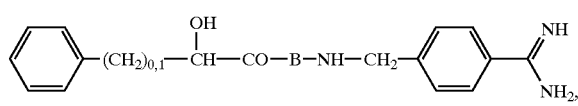

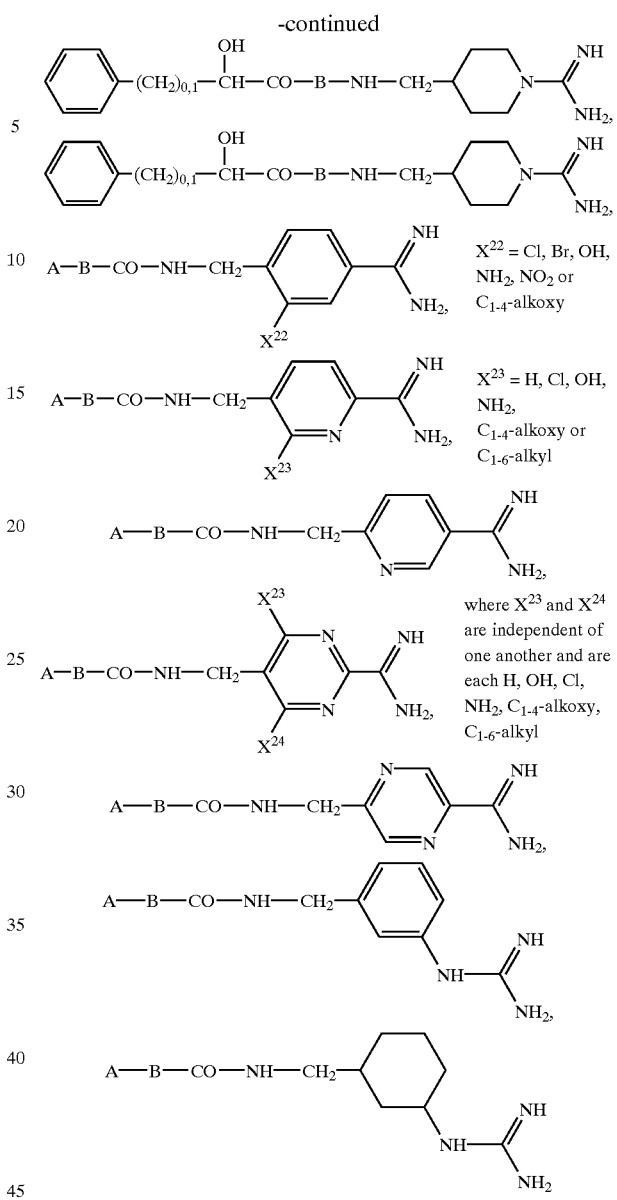

The following substances are mentioned by way of example:

1. Boc-(D)-Phe-Pro-NH-(4-Am)-2-phenethyl
2. H-(D)-Phe-Pro-NH-(4-Am)-2-phenethyl
3. Boc-Phe-Pro-NH-pAmb
4. H-Phe-Pro-NH-pAmb
5. Boc-(D)-Phe-Pro-NH-pAmb
6. Ac-(D)-Phe-Pro-NH-pAmb
7. H-(D)-Phe-Pro-NH-pAmb
8. H-(D)-Phe-Pro-N(Me)-pAmb
9. Me-(D)-Phe-Pro-NH-pAmb
10. Z-Me-(D)-Phe-Pro-NH-pAmb
11. HOOC—CH$_2$-(D)-Phe-Pro-NH-pAmb
12. MeOOC—CH$_2$-(D)-Phe-Pro-NH-pAmb
13. t-BuOOC—CH$_2$-(Boc)-(D)-Phe-Pro-NH-pAmb
14. EtOOC-(D)-Phe-Pro-NH-pAmb
15. Boc-(D)-Phe-Pro-NH-mAmb
16. H-(D)-Phe-Pro-NH-mAmb
17. Z-(D)-Phe-Pro-(D,L)(4-Am)-PhgOH
18. Z-(D)-Phe-Pro-(D,L)(4-Am)-PhgOMe 19. H-(D)-Phe-Pro-(D,L)(4-Am)-Phg—OH
20. Boc-(D)-Phe-Pro-(4-Am)-PhgCH₂Ph
21. H-(D)-Phe-Pro-(4-Am)-PhgCH₂Ph
22. H-(D)-Phe-Pro-NH-pAm-[(D,L)-α-Me]-benzyl
23. Me-(D)-Phe-Pro-(D or L)(4-Am)-Phgψ[CH₂—OH]/a
24. Me-(D)-Phe-Pro-(D or L)(4-Am)-Phgψ[CH₂—OH]/b
25. Boc-(D)-Phe-(4-F)-Pro-NH-pAmb
26. H-(D)-Phe(4-F)-Pro-NH-pAmb
27. Boc-(D)-Phe(4-Cl)-Pro-NH-pAmb
28. H-(D)-Phe(4-Cl)-Pro-NH-pAmb
29. Boc-(D,L)-Phe(4-Br)-Pro-NH-pAmb
30. H-(D,L)-Phe(4-Br)-Pro-NH-pAmb
31. H-(D)-Phe(4-OH)-Pro-NH-pAmb
32. Boc-(D)-Phe(4-MeO)-Pro-NH-pAmb
33. H-(D)-Phe(4-MeO)-Pro-NH-pAmb
34. Boc-(D,L)-Phe(4-EtO)-Pro-NH-pAmb
35. H-(D,L)-Phe(4-EtO)-Pro-NH-pAmb
36. Boc-(D)-Phe(4-BzlO)-Pro-NH-pAmb
37. H-(D)-Phe(4-BzlO)-Pro-NH-pAmb
38. Boc-(D,L)-Phe(4-Et)-Pro-NH-pAmb
39. H-(D,L)-Phe(4-Et)-Pro-NH-pAmb
40. Boc-(D,L)-Phe(4-iPr)-Pro-NH-pAmb
41. H-(D,L)-Phe(4-iPr)-Pro-NH-pAmb
42. Z-(D)-Phe(4-tBuO)-Pro-NH-pAmb
43. H-(D)-Phe(4-tBuO)-Pro-NH-pAmb
44. Boc-(D,L)-Phe(4-tBu)-Pro-NH-pAmb
45. H-(D,L)-Phe(4-tBu)-Pro-NH-pAmb
46. H-(D,L)-Phe(4-Ph)-Pro-NH-pAmb
47. Boc-(D,L)-Phe(4-n-Bu)-Pro-NH-pAmb
48. H-(D,L)-Phe(4-n-Bu)-Pro-NH-pAmb
49. Boc-(D)-Phe(4-COOMe)-Pro-NH-pAmb
50. H-(D)-Phe(4-COOMe)-Pro-NH-pAmb
51. H-(D)-Phe(4-NO₂)-Pro-NH-pAmb
52. Boc-(D,L)-Phe(3-F)-Pro-NH-pAmb
53. H-(D,L)-Phe(3-F)-Pro-NH-pAmb
54. Boc-(D,L)-Phe(3-Cl)-Pro-NH-pAmb
55. H-(D,L)-Phe(3-Cl)-Pro-NH-pAmb
56. H-(D,L)-Phe(3-OH)-Pro-NH-pAmb
57. Boc-(D,L)-Phe(3-MeO)-Pro-NH-pAmb
58. H-(D,L)-Phe(3-MeO)-Pro-NH-pAmb
59. Boc-(D,L)-Phe(3-PhO)-Pro-NH-pAmb
60. H-(D,L)-Phe(3-PhO)-Pro-NH-pAmb
61. Boc-(D,L)-Phe(3-Me)-Pro-NH-pAmb
62. H-(D,L)-Phe(3-Me)-Pro-NH-pAmb
63. H-(D,L)-Phe(3-Ph)-Pro-NE-pAmb
64. Boc-(D,L)-Phe(3-CF₃)-Pro-NH-pAmb
65. H-(D,L)-Phe(3-CF₃)-Pro-NH-pAmb
66. Boc-(D,L)-Phe(2-F)-Pro-NH-pAmb
67. H-(D,L)-Phe(2-F)-Pro-NH-pAmb
68. Boc-(D,L)-Phe(2-Cl)-Pro-NH-pAmb
69. H-(D,L)-Phe(2-Cl)-Pro-NH-pAmb
70. Boc-(D,L)-Phe(2-OH)-Pro-NH-pAmb
71. H-(D,L)-Phe(2-OH)-Pro-NH-pAmb
72. Boc-(D,L)-Phe(2-Meo)-Pro-NH-pAmb
73. H-(D,L)-Phe(2-MeO)-Pro-NH-pAmb
74. Boc-(D,L)-Phe(2-Me)-Pro-NH-pAmb
75. H-(D,L)-Phe(2-Me)-Pro-NH-pAmb
76. Boc-(D,L)-Phe(2-iPr)-Pro-NH-pAmb
77. H-(D,L)-Phe(2-iPr)-Pro-NH-pAmb
78. Boc-(D,L)-Phe(2-Ph)-Pro-NH-pAmb
79. H-(D,L)-Phe(2-Ph)-Pro-NH-pAmb
80. Boc-(D,L)-Phe(3,4-(F)₂)-Pro-NH-pAmb
81. H-(D,L)-Phe(3,4-(F)₂)-Pro-NH-pAmb
82. Boc-(D,L)-Phe(3,4-(Cl)₂)-Pro-NH-pAmb
83. H-(D,L)-Phe(3,4-(Cl)₂)-Pro-NH-pAmb
84. Boc-(D,L)-Phe(3-Cl-4-MeO)-Pro-NH-pAmb
85. H-(D,L)-Phe(3-Cl-4-MeO)-Pro-NH-pAmb
86. Boc-(D,L)-Phe(3-Cl-4-EtO)-Pro-NH-pAmb
87. H-(D,L)-Phe(3-Cl-4-EtO)-Pro-NH-pAmb
88. H-(D,L)-Phe(3,4-(MeO)₂)-Pro-NH-pAmb
89. Boc-(D,L)-Phe(3,4-(Me)₂)-Pro-NH-pAmb
90. H-(D,L)-Phe(3,4-(Me)₂)-Pro-NH-pAmb
91. Boc-(D,L)-Phe(3-Me-4-iPr)-Pro-NH-pAmb
92. H-(D,L)-Phe(3-Me-4-iPr)-Pro-NH-pAmb
93. Boc-(D,L)-Phe(2,3-(MeO)₂)-Pro-NH-pAmb
94. H-(D,L)-Phe(2,3-(MeO)₂)-Pro-NH-pAmb
95. Boc-(D,L)-Phe(2,5-(MeO) 2)-Pro-NH-pAmb
96. H-(D,L)-Phe(2,5-(MeO)₂)-Pro-NH-pAmb
97. Boc-(D,L)-Phe(3,5-(MeO)₂)-Pro-NH-pAmb
98. H-(D,L)-Phe(3,5-(MeO)₂)-Pro-NH-pAmb
99. Boc-(D,L)-Phe(3,4,5-(MeO)₃)-Pro-NH-pAmb
100. H-(D,L)-Phe(3,4,5-(MeO)₃)-Pro-NH-pAmb
101. Boc-(D,L)-Phe(2,4,6-(Me)₃)-Pro-NH-pAmb
102. H-(D,L)-Phe(2,4,6-(Me)₃)-Pro-NH-pAmb
103. Boc-(D)-αNal-Pro-NH-pAmb
104. H-(D)-αNal-Pro-NH-pAmb
105. H-(D)-βNal-Pro-NH-pAmb
106. Boc-(D,L)-αNgl-Pro-NH-pAmb
107. H-(D,L)-αNgl-Pro-NH-pAmb
108. Boc-(D,L)-βNgl-Pro-NH-pAmb
109. H-(D,L)-βNgl-Pro-NH-pAmb
110. H-(D,L)-1-Tic-Pro-NH-pAmb
111. Boc-(D)-3-Tic-Pro-NH-pAmb
112. H-(D)-3-Tic-Pro-NH-pAmb
113. 1-Icc-Pro-NH-pAmb
114. Boc-(D,L)-2-Tgl-Pro-NH-pAmb
115. H-(D,L)-2-Tgl-Pro-NH-pAmb
116. Boc-(D,L)-2-Tal-Pro-NH-pAmb
117. H-(D,L)-2-Tal-Pro-NH-pAmb
118. Boc-(D)-Phg-Pro-NH-pAmb
119. H-(D)-Phg-Pro-NH-pAmb
120. Boc-(D,L)-Phg(4-MeO)-Pro-NH-pAmb
121. H-(D,L)-Phg(4-MeO)-Pro-NH-pAmb
122. Boc-(D)-Chg-Pro-NH-pAmb
123. H-(D)-Chg-Pro-NH-pAmb
124. EtOOC-(D)-Chg-Pro-NH-pAmb
125. HOOC—CH₂-(D)-Chg-Pro-NH-pAmb
126. tBuOOC—CH₂-(D)-Chg-Pro-NH-pAmb
127. Boc-(D)-Cha-Pro-NH-pAmb
128. Me-(D)-Cha-Pro-NH-pAmb
129. Me-(Z)-(D)-Cha-Pro-NH-pAmb
130. N,N-Me₂-(D)-Cha-Pro-NH-pAmb
131. Boc-(D)-Trp(Boc)-Pro-NH-pAmb
132. H-(D)-Trp-Pro-NH-pAmb
133. Boc-(D,L)-Dpa-Pro-NH-pAmb
134. H-(D or L)-Dpa-Pro-NH-pAmb/a
135. H-(D or L)-Dpa-Pro-NH-pAmb/b
136. EtOOC-(D or L)-Dpa-Pro-NH-pAmb/a
137. EtOOC-(D or L)-Dpa-Pro-NH-pAmb/b
138. HOOC—CH₂-(D or L)-Dpa-Pro-NH-pAmb/a
139. HOOC—CH₂-(D or L)-Dpa-Pro-NH-pAmb/b
140. Boc-(D or L)-Dpa(4,4'-(Cl)₂)-Pro-NH-pAmb/a
141. Boc-(D or L)-Dpa(4,4'-(Cl)₂)-Pro-NH-pAmb/b
142. H-(D or L)-Dpa(4,4'-(Cl)₂)-Pro-NH-pAmb/a
143. H-(D or L)-Dpa(4,4'-(Cl)₂)-Pro-NH-pAmb/b
144. EtOOC-(D or L)-Dpa(4,4'-(Cl)₂)-Pro-NH-pAmb/a
145. EtOOC-(D or L)-Dpa(4,4'-(Cl)₂)-Pro-NH-pAmb/b
146. HOOC—CH₂-(D or L)-Dpa(4,4'-(Cl)₂)-Pro-NH-pAmb/a
147. HOOC—CH₂-(D or L)-Dpa(4,4'-(Cl)₂)-Pro-NH-pAmb/b
148. H-(D or L)-Dch-Pro-NH-pAmb/a
149. H-(D or L)-Dch-Pro-NH-pAmb/b
150. Boc-(D)-Val-Pro-NH-pAmb 151. H-(D)-Val-Pro-NH-pAmb
152. Boc-(D)-Leu-Pro-NH-pAmb
153. H-(D)-Leu-Pro-NH-pAmb
154. Boc-(D)-Gly(α-tBu)-Pro-NH-pAmb
155. H-(D)-Gly (α-tBu)-Pro-NH-pAmb
156. Boc-(D)-Ala(β-tBu)-Pro-NH-pAmb
157. H-(D)-Ala(β-tBu)-Pro-NH-pAmb
158. H-(D or L)-Msu-Pro-NH-pAmb/a
159. H-(D or L)-Msu-Pro-NH-pAmb/b
160. Boc-(Cyclo)Leu-Pro-NH-pAmb
161. H-(Cyclo)Leu-Pro-NH-pAmb
162. Boc-Gly-Pro-NH-pAmb
163. H-Gly-Pro-NH-pAmb
164. Ph-CH$_2$—CO-Gly-Pro-NH-pAmb
165. Ph-CH$_2$—CH$_2$—CO-Gly-Pro-NH-pAmb
166. Ph-CH$_2$-Gly-Pro-NH-pAmb
167. β-Naphthyl-CH$_2$-Gly-Pro-NH-pAmb
168. [3,4-(MeO)$_2$-phenyl]-Ch$_2$-Gly-Pro-NH-pAmb
169. Ph-CH$_2$—CO-Pro-NH-pAmb
170. Ph-CH$_2$—CH$_2$—CO-Pro-NH-pAmb
171. Ph-CH$_2$—CH$_2$—CH$_2$—CO-Pro-NH-pAmb
172. α-Naphthyl-CO-Pro-NH-pAmb
173. β-Naphthyl-CO-Pro-NH-pAmb
174. α-Naphthyl-CH$_2$—CO-Pro-NH-pAmb
175. β-Naphthyl-CH$_2$—CO-Pro-NH-pAmb
176. β-Naphthyl-SO$_2$-Pro-NH-pAmb
177. p-Tol-SO$_2$-Pro-NH-pAmb
178. Ph-CH$_2$—CH$_2$—SO$_2$-Pro-NH-pAmb
179. H-Asp-Pro-NH-pAmb
180. Boc-Asp(OMe)-Pro-NH-pAmb
181. H-Asp(OMe)-Pro-NH-pAmb
182. Ph-CH$_2$—CO-Asp(OMe)-Pro-NH-pAmb
183. Ph-CH$_2$—CH$_2$—CO-Asp(OMe)-Pro-NH-pAmb
184. (n-Pr)$_2$CH—CO-Asp-Pro-NH-pAmb
185. H-Asp(OBzl)-Pro-NH-pAmb
186. (n-Pr)$_2$CH—CO-Asp(OBzl)-Pro-NH-pAmb
187. Ph-CH$_2$—CO-Asp-Pro-NH-pAmb
188. Ph-CH$_2$—CH$_2$—CO-Asp-Pro-NH-pAmb
189. (n-Pr)$_2$CH—CO-Asp(OMe)-Pro-NH-pAmb
190. Z-(D)-Asp(OMe)-Pro-NH-pAmb
191. H-(D)-Asp-Pro-NH-pAmb
192. Z-(D)-Asp(OtBu)-Pro-NH-pAmb
193. H-(D)-Asp(OtBu)-Pro-NH-pAmb
194. Boc-(D)-Asp(OBzl)-Pro-NH-pAmb
195. H-(D)-Asp(OBzl)-Pro-NH-pAmb
196. Z-(D)-Glu(OtBu)-Pro-NH-pAmb
197. H-(D)-Glu(OtBu)-Pro-NH-pAmb
198. H-(D)-Glu-Pro-NH-pAmb
199. (D)-Ph-CH$_2$—CHOH—CO-Pro-NH-pAmb
200. (D)-Man-Pro-NH-pAmb
201. Boc-(D)-Phe-Aze-NH-pAmb
202. H-(D)-Phe-Aze-NH-pAmb
203. Boc-(D)-Phe-(D,L)-Pic-NH-pAmb
204. H-(D)-Phe-(D or L)-Pic-NH-pAmb/a
205. H-(D)-Phe-(D or L)-Pic-NH-pAmb/b
206. Boc-(D)-Phe-(D,L/trans)-Pic(4-Me)-NH-pAmb
207. H-(D)-Phe-(D,L/trans)-Pic(4-Me)-NH-pAmb
208. Boc-(D)-Phe-Pyr-NH-pAmb
209. H-(D)-Phe-Pyr-NH-pAmb
210. Boc-(D)-Phe-Hyp(O-tBu)-NH-pAmb
211. H-(D)-Phe-Hyp-NH-pAmb
212. Boc-(D)-Phe-(Me)Val-NH-pAmb
213. H-(D)-Phe-(Me)Val-NH-pAmb
214. Boc-(D)-Phe-Val-NH-pAmb
215. H-(D)-Phe-Val-NH-pAmb
216. Boc-(D)-Phe-Tia-NH-pAmb
217. H-(D)-Phe-Tia-NH-pAmb
218. H-(D)-Phe-Pro-NH-3-(6-am)-pico
219. Boc-(D)-Chg-Pro-NH-3-(6-Am)-pico
220. H-(D)-Chg-Pro-NH-3-(6-Am)-pico
221. HOOC—CH$_2$-(D)-Chg-Pro-NH-3-(6-Am)-pico
222. HOOC—CH$_2$-(D)-Chg-Pyr-NH-3-(6-Am)-pico
223. HOOC—CH$_2$-(D)-Chg-2-Phi-NH-3-(6-Am)-pico
224. HOOC—CH(Me)-(D)-Chg-Pro-NH-3-(6-Am)-pico
225. Boc-(D)-Phe-Pro-NH-3-(2-Me-6-Am)-pico
226. H-(D)-Phe-Pro-NH-3-(2-Me-6-Am)-pico
227. Boc-(D)-Chg-Pro-NH-3-(2-Me-6-Am)-pico
228. H-(D)-Chg-Pro-NH-3-(2-Me-6-Am)-pico
229. tBuOOC—CH$_2$-(D)-Chg-Pro-NH-3-(2-Me-6-Am)-pico
230. HOOC—CH$_2$-(D)-Chg-Pro-NH-3-(2-Me-6-Am)-pico
231. MeOOC—CH$_2$-(D)-Chg-Pro-NH-3-(2-Me-6-Am)-pico
232. Boc-(D)-Chg-Pro-NH-2-(5-Am)-pico
233. H-(D)-Chg-Pro-NH-2-(5-Am)-pico
234. HOOC—CH$_2$-(D)-Chg-Pro-NH-2-(5-Am)-pico
235. HOOC—CH$_2$-(D)-Chg-Pro-NH-5-(2-Am)-pym
236. (D)-Man-Pro-NH-4-(1-Am)-pip
237. Boc-(D)-Phe-Pro-NH-pHamb
238. H-(D)-Phe-Pro-NH-pHamb
239. Boc-(D)-Phe-Pro-NH-(2-MeO)-pAmb
240. H-(D)-Phe-Pro-NH-(2-MeO)-pAmb
241. Boc-(D)-Phe(4-Meo)-Pro-NH-(2-MeO)-pAmb
242. H-(D)-Phe(4-MeO)-Pro-NH-(2-MeO)-pAmb
243. HOOC—CH$_2$-(D)-Phe(4-MeO)-Pro-NH-(2-MeO)-pAmb
244. Boc-(D)-Chg-Pro-NH-(2-MeO)-pAmb
245. H-(D)-Chg-Pro-NH-(2-MeO)-pAmb
246. HOOC—CH$_2$-(D)-Chg-Pro-NH-(2-MeO)-pAmb
247. Boc-(D)-Chg-Aze-NH-(2-MeO)-pAmb
248. H-(D)-Chg-Aze-NH-(2-MeO)-pAmb
249. Boc-(D)-Chg-Pro-NH-(2-iPrO)-pAmb
250. H-(D)-Chg-Pro-NH-(2-iPrO)-pAmb
251. Boc-(D)-Chg-Pro-NH-(2-Cl)-pAmb
252. H-(D)-Chg-Pro-NH-(2-Cl)-pAmb
253. H-(D)-Phe-Pro-(D,L)(4-Am)-PhgOMe
254. Boc-(D,L)-Phe(3-OH)-Pro-NH-pAmb
255. BOC-(D,L)-1-Tic-Pro-NH-pAmb
256. H-(D)-Chg-Pro-NH-3-(2-MeO-6-Am)-pico The compounds of the formula I may be present as such or in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, malonic acid, succinic acid, hydroxysuccinic acid, sulfuric acid, glutaric acid, aspartic acid, pyruvic acid, benzoic acid, glucuronic acid, oxalic acid, ascorbic acid and acetylglycine.

The novel compounds can be used for the therapy and prophylaxis of all diseases in which thrombin plays a part. These are, in particular, thromboembolic disorders such as myocardial infarct, peripheral arterial occlusive disease, deep vein thrombosis, pulmonary embolism and stroke. They can additionally be used to prevent reocclusion after arterial vessels have been opened by mechanical methods or lysis.

The substances are furthermore suitable for preventing the formation of thrombin by directly inhibiting kallikrein.

Their particular advantage is that they are also effective after oral administration.

The invention also relates to the following substances of the formula II which are valuable intermediates for preparing the compounds I:

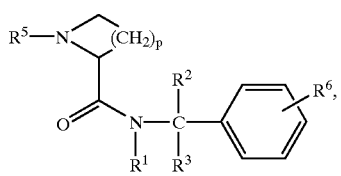

II in which $R^1$, $R^2$ and $R^3$ have the meanings stated for formula I, and $R^5$: is H, $C_{1-4}$-alkoxy-CO— or phenyl-$C_{1-3}$-alkoxy-CO—, $R^6$: is cyano, amidino or guanidino in the m or p position to $C(R^2,R^3)$ and p: is 1,2 or 3.

The abbreviations used in the description and the examples have the following meanings:

| | |
|---|---|
| Ala = | Alanine |
| Am = | amidino |
| (m or p)Amb = | (meta- or para-)amidinobenzyl |
| Asp = | Aspartic acid |
| Aze = | Azetidine-2-carboxylic acid |
| Boc = | t-Butyloxycarbonyl |
| Bzl = | Benzyl |
| Cbz = | Benzyloxycarbonyl |
| Cha = | Cyclohexylalanine |
| Chg = | Cyclohexylglycine |
| DCC = | Dicyclohexylcarbodiimide |
| Dch = | Dicyclohexylalanine |
| DCM = | Dichloromethane |
| DIPEA = | Diisopropylethylamine |
| DMF = | Dimethylformamide |
| Dpa = | Diphenylalanine |
| Dpg = | Diphenylglycine |
| EDC = | N'-(3-Dimethylaminopropyl)-N-ethylcarbodiimide |
| Glu = | Glutamic acid |
| Gly = | Glycine |
| pHamb = | para-hydroxyamidinobenzyl; (Ham = hydroxy-amidono [sic]) |
| HOBT = | Hydroxybenzotriazole |
| HoSu = | Hydroxysuccinimide |
| Hyp = | Hydroxyproline |
| Icc = | Isoquinolinecarboxylic acid |
| iPr = | Isopropyl |
| Leu = | Leucine |
| Man = | Mandelic acid |
| (Me)Val = | N-Methylvaline |
| Msu = | Methionine sulfone |
| (α or β)Nal = | (α- or β-)naphthylalanine |
| NBS = | N-Bromosuccinimide |
| Ngl = | Naphthylglycine |
| Ph = | Phenyl |
| Phe = | Phenylalanine |
| Phg = | Phenylglycine |
| 2-Phi = | 2-perhydroindole carboxylic acid |
| Pic = | Pipecolic acid (piperidine-2-carboxylic acid) |
| pico = | picolyl |
| | 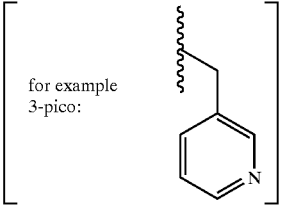 for example 3-pico: |
| pip | piperindinyl-methyl |
| | 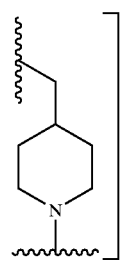 for example 4-pip: |
| Pro = | proline |
| pym | pyrimidyl-methyl |
| | 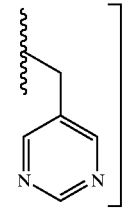 for example 5-pym: |
| PyBrop = | Bromo-tris-pyrrolidino-phosphonium hexafluorophosphate |
| Pyr = | 3,4-Pyrroline-2-carboxylic acid |
| RT = | room temperature |
| Tal = | Thienylalanine |
| TBAB = | Tetrabutylammonium bromide |
| tBu = | tertiary butyl |
| TEA = | Triethylamine |
| TEACl = | Tetraethylammonium chloride |
| TFA = | Trifluoroacetic acid |
| Tgl = | Thienylglycine |
| Tia = | Thiazolidine-4-carboxylic acid |
| Tic = | Tetrahydroisoquinolinecarboxylic acid |
| Tol = | Tolyl |
| Trp = | Tryptophan |
| Val = | Valine |
| Z = | Benzyloxycarbonyl (= Cbz) |

EXAMPLES

A. General Methods

A.I. Removal and Introduction of Protective Groups

A.I.a.

Protective groups are eliminated by the methods described by Gross and Meienhofer (E. Gross, J. Meienhofer "The Peptides; Analysis, Synthesis, Biology"; 1st ed. Vol. 3, Academic Press, New York (1981).

A.I.b.

Cbz protective groups are eliminated either by hydrogenolysis under standard conditions or with HF by the method described in Stewart, J. M.; Young, J. D. "Solid Phase Peptide Synthesis", 2nd edition; Pierce Chemical Company 1984).

A.I.c.

If the protected molecule contains only Boc protective groups, these are eliminated with HCl/dioxane or HCl/methylene chloride or $CF_3COOH$/methylene chloride under standard conditions (see Bodansky, M and Bodansky, A. "The Practice of Peptide Synthesis", Springer-Verlag, 1984).

A.II. General Methods for Hydrolyzing Ester Groups

A.II.a.

1 mmol of the ester is introduced into THF (4 ml/mmol) at 0° C. Then 1.2 eq. of LiOH (1 M solution) are added and the mixture is stirred at RT overnight. Aqueous workup results in the corresponding acid.

A.II.b.

1 mmol of the ester is introduced into MeOH (4 ml/mmol) at 0° C. Then 1.2 eq. of LiOH (1 M solution) are added and the mixture is stirred at RT overnight. Aqueous workup results in the corresponding acid.

A.II.c.

1 mmol of the ester is stirred in 2 ml of 2 N HCl at RT overnight. The product is subjected to aqueous workup.

A.III. General Method for Amidation

A.III.1.

The amidines, N-hydroxyamidines-and N-aminoamidines are prepared from nitrites by a method derived from Vieweg et al. (H. Vieweg et al. Pharmazie 39 (1984) 226) as follows:

1 eq of the nitrile is dissolved in pyridine/triethylamine (10/1; about 20–30 ml/g of substance). The solution is then saturated with $H_2S$ gas and left to stand in a closed vessel at RT overnight. The mixture is subsequently stirred into ice-water containing hydrochloric acid, and the resulting precipitate is filtered off with suction, washed with a large amount of water and then dried.

The substance is dissolved in acetone (about 20–30 ml/g of substance). MeI (1 ml/g of substance) is added and the solution is left to stand overnight. The S-methyl thioimidate hydroiodide is precipitated by adding diethyl ether and is reprecipitated from MeOH/diethyl ether to purify.

The salt is introduced into abs. MeOH (about 30 ml/g of substance). After addition of ammonium acetate (hydroxylammonium acetate or chloride is used to synthesize N-hydroxyamidines, and hydrazinium acetate or chloride is used to synthesize N-aminoamidines), the mixture is stirred at RT overnight. The suspension is filtered and then part of the solvent is removed under reduced pressure, and the amidino [sic] hydroiodide is precipitated by adding ether and is filtered off with suction. The crude product is then purified by RP-HPLC.

A.III.2

Alternatively, the amidation is also carried out by a Pinner reaction (D. Neilson in Patai "The Chemistry of Amidines and Imidates" 385–489, John Wiley & Sons, New York, 1975; R. Roger, D. Neilson Chem. Rev. 61 (1961) 179; also see Example 2)

A.III.3

Another possibility for the amidation comprises conversion of a nitrile group into a hydroxyamidine group with hydroxylamine hydrochloride and subsequent hydrogenation with $H_2$/Raney nickel (or $H_2$/Pd—C) to give the amidine.

10 mmol of the nitrile derivative are dissolved in 100 ml of MeOH and, after addition of 3 eq of hydroxylamine hydrochloride and 4.5 eq of TEA, stirred at room temperature until conversion is complete. The reaction mixture is subsequently concentrated and taken up in DCM. The organic phase is washed with water (pH 5–6), dried with $Na_2SO_4$ and concentrated.

The residue is dissolved in 100 ml of 5% strength methanolic HOAc and, after addition of Raney nickel (alternatively also Pd/C 10%), hydrogenated under a hydrogen atmosphere. After conversion of the precursor is complete, the catalyst is filtered off, and the filtrate is concentrated. The product is purified as required either by column chromatography on silica gel or reversed phase HPLC.

A.IV. General Method for the Guanidation of Amines

A.IV.1. Preparation of Free Guanidino Compounds

Free guanidino compounds are synthesized starting from the corresponding amines as precursor by the method of Miller et al. or Mosher et al. (A. E. Miller, J. J. Bischoff, Synthesis (1986) 777; K. Kim, Y. T. Lin, H. S. Mosher, Tetrahedron Letters 29 (1988) 3183).

A.IV.1.a.

1 eq of $K_2CO_3$ and 1 eq of amine are dissolved in 10 ml of water. 1 eq of aminoiminomethanesulfonic acid is then added in portions while stirring vigorously. The mixture is stirred for 24 hours and filtered. The filtered solid is the guanidine.

A.IV.1.b.

Equimolar amounts of an amine and of aminoiminomethanesulfonic acid are stirred in absolute MeOH (1 ml/mmol) at room temperature until a clear solution is formed. The solvent is then removed under reduced pressure, and the crude product is purified by RP-HPLC.

A.IV.2. Preparation of Alkoxycarbonylguanidines

The reactions to give alkoxycarbonylguanidines are carried out by the following literature methods:
1. R. J. Bergeron, J. S. McManis J. Org. Chem. 52 (1987) 1700
2. R. Dubey, S. Abuzar, S. Sharma, R. K. Chatterjee J. Med. Chem. 28 (1985) 1748
3. S. Shawkat, S. Sharma Synthesis (1992) 664
4. A. S. Vendrini, P. Lucietto, G. Fossati, C. Giordani Tetrahedron Lett. 33 (1992) 6541
5. Z. P. Tian, P. Edwards, R. W. Roeske Int. J. Pept. Prot. Res. 40 (1192) [sic] 119

A. V. General Esterification Methods

A.V.1.

1 eq of the carboxylic acid is stirred together with 1.1 eq of N'-(3-dimethylaminopropyl)-N-ethylcarbodiimide hydrochloride, 2 eq of alcohol and catalytic amounts of dimethylaminopyridine in methylene chloride at room temperature overnight. The solution is then diluted with methylene chloride, extracted with 20% $NaHSO_4$ solution, dried and concentrated under reduced pressure.

A.V.2.

1 eq of the carboxylic acid is boiled with the appropriate alcohol and catalytic amounts of p-toluene-sulfonic acid in chloroform (or toluene). After conversion is complete (TLC check), the solution is washed with saturated $NaHCO_3$ solution and brine, dried and evaporated.

B. General Synthetic Strategies

The compounds can be prepared in several ways.

1. Starting from appropriate protected A derivatives W—A—OH it is possible to couple on successively, by known methods, the building blocks H—B—COOW' (W'=alkyl) and H—N(R1)—C(R2R3)—(CH2)m-D-(NH)n—C(NH)NHR4 which are each in suitably protected form (see Scheme I). The protective groups on the reaction centers for the subsequent coupling are eliminated between the individual coupling steps as customary in peptide chemistry. All the building blocks can either be bought or synthesized by methods disclosed in the literature or similar thereto.

2. The syntheses can also take place in the reverse sequence by coupling H—N(R1)—C(R2R3)—(CH2)m-D-(NH)n—C(NH)NHR4 (R4 is a suitable protective group) to suitably protected W—B—COOH derivatives and subsequently A derivatives W—A—OH (see Scheme II).

3. The guanidine, amidine, N-hydroxyamidine and N-amino-amidine functionalities are either introduced in protected form (protonated or provided with suitable protective groups) with the building block H—N(R1)—C(R2R3)—(CH2)m-D-(NH)n—C(NH)NHR4 into the preparation of the active substances and subsequently deprotected, or else prepared after the coupling of the building blocks at the stage of W—A—B—CO—N(R1)—C(R2R3)—(CH2)m-D-NH2 by guanylation [sic] or of W—A—B—CO—N(R1)—C (R2R3)—(CH2)m-D-CN by amidation, N-hydroxyamidation or N-aminamidation.

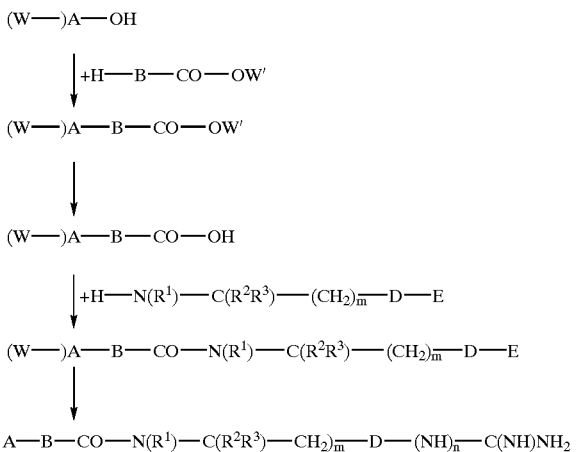

Scheme II

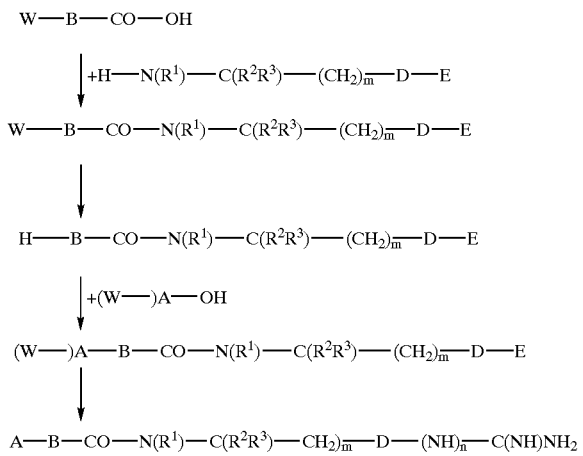

W is one of the conventional N-terminal protective groups (preferably Boc or Cbz) or a hydroxyl protective group and W' is methyl, ethyl, tert-butyl or benzyl.

E is —CN or —(NH)$_n$—C(NH)NHR$^4$ where R$^4$ is a protective group. For synthesizing guanidines (n=1), E can also be —NH—R$^4$ or NH$_2$.

For synthesizing N-amidinopiperidines (n=0), E can also be R$^4$ or H.

Literature for peptide chemistry:
1. E. Gross, J. Meienhofer "The Peptides; Analysis, Synthesis, Biology"; 1st. ed. Vol. 1; Academic Press, New York 1979
2. E. Gross, J. Meienhofer "The Peptides; Analysis, Synthesis, Biology"; 1st. ed. Vol. 2, Academic Press, New York 1980
3. E. Gross, J. Meienhofer "The Peptides; Analysis, Synthesis, Biology"; 1st. ed. Vol. 3, Academic Press, New York 1981
4. M. Deffner, E. Jaeger, P. Stelzel, P. Thamm, G. Wendenberg, E. Wünsch in Houben-Weyl "Methoden der [lacuna] Chemie", 4th edition, Vol. XV/1, Editor E. Wünsch, Georg Thieme Verlag Stuttgart, 1974
5. M. Deffner, E. Jaeger, P. Stelzel, P. Thamm, G. Wendenberg, E. Wünsch in Houben-Weyl "Methoden der [lacuna] Chemie", 4th edition, Vol. XV/2, Editor E. Wunsch, Georg Thieme Verlag Stuttgart, 1974
6. Bodansky, M. & Bodansky, A. "The Practice of Peptide Synthesis", Springer-Verlag, 1984

B.I.

Linkage of building blocks (W—)A—OH and H—B—CO—N(R1)—C(R2R3)—(CH2)m-D-(NH)nC(NH)NHR4 or H—B—CO—N(R1)—C(R2R3)—CH2)m-D-CN according to the general formula (I) (R$^1$, R$^2$, R$^3$=H, alkyl) and scheme II The hydrochloride HClxH—B—CO—N(R1)—C(R2R3)—(CH2)m-D-(NH)n—C(NH)NHR4 or HClxH—B—CO—N(R1)—C(R2R3)—(CH2)m-D-CN is initially prepared under standard peptide coupling conditions (see Bodansky, M. & Bodansky, A. "The Practice of Peptide Synthesis", Springer-Verlag, 1984) from W—B—CO—OH (W=a protective group, preferably Boc or Cbz) and the amine H—N(R1)—C(R2R3)—(CH2)m-D-(NH)n—C(NH)NHR4 or N—N(R1)—C(R2R3)—(CH2)m-D-CN with subsequent elimination of protective groups. The hydrochloride is then converted into the substances (corresponding to the general formula) as follows:

B.I.a. W—A—OH=Protected Amino Acid (Corresponding to the General Formula)

1 eq of a protected amino acid W—A—OH and 1.1 eq of the hydrochloride HClxH—B—CO—N(R1)—C(R2R3)—(CH2)m-D- (NH)nC(NH)NHR4 or HClxH—B—CO—N(R1)—C(R2R3)—(CH2)m-D-CN (corresponding to the general formula I) are reacted by standard peptide coupling methods to give the desired product. If E=CN, the nitrile functionality is converted according to A.III.1–3 into the amidino or hydroxyamidino group. The protective groups which are present are then eliminated by standard methods.

B.I.b.

A—OH=N-acyl-AA (AA are the amino acids mentioned under A in the general formula I, acyl=HOOC—C$_{1-6}$-alkylcarbonyl, C$_{1-12}$-alkylcarbonyl, phenyl-C$_{1-4}$-alkylcarbonyl, α- or β-naphthyl-C$_{1-4}$-alkylcarbonyl)

B.I.b.1.

Initially, a protected amino acid W—A—OH is coupled as described under B.I.a. to the hydrochloride described therein (R4 must be a conventional protective group). The N-terminal protective group on the amino acid is then removed (it must be possible to eliminate the protective group orthogonal to R4) and the latter is reacted with carboxylic acids acylOH (corresponding to the general formula) under standard peptide coupling conditions to give the desired product. To liberate the amidino, N-aminoamidino, N-hydroxyamidino or guanidino group, the latter is (if desired) eliminated under standard conditions (see A.I.). If E=CN, the nitrile functionality is converted according to A.III.1–3 into the amidino or hydroxyamidino group.

B.I.b.2.

Initially, the N-terminal amino acid H—A—OCH3 is reacted at the N-terminus with a carboxylic acid acylOH (corresponding to the general formula I) under standard peptide coupling conditions to give the N-acylated amino acid ester and then the ester group is hydrolyzed. The acylated amino acid is then coupled as described under B.I.b.1 with the hydrochloride HClxH—B—CO—N(R1)—C(R2R3)—(CH2)m-D-(NH)nC(NH)NHR4 or HClxH—B—CO—N(R1)—C(R2R3)—CH2)m-D-CN under standard conditions. If E=CN, the nitrile functionality is converted according to A.III.1–3 into the amidino or hydroxyamidino group. Finally, the protective groups are eliminated.

B.I.c.

A—OH=N-alkyl-AA (AA are the amino acids described for A in the general formula I, alkyl=$C_{1-12}$-alkyl, phenyl-$C_{1-4}$-alkylene, HOOC—$C_{1-6}$-alkylene, α- or β-naphthyl-$C_{1-4}$-alkylene)

One synthetic route (synthetic route 1) is assemblage of the alkylated building block A—OH (or A—B—CO—OH) with subsequent coupling of the building block H—B—CO—N(R1)—C(R2R3)—(CH2)m—D-(NH)nC(NH)NHR4 (or H—N(R1)—C(R2R3)—(CH2)m-D-(NH)nC(NH)NHR4) or H—B—CO—N(R1)—C(R2R3)—(CH2)m-D-CN (or H—N(R1)—C(R2R3)—(CH2)m—D-CN). An alternative route (synthetic route 2) is to synthesize the building block H—AA—B—CO—N(R1)—C(R2R3)—(CH2)m-D-(NH)nC—(NH)NHR4 or H—AA—B—CO—N(R1)—C(R2R3)—CH2)m-D-CN with subsequent N-terminal alkylation. Suitable protection for an amidino or guanidino group which is present is necessary. If E=CN, the nitrile functionality is converted according to A.III.1–3 into the amidino or hydroxyamidino group.

Synthetic Route 2

B.I.c.1

1 mmol of H—AA—B—CO—N(R1)—C(R2R3)—(CH2)m-D- (NH)nC(NH)NHR4 or H—AA—B—CO—N(R1)—C(R2R3)—(CH2)m-D-CN are dissolved in MeOH (10 ml). After addition of TEACl (1 mmol), NaBH$_3$CN (0.7 mmol) and RCHO (1.05 mmol), the mixture is stirred overnight. The solvent is removed under reduced pressure, and the residue is taken up in ethyl acetate. The organic phase is washed with water (2×) and saturated brine (1×) and dried with Na$_2$SO$_4$. The crude product after removal of the solvent is purified by RP-HPLC. If E=CN, the nitrile functionality is converted according to A.III.1–3 into the amidino or hydroxyamidino group.

B.I.c.2

1 mmol of H—AA—B—CO—N(R1)—C(R2R3)—(CH2)m—D-(NH)nC(NH)NHR4 or H—AA—B—CO(R1)—C(R2R3)—(CH2)m-D-CN are introduced together with K$_2$CO$_3$ (2.5 eq) into acetonitrile. After addition of the alkylating reagent, the mixture is stirred at 60° C. until conversion of the precursor is complete. Cooling and aqueous workup are followed by purification of the product by RP-HPLC. If E=CN, the nitrile functionality is converted according to A.III.1–3 into the amidino or hydroxyamidino group.

Synthetic Route 1

The alkylated building block A—OH (A=N-alkyl-AA) is prepared by the method of G. Iwasaki et al. (G. Iwasaki et al. Chem. Pharm. Bull 37 (1989) 280 and Chem. Lett. (1988) 1691). The following method is based on this literature method:

B.I.c.3.

1.5 eq of H—AA—OCH$_3$ or H—AA—B—COOCH$_3$ are stirred together with 1 eq of alkylating reagent and 2 eq of ammonium carbonate in nitromethane/water at 60° C. for 4 days. The mixture is subjected to aqueous workup and the product is purified by chromatography. The N-alkylamino group is protected with a suitable protective group and the ester functionality is then hydrolyzed and the product is reacted as in B.I.a.

B.I.c.4.

The N-alkyl-AA—OCH$_3$ or N-alkyl-AA—B—COOCH$_3$ building block can also be prepared by reduction amination from H—AA—OCH$_3$ or H—AA—B—COOCH$_3$ and aldehyde.

B.I.d.

A—OH=N-subst. aminocarbonyl-AA (AA are the amino acids described under A in the general formula; subst. aminocarbonyl=$C_{1-6}$-alkylaminocarbonyl, phenyl-$C_{1-4}$-alkylaminocarbonyl)

1 eq of H—AA—B—CO—N(R1)—C(R2R3)—(CH2)m-D-(NH)nC(NH)NHR4 or H—AA—B—CO—N(R1)—C(R2R3)—(CH2)m-D-CN is reacted with various isocyanates under standard conditions (Arnold et al. Chem. Rev. 57 (1957) 47) to give the corresponding urea derivatives. If E=CN, the nitrile functionality is converted according to A.III.1–3 into the amidino or hydroxyamidino group.

B.I.e. A=$X^{15}$—(CH$_2$)$_f$—SO2 ($X^{15}$ and f Correspond to the Variants Described under A in the General Formula I)

1.1 eq of the hydrochloride HCl×H—B—CO—N(R1)—C(R2R3)—(CH2)m-D-(NH)nC(NH)NHR4 or HCl×H—B—CON(R1)—C(R2R3)—(CH2)m-D-CN is reacted together with 1.5 eq of diisopropylethylamine, catalytic amounts of dimethylaminopyridine and 1 eq of a substituted sulfonyl chloride in methylene chloride After aqueous workup, the crude product is purified by RP-HPLC.

If E=CN, the nitrile functionality is converted according to A.III.1–3 into the amidino or hydroxyamidino group.

B.II. Linkage of the Amine H—N(R1)—C(R2R3)—(CH2)m-D-(NH)nC(NH)NHR4 or H—N(R1)—C(R2R3)—(CH2)m-D-CN to the building block A—B—CO—OH (corresponding to the general formula I and Scheme I.

The building block A—B—CO—OH is initially synthesized by the general methods in B.I. The amine H—N($R^1$)—C($R^2R^3$)—(CH$_2$)m-D—(NH)$_n$C(NH)NHR$^4$ is then coupled to the building block A—B—CO—OH as described below:

B.II.a. R1=H, R2, R3=H, $C_{1-4}$-alkyl, phenyl, phenyl-$C_{1-4}$-alkylene, n=0

B.II.a.1

The building block A—B—CO—OH (protected if necessary) is reacted under standard peptide coupling conditions with the amine H—N(R1)—C(R2R3)—(CH2)m-D-(NH)nC(NH)NHR4 (R4=—CO—$C_{1-20}$-alkyl, —CO—O—$C_{1-20}$-alkyl). After aqueous workup, the crude product is purified by RP-HPLC. Substances with R4=H can be obtained by standard deprotection methods.

B.II.a.2.

The building block A—B—COOH (protected if necessary) is reacted under standard peptide coupling conditions with the amine H—N(R1)—C(R2R3)—(CH2)m-D-CN (R1, R2, R3, D, m correspond to the general formula). After aqueous workup, the crude product is purified by RP-HPLC. The resulting nitrile is converted as described under A.III. into the amidine (R4=H), N-hydroxyamidine (R4=OH) or N-aminoamidine (R4=NH2).

B.II.b. R1=H; R2=H, $C_{1-4}$-alkyl, R3=H, $C_{1-4}$-alkyl, phenyl, phenyl-$C_{1-4}$-alkylene, n=1

B.II.b.1

The building block A—B—CO—OH (protected if necessary) is reacted under standard peptide coupling conditions with the amine H—N(R1)—C(R2R3)—(CH2)m-D-(NH)nC(NH)NHR4 (R4=—CO—$C_{1-20}$-alkyl, —CO—O—$C_{1-20}$-alkyl). After aqueous workup, the crude product is purified by RP-HPLC. Substances with R4=H can be obtained by standard deprotection methods.

B.II.b.2.

The building block A—B—COOH (protected if necessary) is reacted under standard peptide coupling conditions with the amine H—N(R1)—C(R2R3)—(CH2)m-D-NHW (W is a protective group which is orthogonal to protective groups which are also present). After aqueous workup, the crude product is purified by RP-HPLC. The resulting protected amine is liberated by standard deprotection methods and converted as described in A.IV. into the guanidine (R4=H).

B.II.c. R1=$C_{1-4}$-alkyl

These substances are prepared as described under B.II.b. The coupling reaction takes place with the coupling reagents pivaloyl chloride, PyBrop (Castro et al. Tetrahedron Lett. 31 (1990) 669; Castro et al. Tetrahedron Lett. 32 (1991) 1967; E. Frerot et al. Tetrahedron 47 (1990) 259) or BOPCl (M. J. O. Anteunis Int. J. Pept. Prot. Res. 29 (1987) 574).

B.II.d. R3=—CO—$X^{20}$ or —CO—CO—$X^{20}$ Corresponds to the General Formula)

B.II.d.1 R3=—CO—$X^{20}$ ($X^{20}$=OH, Alkoxy, Aryloxy, Aralkoxy)

The building block A—B—CO—N(R1)—CR2(COOH)—(CH2)m-D-(NH)nC(NH)NHR4 or A—B—CO—N(R1)—C(R2(COOH)—CH2)m-D-CN is synthesized by standard peptide coupling methods (cf. B.II.a.1.). For products with $X^{20}$=alkoxy, aryloxy or aralkoxy, the C-terminal acid is converted into the corresponding esters by standard esterification methods (see A.VI.). If D still bears the nitrile functionality this is converted according to AIII1–3 into the amidino or hydroxyamidino group.

B.II.d.2. R3=—CO—$X^{20}$ ($X^{20}$=Alkyl, Aryl, Aralkyl, CF3, C2F5)

The building block A—B—CO—N(R1)—CR2(COOH)—(CH2)m-D-(NH)nC(NH)NHR4 is prepared as described in B.II.d.1. The CO$X^{20}$ functionality is subsequently prepared in a Dakin-West reaction under standard conditions (W. Steglich, G. Höfle Angew. Chem. internat. Ed. 8 (1969) 981; W. Steglich, G. Hofle Chem. Ber. 102 (1969) 883). For this reaction, $R^4$ must be an alkoxycarbonyl group (preferably Boc or Cbz). Alternatively to this, A—B—CO—N(R1)—CR2—COOH—(CH2)m-D-CN may also be used in the Dakin-West reaction. In this case, the nitrile functionality is subsequently converted according to A.III.1–3 into the amidino or hydroxyamidino group.

A general experimental method for the Dakin-West reaction is as follows:

1 eq of the N-terminal protected tripeptide is stirred together with 2.5 eq of triethylamine, 5 eq of anhydride ([$X^{20}$—C(O)—O—(O)C—$X^{20}$), corresponding to the general formula I) and 0.1 eq of dimethylaminopyridine at 50–60° C. until no further $CO_2$ evolution is observed. The mixture is then stirred with saturated $Na_2CO_3$ solution at 60° C. for 2 h. The mixture is partitioned between ethyl acetate and saturated $NaHCO_3$ solution, and the organic phase is then extracted with saturated NaHCO3 solution (2×) and 20% $NaHSO_4$ solution, dried with $Na_2SO_4$ and evaporated. The crude product is purified by RP-HPLC.

B.II.d.3. R3=—CO—$X^{20}$ ($X^{20}$=Natural Amino Acid)

The building block A—B—CO—N(R1)—CR2(COOH)—(CH2)m-D-(NH)nC(NH)NHR4 is prepared as described in B.II.d.1. R4 must be an alkoxycarbonyl group (preferably Boc or Cbz) for the following reaction. Alternatively to this, A—B—CO—N(R1)—CR2(COOH)—(CH2)m-D-CN may also be used in the following reaction. These building blocks are subsequently reacted under standard peptide coupling conditions with a C-terminally protected amino acid. The desired products are subsequently liberated by removing the protective groups (as in A.I. and A.II.), and the nitrile functionality converted according to A.III.1–3 into the amidino or hydroxyamidino group.

B.II.d.4. R3=—CO—CO—X20

The procedure for assembling these substances is evident from PCT Application WO 94/08941. In accordance with the method, initially the building block W—N(R1)—CR2(CO—CO—X20)-D-(NH)n—C(NH)NHR4 (W is a suitable protective group and must be orthogonal to R4) is synthesized as follows:

An N-terminally protected amino acid W—NH—CR2(COOH)—(CH2)m-D- (NH)nC(NH)NHR4 (R4 must be a protective group orthogonal to W) is initially converted into the cyanohydrin W—NH—C(U)($R^2$)—CH(OH)—CN (with U=—(CH2)m-D-(NH)nC(NH)NHR4).

Subsequently, the nitrile functionality is converted into a carboxl group which is then esterified under suitable conditions (see A.V.), the N-terminal amino protective group W is eliminated, and the resulting amine is coupled to the building block A—B—CO—OH.

a. To form products with $X^{20}$=$C_{1-4}$-alkoxy or phenyl-$C_{1-4}$-alkoxy, the group X20 is introduced by transesterification.

b. To form products with $X^{20}$=amino acid, C-terminal ester hydrolysis and subsequent amino-acid coupling are carried out.

c. To form products with $X^{20}$=H, $C_{1-4}$-alkyl, phenyl, phenyl-$C_{1-4}$-alkylene, —$CF_3$ or —$C_2F_5$, initial hydrolysis of the C-terminal ester is followed by conversion into the Weinreb amide and subsequent reaction with the nucleophiles corresponding to $X^{20}$.

The resulting building block A—B—CO—NR1—C(U)($R^2$)—CH(OH)—C(O)—$X^{20}$ is oxidized under Swern conditions to the keto amide. Finally, protective groups which are still present are eliminated under standard conditions.

C. Preparation of Precursors

C.1. Preparation of Boc-(D)PheOSu 1 eq of Boc-(D)Phe-OH was stirred with 1.05 eq of hydroxysuccinimide and 1.05 eq of dicyclohexylcarbodiimide in acetonitrile (2.5 ml/mmol) at RT overnight. The suspension was then filtered and the filtrate was concentrated in a rotary evaporator. The residue comprised the product in virtually quantitative yield.

C.2. Preparation of Boc-(D,L)Dpa-OH

Boc-(D,L)Dpa-OH was prepared by the method of Kakkar et al. (L. Cheng, C. A. Goodwin, M. F. Schully, V. V. Kakkar J. Med. Chem. 35 (1992) 3364).

C.3. Preparation of Boc-(D,L)Dch-OH

Boc-(D,L)Dpa-OH (1 mmol) was hydrogenated in 12 ml of MeOH together with catalytic amounts of 5% $Rh/Al_2O_3$ under 5 bar. Filtration and removal of the solvent under reduced pressure resulted in the product in quantitative yield.

C.4. Preparation of Boc-1-(D,L)Tic-OH

Boc-1(D,L)Tic-OH was prepared by the method of R. T. Shuman et al. (R. T. Shuman et al. J. Med. Chem. 36 (1993) 314).

C.5. Preparation of Cbz-(D)PhePro-OSu i. 30 g of Cbz-(D)PheOH, 11.54 g of hydroxysuccinimide, 20.68 g of dicyclohexylcarbodiimide and 300 ml of dimethoxyethane were stirred at room temperature overnight. The suspension was filtered, the filtrate was concentrated, and the residue was dissolved in 200 ml of acetonitrile. The precipitated dicyclohexylurea was filtered off, and the filtrate was concentrated. 40 g of the succinimide ester (white solid) remained.

ii. 40 g of Cbz-(D)PheOSu, 17.31 g of proline, 12.63 g of NaHCO3, 225 ml of water and 225 ml of dimethoxyethane were stirred at room temperature overnight (evolution of gas). Subsequently the dimethoxyethane was removed under reduced pressure and the remaining aqueous solution was adjusted to pH 2 with 1N HCl. The oil which separated out was extracted with methylene chloride. The combined methylene chloride extracts were washed with saturated brine, dried with Na2SO4 and evaporated. 39.7 g of Cbz-(D)PheProOH (white solid) remained.

iii. 39.7 g of Cbz-(D)PheProOH, 11.53 g of hydroxysuccinimide, 20.66 g of dicyclohexylcarbodiimide and 400 ml of dimethoxyethane were stirred at room temperature overnight. The next day, dicyclohexylurea was filtered off, the filtrate was concentrated, and the residue was taken up in 300 ml of acetonitrile. Further precipitated dicyclohexylurea was filtered off, and the filtrate was concentrated under reduced pressure. 48.92 g of the hydroxysuccinimide ester remained.

C.6 Preparation of Boc-protected Phenylalanine Derivatives

Where the amino acids H—A—OH and Boc-A—OH could be not bought, they were prepared in a similar way to known literature methods Review: Houben-Weyl, volume E 16d/part 1 pages 406 et seq.)

Precursors frequently used for the alanine derivatives were ethyl benzophenoniminoacetate, diethyl acetamidomalonate and ethyl isonitrilacetate.

The following may be mentioned by way of examples 1 eq of diphenylglycinimine, 3 eq of $K_2CO_3$ and the appropriate benzyl bromide (or chloride or iodide) in acetonitrile were boiled overnight. After cooling, the mixture was filtered and the filtrate was concentrated. The residue was stirred in 1N HCl until the cleavage of the imine was complete. Subsequently, the aqueous phase was extracted with ethyl acetate, made basic with $Na_2CO_3$ and extracted with ethyl acetate. The combined organic extracts were dried with Na2SO4 and evaporated. The residue, the appropriate phenylalanine derivative, was provided with an N-terminal protective group (preferably Boc or Cbz) under standard conditions.

C.7 Preparation of Boc-protected Glycine Derivatives

Various glycine derivatives were prepared, for example, starting from ethyl isonitrilacetate and an appropriate ketone (see H.-J. Prätorius, J. Flossdorf, M.-R.Kula Chem.Ber. 195, 108, 3079).

Boc-Suberylglycine was synthesized in a similar way to the literature (O. P. Goel et al. Tetrahedron Lett. 1993, 34, 953).

Boc-(3-Ph)-Pro-OH was synthesized by a method similar to that of J. Y. L. Chung et al. (J. Y. L. Chung et al. J.Org.Chem. 1990, 55, 270).

Tetralinylglycine was prepared starting from 1,2-dihydronaphthalene, 1,2-dihydronaphthalene was initially converted with HBr into 1-tetralyl bromide (in a similar way to J. Med. Chem. 1994, 37, 1586). The bromide was then reacted with diethyl acetamidomalonate and cleaved by hydrolysis, and the resulting α-amino acid was converted under standard conditions into the Boc-protected form.

C.8 Preparation of Boc-(D)-(α-methyl)-Cha-OH

Boc-(D)-(α-methyl)-Cha-OH was prepared by hydrogenation of (D)-(α-methyl)-Phe-OH and subsequent introduction of the Boc protective group. Other possibilities for synthesizing α-substituted amino acids are the Bucherer synthesis starting from ketones, and the α-alkylation of α-amino acids C.9 Preparation of Hydroxyacetic Acid Derivatives Hydroxyacetic acid derivatives were prepared either by a method similar to that of S. Bajusz (WO93/18060) or starting from corresponding methyl acetate derivatives by α-hydroxylation using Davis' reagent (F. A. Davis, L. C. Vishwakarma, J. M. Billmers J.Org.Chem. 1984, 49, 3241).

C.10. p-(2-Aminoethyl)benzonitrile

Prepared as described in EP 445796

C.11. p-Cyanobenzylamine

C.11.a.

200 g of 4-cyanobenzyl bromide (1.02 mol), 700 ml of toluene, 200 g of sodium azide (3.07 mol), 32.9 g of TBAB and 700 ml of water were stirred at room temperature overnight, the two phases were then separated, and the toluene phase was washed again with water. The volume of solvent was reduced to ⅕ under reduced pressure.

C.11.b.

267.6 g of triphenylphosphine (1.02 mol) were introduced into 500 ml of tetrahydrofuran at 10° C. The azide, dissolved in 165 ml of tetrahydrofuran, was slowly added dropwise to this solution (evolution of nitrogen). After the addition was complete, 27.6 ml of water (1.53 mol) were slowly added, and the reaction mixture was stirred at room temperature for 48 h. The solution was then concentrated in a rotary evaporator, and the residue was taken up in cold 3N HCl (1 l). The precipitated solid was filtered off with suction, and the filtrate was washed with toluene until the triphenylphosphine oxide was completely removed. The acidic aqueous phase was then adjusted to pH=9 with $Na_2CO_3$ (solid), the precipitated solid was filtered off, and the filtrate was extracted with diethyl ether. The solid was dissolved in diethyl ether and dried together with the ethereal extracts. The ether volume was then reduced and the hydrochloride was precipitated by passing in gaseous HCl. The salt was filtered off, washed with diethyl ether and dried in air (salt sublimes under high vacuum). Yield: 137.6 g C.11.c.

The preparation of p-cyanobenzylamine was also prepared in good yields from p-cyanobenzyl bromide via the phthalimide with subsequent cleavage by hydrazine hydrate.

Synthesis via the urotropinium salt is likewise suitable (W. Walter et al., Ann. 1962, 660, 60).

C.12. m-Cyanobenzylamine

Prepared as indicated in the literature (Pharmazie 1978, 33, 15)

C.13. (D,L)-1-(4-Cyanophenyl)-ethylamine

C.13.a. N-(p-Cyanobenzyl)benzophenone imine 270 g (2.0 mol) of anhydrous $K_2CO_3$ were added to a solution of 150 g (0.8 mol) of 97% pure benzophenone imine and 144.8 g (0.74 mol) of p-cyanobenzyl bromide in 450 ml of acetonitrile, and the mixture was stirred at room temperature for 6 h. After the inorganic salts had been filtered off with suction, the solvent was substantially removed by distillation, 300 ml of water were added to the residue, and the mixture was extracted several times with ethyl acetate. The organic phase was washed 2× with water, dried over $Na_2SO_4$ and evaporated to dryness. Digestion with ether resulted in 180 g of white crystals, melting point 101–102° C.

C.13.b. 1-(4-Cyanopyhenyl)ethylamine 20.7 g (0.07 mol) of N-(p-cyanobenzyl)benzophenone imine were added dropwise to a solution of lithium diisopropylamide, prepared from 8.15 g (0.08 mol) of diisopropylamine and 48.3 ml (0.08 mol) of 15% strength solution of butyllithium in hexane, in 100 ml of abs. tetrahydrofuran at −70° C. and the mixture was stirred for 15 minutes. Then 9.94 g (0.07 mol) of methyl iodide were added dropwise, and the temperature of the reaction mixture was allowed to rise to room temperature. After addition of 100 ml of water, the mixture was extracted several times with ether, the ether phase was washed with 5% strength citric acid solution, 5% strength $NaHCO_3$ solution and water and dried over $Na_2SO_4$, and the ether was distilled off. The residue was dissolved in 150 ml of tetrahydrofuran, 100 ml of 1N HCl were added, and the mixture was stirred at room temperature overnight. The tetrahydrofuran was distilled out of the reaction mixture under reduced pressure, the remaining acidic phase was extracted several times with ether to remove the benzophenone, subsequently the acidic phase was made alkaline with aqueous $K_2CO_3$ solution while cooling in ice, and the oily base was extracted with methylene chloride. The extract was dried over $K_2CO_3$. After the methylene chloride had been stripped off, 9.7 g (95%) of a yellowish oil remained and were used without further purification in the next stage.

C.14. 4-Aminomethyl-3-methoxybenzonitrile

C.14.a. 3-Nitro-4-methylbenzonitrile 399 g (2.56 mol) of p-tolunitrile were added over the course of 90 min to 1 l of fuming nitric acid at −10° C. 1 h after the addition, the mixture was poured into 2.5 l of ice/$H_2O$, whereupon a solid precipitated and was removed on a suction filter funnel and washed with water until the pH was neutral. The yield of the product was 363 g (88%). $^1$H-NMR ($CDCl_3$; δ in ppm): 8.3 (d, 1H); 7.8 (dd, 1H); 7.5 (dd, 1H); 2.7 (s, 3H)

C.14.b. 3-Amino-4-methylbenzonitrile 120 g of 3-nitro-4-methylbenzonitrile were suspended in 1.2 l of EtOH and hydrogenated in the presence of 7 g of Pd/C(10%) with 50 l of hydrogen at RT. After removal of the catalyst on Celite, the solvent was stripped off to result in 95 g of pure product (97%). $^1$H-NMR ($DMSO-d_6$; δ in ppm): 7.1 (dd, 1H); 6.90 (d, 1H); 6.85 (dd, 1H); 5.35 (s, 2H, NH2); 2.15 (s, 3H)

C.14.c. 3-Hydroxy-4-methylbenzonitrile

A solution of 49.2 g (0.72 mol) of $NaNO_2$ in 217 ml of water was added dropwise over the course of 30 min to 85 g (0.72 mol) of 3-amino-4-methylbenzonitrile in 1.8 l of 6N HCl at 0–5° C. The mixture was subsequently stirred at 0–5° C. for a further 30 min and then at the boiling point for 1 h. After the solution had cooled it was possible to extract the product with ethyl acetate and therefrom in the form of the phenolate with ice-cold 5N NaOH. The aqueous phase was then acidified to pH 3 with 6N HCl, and the product was extracted with ethyl acetate. 41 g (43%) of the phenol were obtained. $^1$H-NMR ($DMSO-d_6$; δ in ppm): 10.3 (s, OH); 7.25 (dd, 1H); 7.15 (d, 1H); 7.1 (dd, 1H); 2.20 (s, 3H)

C.14.d. 3-Methoxy-4-methylbenzonitrile 15 g (0.11 mol) of 3-hydroxy-4-methylbenzonitrile dissolved in 30 ml of DMF were added dropwise to a suspension of 0.11 mol of NaH and 30 ml of DMF and stirred until no further evolution of $H_2$ was observed. Then 10.6 ml (0.17 mol) of methyl iodide were added dropwise, and the mixture was stirred at RT for 1 h. The solution was poured into ice-water, and the product was extracted with 7:1 ether/ethyl acetate. After the solvent was stripped off, the product began slowly to crystallize. 14.8 g (89%) of the product were obtained. $^1$H-NMR ($CDCl_3$; δ in ppm): 7.2 (m, 2H); 7.02 (s, 1H); 3.85 (s, 3H); 2.25 (s, 3H)

C.14.e. 4-Bromomethyl-3-methoxybenzonitrile 14.7 g (0.1 mol) of 3-methoxy-4-methylbenzonitrile were dissolved in 210 ml of 1,2-dichloroethane, brominated in portions with 19.1 g (0.11 mol) with NBS over the course of 1 h in the presence of catalytic amounts of AIBN at 82° C. and, after the addition was complete, stirred at 82° C. for a further 30 min. After addition of n-heptane, precipitated succinimide was removed, and the solvent was stripped off. The product contained traces of the corresponding benzal bromide in addition to small amounts of precursor. $^1$H-NMR ($DMSO-d_6$; δ in ppm): 7.60 (dd, 1H); 7.50 (d, 1H); 7.40 (dd, 1H); 4.68 (s, 2H); 3.96 (s, 3H)

C.14.f. 4-Phthalimidomethyl-3-methoxybenzonitrile 24.4 g (108 mol) of 4-bromomethyl-3-methoxybenzonitrile, dissolved in 125 ml of DMF, and 20.0 g of potassium phthalimide were stirred at RT for 24 h and then at 50° C. for 1 h. The mixture was poured into water, whereupon the product precipitated as solid. 21.5 g (68%) of the product were obtained. $^1$H-NMR ($DMSO-d_6$; δ in ppm): 7.9 (m, 4H); 7.5 (d, 1H); 7.35–7.25 (m, 2H); 7.78 (s, 2H); 3.92 (s, 3H)

C.14.g. 4-Aminomethyl-3-methoxybenzonitrile 21.2 g (73 mmol) of 4-phthalimidomethyl-3-methoxybenzonitrile dissolved in 290 ml of THF were added to 10.6 ml of hydrazine hydride and stirred at RT for 20 h. Then 180 ml of 2N HCl were added dropwise and, after 1.5 h, the solvent was completely stripped off.

The residue was taken up in MTBE, extracted with 1N HCl, adjusted to pH 9–10 with 2N NaOH and extracted with DCM. 8.0 g (68%) it [sic] product were obtained. $^1$H-NMR ($DMSO-d_6$; δ in ppm): 7.55 (dd, 1H); 7.40 (dd, 1H); 7.37 (d, 1H); 3.85 (s, 3H); 3.70 (s, 2H); 2.5–1.6 ($NH_2$).

C.15 4-Aminomethyl-3-isopropoxybenzonitrile

C.15.a. 3-i-Propoxy-4-methyl-benzonitrile 7.0 g of 3-hydroxy-4-methylbenzonitrile (52.6 mmol) were deprotonated with 57.8 mol [sic] of NaH in 100 ml of DMF, and 7.4 ml of 2-bromopropane were added at 0° C. After 45 min, the temperature was raised to 50° C. and stirring was continued for 5 h. The reaction mixture was poured into water, and the product was extracted with ether. The product was purified by column chromatography on silica gel (mobile phase: dichloromethane/10% heptane). 6.3 g (68%) were obtained; melting point 60–61° C.

C.15.b. 4-Bromomethyl-3-i-propoxybenzonitrile 6.1 g of 3-i-propoxy-4-methylbenzonitrile (33.4 mmol) were brominated with NBS and AIBN as in Example (C.14.e.). The product resulted in almost quantitative yield.

$^1$-H-NMR ($DMSO-d_6$-, δ in ppm): 7.65–7.30 (3H, aromatic H); 4.85 (1H, CH), 4.63 (2H, $CH_2$), 1.40–1.25 (6H, 2×$CH_3$)

C.15.c. 4-Aminomethyl-3-i-propoxybenzonitrile (hydrochloride)

8.8 g of the bromide (i) (33.4 mmol) were dissolved in 100 ml of MeOH and, at 40° C., slowly added dropwise to 150 ml of ammonia-saturated MeOH. The solvent was stripped off, and the product was taken up in dichloromethane, washed with 1N sodium hydroxide solution and precipitated as hydrochloride with ethereal HCl. 2.6 g were obtained.

$^1$-H-NMR ($DMSO-d^6$-, δ in ppm): 8.6 (3H, $NH_3^+$), 7.65–7.40 (3H, aromatic H), 4.80 (1H, CH); 4.00 (2H, $CH_2$), 1.4–1.3 (6H, 2×$CH_3$)

C.16 4-Aminomethyl-3-chlorobenzonitrile

C.16.a. 4-Bromomethyl-3-chlorobenzonitrile

3-Chloro-4-methylbenzonitrile was brominated with NBS and AIBN as in Example (C.14.e.).

$^1$-H-NMR ($DMSO-d_6$, δ in ppm): 8.10 and 7.85 (3H, aromatic H), 4.80 (2H, $CH_2$)

C.16.b. 4-Aminomethyl-3-chlorobenzonitrile 10.0 g of the bromide were reacted as in Example (C.14.f.) with potassium phthalimide. 9.6 g of phthalimidomethyl-3-chlorobenzonitrile were obtained and were cleaved with hydrazine hydrate as in Example (C.14.g.). The free amine (4.0 g) was obtained by extraction with dichloromethane from the aqueous phase adjusted to pH 9–19 [sic] with sodium hydroxide solution.

$^1$-H-NMR ($DMSO-d_6$, δ in ppm): 7.95–7.78 (3H, aromatic H); 3.85 (2H, $CH_2$), 2.1 (broad signal, 2H, $NH_2$)

D. EXAMPLES

Example 1

Boc-(D)-Phe-Pro-NH-(4-Am)-2-phenethyl 10 mmol of isobutyl chloroformate were added over the course of 2 minutes to a solution of 10 mmol of Boc-(D)-Phe-Pro-OH and 11 mmol of N-methylmorpholine in 10 ml of DMF at −15° C. and subsequently, after stirring for 10 minutes, a solution of 10 mmol of p-cyanobenzylamine and 11 mmol of N-methylmorpholine in 3 ml of DMF was added. After stirring at −15° C. for 3 hours, a TLC check (DCM/MeOH, 9/1) showed no detectable starting compound.

For isolation, the reaction mixture was poured into 200 ml of water, whereupon an oil separated out and solidified after a short time and was, after crushing, filtered off with suction. The still moist residue was dissolved in a mixture of 250 ml of ethyl acetate and 50 ml of ether and washed successively with a 5% strength aqueous citric acid, bicarbonate and saturated brine solutions. Drying over $Na_2SO_4$ was followed by removal of the solvent by distillation under reduced pressure, and the residue was mixed with n-hexane and subsequently filtered off with suction. Recrystallization from 50 ml of ether acetate afforded 7.4 mmol of TLC-pure product which was converted into the amidine hydroiodide by the $H_2S$ method as in A.III.1.

Yellowish crystals were obtained; melting point 158–165° C. FAB-MS: 508 (M+H$^+$).

Example 2

H-(D)-Phe-Pro-NH-(4-Am)-2-phenethyl

Elimination of the Boc group from Example 1 was carried out as in A.I.c. The solvent mixture employed in this case was 1:1 dichloromethane/ethyl acetate. The dihydrochloride was obtained in the form of white crystals; melting point 203–206° C. (decomposition); FAB-MS: 408 (M+H$^+$)

Example 3

Boc-(L)-Phe-Pro-NH-pAmb

The compound was prepared starting from Boc-(L)-PheOH and H-Pro-p-cyanobenzylamide×HCl as in B.I. and subsequent conversion of the nitrile into the amidine as in A.III.1. The amidine hydroiodide obtained in this way was converted into the amidine hydroacetate on an acetate ion exchanger (IRA 420).

$^1$-H-NMR (d$_6$-DMSO, δ in ppm): 8.4(m,1H,NH); 7.75(d, 2H,Ar—H); 7.45(d,2H,Ar—H); 7.2(m,5H,Ar—H); 7.18/7.02(2d,1H,NH); 4.48–4.18(m,4H,CH$_2$/2-α-H); 3.6(m,2H, Pro); 3.0–2.7(m,2H,CH$_2$-Ph); 2.18–1.8(m,4H,Pro); 1.3–1.2 (2s,9H,Boc) MS: 494 (M+H$^+$); 394 (−Boc); mp: 142° C.

Example 4

H-(L)-Phe-Pro-NH-pAmb

The compound was prepared by elimination of Boc from Example 3 as in A.I.c. The resulting dihydrochloride was converted into the dihydroacetate by column chromatography on silica gel by adding acetic acid; melting point 69° C.; FAB-MS: 394 (M+H$^+$)

Example 5

Boc-(D)-Phe-Pro-NH-pAmb 2.0 g (14.6 mmol) of isobutyl chloroformate were added over the course of 2 min to a solution of 5.1 g (14.2 mmol) of Boc-D-Phe-Pro-OH and 1.53 g (15.2 mmol) of N-methylmorpholine in 15 ml of DMF at −15° C., the mixture was then stirred for 10 min, and subsequently a solution of 1.9 g (14.2 mmol) of p-cyanobenzylamine and 1.53 g of N-methylmorpholine in 3 ml of DMF was added. After the mixture had been stirred at −15° C. for 3 hours, a TLC check (CH$_2$Cl$_2$/MeOH, 9/1) showed no detectable starting compound.

For the isolation, the reaction mixture was poured into 200 ml of water, whereupon an oil separated out and, after a short time, solidified and was broken up and filtered off with suction. The still moist residue was dissolved in a mixture of 250 ml of ethyl acetate and 50 ml of ether and washed successively with 5% strength aqueous citric acid, bicarbonate and saturated brine solutions. After drying over Na$_2$SO$_4$, the solvent was distilled off under reduced pressure, and the residue was mixed with n-hexane and subsequently filtered off with suction. Recrystallization from 50 ml of ethyl acetate yielded 5.6 g of TLC-pure Boc-(D)-Phe-Pro-p-cyanobenzylamide; melting point 156–157° C.

Thioamide formation: 4.1 g of the above compound and 4 ml of triethylamine were dissolved in 40 ml of pyridine, saturated at 0° C. with H$_2$S and left to stand at room temperature overnight. A TLC check (CH$_2$Cl$_2$/MeOH, 9/1) showed that the conversion to the thioamide was complete. For the isolation, most of the pyridine was distilled off under reduced pressure, the residue was taken up in 250 ml of ethyl acetate, and the solution was washed with brine, 5% strength citric acid and NaHCO$_3$ solutions. Drying and removal of the solvent by distillation resulted in 4.1 g of pure crystalline thioamide.

Amidine formation: The thioamide was dissolved in 150 ml of acetone and, after addition of 7 ml of methyl iodide, left to stand at room temperature overnight. The solvent was stripped off and then the amorphous residue was stirred with dry ether and subsequently dried. The S-methyl thiomidic [sic] methyl ester hydroiodid was dissolved in 50 ml of ethanol, 15 ml of 10% strength ammonium acetate solution were added, and the mixture was heated at 60° C. for 3 hours. For the isolation, the solvent was stripped off, the residue was dissolved in 100 ml of CH$_2$Cl$_2$, the insolubles were filtered off and subsequently the CH$_2$Cl$_2$ was distilled off. Digestion with an ethyl acetate/diethyl ether mixture removed the impurities soluble therein. The remaining mixed iodide/acetate was dissolved in acetone/water (3/2) and converted into the pure acetate using an IRA acetate ion exchanger. The solution was evaporated to dryness and the residue was freeze dried. 3.8 g of TLC-pure (CH$_2$Cl$_2$/MeOH/50% glacial acetic acid, 20/5/1) Boc-D-Phe-Pro-NH-pAmb were isolated in the form of the acetate, melting point 195–200° C. (decomposition).

Example 6

Ac-(D)-Phe-Pro-NH-pAmb 10.4 g (0.05 mol) of Ac-D-Phe-OH, 6.3 g (0.055 mol) of N-hydroxysuccinimide and 11.4 g (0.055 mol) of dicyclohexylcarbodiimide were dissolved in 150 ml of acetonitrile and stirred at room temperature overnight. The precipitate which formed was filtered off, the solvent was distilled off, and the residue was dried under reduced pressure and employed without further purification for the next reaction.

13.3 g (0.05 mol) of (4-cyanobenzyl)prolylamide hydrochloride (see Example 10) were dissolved in 100 ml of methylene chloride and, at 0° C., successively 15 ml of triethylamine and a solution of the above Ac-D-Phe-O-succinimide in 70 ml of methylene chloride were added. The reaction mixture was stirred at room temperature overnight and washed successively with water, 5% strength citric acid, 5% strength NaHCO$_3$ and sodium chloride solutions. After drying and removal of the solvent by distillation, the residue was purified on a silica gel acid [sic] (eluent: CH$_2$Cl$_2$/

Example 7

H-(D)-Phe-Pro-NH-pAmb 4.9 g (10 mmol) of the compound obtained according to Example 5 were dissolved in a mixture of 100 ml of chloroform and 100 ml of ethyl acetate and saturated with HCl gas at −15° C. with exclusion of moisture. After one hour, TLC (CH$_2$Cl$_2$/MeOH/50% glacial acetic acid, 20/5/1) show no detectable Boc compound.

Most of the excess HCl gas was removed by passing in nitrogen at −15° C., during which the dihydrochloride separated out as fine crystals. After addition of 50 ml of ether to complete the deposition, the precipitate was filtered off with suction and washed with a (1/1) ethyl acetate/ether mixture. The residue was dissolved in water, treated with active carbon and lyophilized. 3.7 g (95% of theory) of the dihydrochloride were obtained as white crystals, melting point 215° C. (decomposition); FAB-MS 394 (MH$^+$).

Example 8

H-(D)-Phe-Pro-N(Me)-pAmb

The compound was prepared by reacting Boc-(D)-Phe-Pro-OH and N-methyl-4-cyanobenzylamine as in Example 5. The Boc group was subsequently eliminated as in A.I.c. The dihydrochloride was obtained in the form of an amorphous solid; FAB-MS: 408 (M+H$^+$)

Example 9

Me-(D)-Phe-Pro-NH-pAmb 4.0 g of the below compound (Example 10) were dissolved in 25 ml of EtOH, 1.55 g of 32% strength HCl and 0.6 g of 10% Pd/C were added and the mixture was then hydrogenated. Conversion was quantitative after 1 h (according to TLC: methylene chloride/MeOH/50% strength HOAc; 35/15/5). After the catalyst had been removed by filtration with suction and the solvent by distillation, the residue was converted with 100 ml of ethyl acetate into a white powder and, after dissolving in water, lyophilized. 3.1 g of dihydrochloride were isolated, and this sintered at 100° C. and decomposed above 215° C.

Example 10

Z-Me-(D)-Phe-Pro-NH-pAmb (4-Cyanobenzyl)-prolylamide [sic] hydrochloride 276 g of BocPro-Osuccinimide (0.88 mol) were introduced into 2 l of methylene chloride at 0° C. To this solution were successively added 163.9 g of 4-cyanobenzylamine hydrochloride (0.97 mol) and 230 ml of diisopropylethylamine (1.34 mol). The suspension was stirred in a thawing ice bath for 48 h and then filtered. The filtrate was extracted with 20% strength NaSO$_4$ [sic] solution (4×), saturated Na$_2$HCO$_3$ [sic] solution (3×) and saturated brine (2×), dried and concentrated in a rotary evaporator. 299 g of product remained and, after recrystallization from methyl tert-butyl ether, melted at 124–125° C.

299 g of the Boc-protected compound were dissolved in 1 l of diethyl ether. Ethereal HCl solution was added (excess HCl) and the mixture was then stirred overnight. The precipitated salt was filtered off, washed with diethyl ether and dried under reduced pressure. The crude product was recrystallized from EtOH. Yield: 200 g; melting point: 209–213° C. (decomposition)

Z-Me-(D)-Phe-Pro-p-cyanobenzylamide 3.1 g (0.01 mol) of Z-Me-(D)-Phe-OH and 1.49 g (0.011 mol) of hydroxybenzotrialzole [sic] were dissolved in 50 ml of DMF and, at 0° C., 2.1 g (0.01 mol) of dicyclohexylcarbodiimide were added. After 30 min, 2.7 g (0.01 mol) of (4-cyanobenzyl)prolylamide [sic] hydrochloride and 2.2 ml of N-methylmorpholine were added. The reaction mixture was stirred at room temperature overnight, the precipitated urea was filtered off, and the solvent was distilled off under reduced pressure. The residue was dissolved in 100 ml of ethyl acetate and washed successively with water, 5% strength citric acid solution, 5% strength NaHCO3 solution and brine solution After drying and removal of the solvent by distillation, 4.7 g (90% of theory) of viscous oil remained and were used in the subsequent reaction.

Amidation by the Pinner Reaction 12.3 g of acetyl chloride were added dropwise to a solution of 8.9 g of abs. EtOH in 25 ml of methylene chloride at 0° C., and the mixture was stirred for 40 min. Subsequently, at 0° C., a solution of 4.7 g of the above substance in 30 ml of abs. methylene chloride was added dropwise. The reaction mixture was left to stand at 0° C. for 4 days. The solution was concentrated under reduced pressure, the residue was diluted with 100 ml of methylene chloride, and this solution was shaken with ice-cold 15% strength K$_2$CO$_3$ solution. Drying and removal of the solvent by distillation yielded the crude imino ether base which was dissolved in 30 ml of MeOH, and 0.8 g of ammonium acetate was added. The solution was left to stand at room temperature for 2 days.

After removal of the solvent by filtration [sic], the residue was purified on a silica gel column (methylene chloride/MeOH/50% strength HOAc; 40/10/2.5). The evaporated eluates were taken up in toluene and concentrated in a rotary evaporator again. The residue was dissolved in water, treated with active carbon and subsequently lyophilized. 4.1 g (76% of theory) of white crystals remained, and these sintered at 83° C. and melted at 178–184° C.

Example 11

HOOC-CH$_2$-(D)-Phe-Pro-NH-pAmb 2.4 g of t-BuOOC-CH$_2$-(Boc)-(D)-Phe-Pro-NH-pAmb hydroacetate (from Example 13) were stirred in 80 ml of absolute DCM and 15 ml of ethereal HCl at room temperature overnight. The solvent was stripped off under reduced pressure, and the residue was extracted by stirring with 2:1 DCM/acetone and filtered off. 1.6 g of the product were obtained as hydrochloride or dihydrochloride or as mixture of the two salt forms in the form of a white solid. Melting point: 210–220° C.

Example 12

MeOOC-CH$_2$-(D)-Phe-Pro-NH-pAmb 0.5 g of the compound from Example 11 was stirred together with 2 ml of ethereal HCl, 3 ml of DCM and 3 ml of methanol at room temperature for 30 h. The solvent was concentrated and the residue was extracted by stirring several times with ether. 0.5 g of product was obtained as MeOH, 50/2) and subsequently converted into the amidine as in Example 5.

Acetate: melting point 220–224° C. (decomposition), FAB-MS: 436 (M+H$^+$)

hydrochloride or dihydrochloride or mixture of the two salt forms. Melting point 104–120° C.

Example 13 t-BuOOC-CH$_2$-(Boc)-(D)-Phe-Pro-NH-pAmb a) H-(D)-Phe-Pro-p-cyanobenzylamide 5.6 g of Boc-(D)-Phe-Pro-p-cyanobenzylamide (from Example 5) were cleaved as in A.I.c. 4.6 g (95%) of the product were obtained as hydrochloride in the form of white crystals.

b) t-BuOOC-CH$_2$-(Boc)-(D)-Phe-Pro-p-cyanobenzylamide 6.19 g of H-(D)-Phe-Pro-p-cyanobenzylamide (15 mmol) were heated together with 0.98 g of tert-butyl bromoacetate (5 mmol) and 0.63 g of ammonium carbonate in a mixture of 35 ml of water and 8 ml of nitromethane at 50° C. for 2 h. The mixture was then extracted with ethyl acetate, the organic phase was washed several times with 0.1N hydrochloric acid, the aqueous phases were extracted with DCM, and the combined organic phases were dried over MgSO$_4$. After the solvent had been stripped off, the product was precipitated as hydrochloride with ethereal HCl. 2.6 g (98%) of the hydrochlorid were obtained. The excess H-(D)-Phe-Pro-p-cyanobenzylamide was recovered by extracting the aqueous phases at pH 10 with DCM.

c) t-BuOOC-CH$_2$-(Boc)-(D)-Phe-Pro-p-cyanobenzylamide 2.6 g of the above hydrochloride (4.9 mmol) were stirred together with 1.2 g of (Boc)$_2$O (5.5 mmol) and 1.87 ml of DIPEA (11 mmol) in 95 ml of absolute DCM at room temperature overnight. The solvent was then concentrated, the residue was taken up in ether and washed with 0.1N hydrochloric acid and then with water, and the solvent was dried over MgSO$_4$ and stripped off under reduced pressure. After the residue had been extracted by stirring with hexane, 2.8 g of product were obtained as a white solid.

d) t-BuOOC-CH$_2$-(Boc)-(D)-Phe-Pro-NH-pAmb

Conversion of the nitrile functionality into the amidino functionality took place as in A.III.1. with a total yield of 96%.

Conversion of the hydroiodide into the hydroacetate took place using an IRA acetate ion exchanger; melting point 116–121° C.

Example 14

EtOOC-(D)-Phe-Pro-NH-pAmb

The compound was prepared by reacting N-(ethoxycarbonyl)-(D)-phenylalanine (J. Org. Chem. 1980, 45, 4519) with (4-cyano-benzyl)prolylamide [sic] hydrochloride (from Example 10) and subsequent amidine formation (as in Example 5). White crystals of hydroacetate were obtained; melting point 105–107° C.; FAB-MS: 466 (M+H$^+$)

Example 15

Boc-(D)-Phe-Pro-NH-mAmb

The compound was obtained from Boc-(D)-Phe-Pro-OH with m-cyanobenzylamine (as in Example 5). The hydroacetate was obtained in the form of white crystals; melting point 130–133° C.

Example 16

H-(D)-Phe-Pro-NH-mAmb

Elimination of the Boc group from Example 15 took place as in A.I.c. The white crystals of the dihydrochloride melted at 155–160°; FAB-MS: 394 (M+H$^+$)

Example 17

Z-(D)-Phe-Pro-(D,L)-(4-Am)-PhgOH a) 39.7 g (100.1 mmol) of Z-(D)-Phe-Pro-OH, 11.53 g (100.1 mmol) of HOSu and 20.66 g (100.1 mmol) of DCC were stirred in 400 ml of dimethoxyethane at RT for 18 h. The solid was subsequently filtered off, the filtrate was concentrated and the residue was taken up in acetonitrile. The reprecipitated solid was filtered off and the organic solution was evaporated to dryness under reduced pressure. Crude yield: 48.9 g of Z-(D)-Phe-Pro-Osuccinimide.

b) 24.53 g of H-Phg(4-CN)-OEt×HCl, 34.9 ml of DIPEA and 41.9 g of Z-(D)-Phe-Pro-Osuccinimide were dissolved in 200 ml of DMF and stirred at RT for 18 h. For workup, DMF was removed under reduced pressure and the remaining residue was taken up in DCM. The organic phase was extracted with 1N HCl, dried with NaSO$_4$ [sic] and concentrated under reduced pressure. 54.04 g of Z-(D)-Phe-Pro-NH-Phg(4-CN)-OEt remained.

c) 54.04 g of Z-(D)-Phe-Pro-NH-Phg(4-CN)-OEt were dissolved in 340 ml of THF/EtOH/water (3:1:1) and, after addition of 3.05 g of LiOH, stirred at RT for 18 h. The reaction mixture was subsequently concentrated under reduced pressure, and the remaining aqueous solution was acidified to pH 2 and extracted with ethyl acetate. The combined organic extracts were washed with saturated NaCl solution, dried with NaSO$_4$ [sic] and evaporated to dryness in a rotary evaporator. Crude yield: 40.94 g of Z-(D)-Phe-Pro-NH-Phg(4-CN)—OH.

d) 2.78 g of Z-(D)-Phe-Pro-NH-Phg(4-CN)—OH, 18.9 ml of pyridine and 8.7 ml of TEA were mixed in a reaction flask and saturated with H$_2$S gas. The solution was left to stand at room temperature for 18 h. The reaction mixture was subsequently poured into 2 l of ice-water, and the aqueous phase was adjusted to pH 3 with 1N HCl. The precipitated product was filtered off and dissolved in ethyl acetate, and the solution was dried with NaSO$_4$ [sic]. After removal of the ethyl acetate under reduced pressure, the residue was mixed with 20 ml of acetone and 3.5 ml of MeI [sic] and stirred at RT for 18 h. The volatile constituents were then removed under reduced pressure, and the crude thiomethylimine hydroiodide was stirred in 8 ml of MeOH and 8 ml of methanolic ammonium acetate solution (10% strength) for 18 h. The reaction mixture was subsequently concentrated, the residue was taken up in DCM, and the precipitated solid was filtered off. Concentration of the filtrate resulted in 3.75 g of crude product. This was purified by reverse phase HPLC chromatography. Yield: 1.5 g.

$^1$H-NMR (d$_6$-DMSO, δ in ppm): 8.4–8.0 (2m, 1H, NH); 7.7–7.4 (m, 4H, Ar—H); 7.3–7.1 (m, 10H, Ar—H); 7.0 (sb, 1H, NH); 5.2–4.8 (m, 3H, OCH2/α-Phg); 4.6–4,2 (m, 2H, α-Pro/α-Phe); 3.6–3.2 (2H, δ-Pro); 3.0–2.6 (m, 2H, CH2-Ph); 2.2–1.6 (m, 4H, α/β-Pro)

FAB-MS: 572 (M+H$^+$); melting point 155–158° C.

Example 18

Z-(D)-Phe-Pro-(D,L)-(4-Am)-Phg-OMe a) 5.14 ml of abs. MeOH and 6.16 ml of acetyl chloride were added to 14 ml of DCM at 0° C. Subsequently 2.78 g of Z-(D)-Phe-Pro-NH-Phg(4-CN)—OH in 10 ml of DCM were added to this solution and it was left to stand at room temperature for 48 h. For workup, the reaction mixture was concentrated, and the residue was taken up in ethyl acetate and washed with cold $K_2CO_3$ solution (5% strength). After the organic phase had been dried with $NaSO_4$ [sic], the solvent was removed in a rotary evaporator, and the crude iminomethyl ether was left to stand in 6.5 ml of MeOH and 6.5 ml of methanolic ammonium acetate solution (10% strength) for 18 h. Concentration of the solution resulted in 2.4 g of the crude product, which was purified by reversed phase HPLC chromatography.

$^1$H-NMR ($d_6$-DMSO, δ in ppm): 9.6–9.2 (b, N—H); 8.75/8.5 (2d, 1H, NH); 7.8 (m, 2H,Ar—H); 7.6 (m, 2H, Ar—H); 7.35–7.2 (m, 10H, Ar—H); 7.05 (sb, 1H, NH); 5.6 (2d, 2H, OCH2); 5.0–4.2 (3m, 4H, α-Pro/α-Phe/α-Phg); 3.6 (2s, 3H, OCH3); 3.5–3.2 (2H, δ-Pro); 3.0–2.6 (m, 2H, CH2-Ph); 2.2–1.6 (m, 4H, (β/γ-Pro)

FAB-MS: 586 (M+H$^+$); melting point 129–131° C.(hydrochloride)

Example 19

H-(D)-Phe-Pro-(D,L)-(4-Am)-Phg-OH

The compound was prepared by elimination of Cbz from Example 17.

$^1$H-NMR ($d_6$-DMSO, δ in ppm): 9.0 (b, NH); 8.7/8.4/8.05 (3d, 1H, NH); 7.8–7.0 (m, 9H, Ar—H); 5.1/4.9 (d, 1H, α-Phg); 4.45–4.0 (m, 2H, α-Pro/α-Phe); 3.8–3.0 (m, 2H, δ-Pro); 3.0–2.7 (m, 2H, CH2-Ph); 2.2–1.4 (m, 4H, β/γ-Pro)

FAB-MS: 438 (M+H$^+$); melting point 149–150° C. (dihydrochloride)

Example 20

Boc-(D)-Phe-Pro-(4-Am)-Phg-CH$_2$Ph a) N-(Diphenylmethylene)-4-cyanobenzylamine 33.73 g (0.2 mol) of 4-cyanobenzylamine and 36.25 g (0.2 mol) of benzophenone imine were dissolved in 540 ml of DCM at room temperature and stirred overnight. The reaction mixture was subsequently washed with 2×90 ml of water and dried with $Na_2SO_4$, and the solvent was removed in a rotary evaporator. 55.59 g (93.7%) of the crude product remained. Recrystallization from 550 ml of iPrOH resulted in 97.67 g (80.4%) of pure product. $^1$H-NMR (CDCl$_3$, δ in ppm): 7.7–7.15 (m, 9H, Ar—H); 4.65 (s, 2H, CH$_2$—N)

b) N-(Diphenylmethylene)-α-(β-phenylacetyl)-4-cyanobenzylamine 63.3 mmol of LDA were introduced into 45 ml of THF at −30° C. Subsequently 15 g (50.61 mmol) of N-(diphenylmethylene)-4-cyanobenzylamine in 75 ml of THF were slowly added dropwise. After stirring at −30° C. for a further 10 min, 8.6 g (55.7 mmol) of acid chloride (dissolved in 7.5 ml of THF) were slowly added at −78° C. After the reaction mixture had been stirred for 18 h (the reaction temperature was allowed to rise to room temperature overnight), it was cooled to −20° C., and 3.6 ml of HOAc and 17.25 ml of water were added. After the reaction mixture had reached room temperature, the THF was removed under reduced pressure, the residue was taken up in ether, the organic phase was washed with saturated NaCl solution and dried, and the ether was removed in a rotary evaporator. 26.18 g of crude product remained and were employed without further purification in the next step.

c) α-(β-Phenylacetyl)-4-cyanobenzylamine 26.18 g of the synthesized crude ketone were stirred in 250 ml of 0.25 N HCl at room temperature overnight. The reaction mixture was subsequently extracted with DCM, and the aqueous phase was lyophilized. After reversed phase HPLC separation, 2.52 g of α-(β-phenylacetyl)-4-cyanobenzylamine remained. $^1$H-NMR (DMSO-$d_6$, δ in ppm): 9.0 (s, 3H, NH$_3$); 8.0/7.75 (2d, 4H); 7.25 (m, 3H);: 7.0 (dd, 2H); 5.7 (s, 1H, NCH); 3.9/3.6 (2d, Ph-CH$_2$—); FAB-MS (M$^+$): 250 d) 2.51 g (6.92 mmol) of Boc-D-Phe-Pro-OH were introduced into 40 ml of abs. DCM at −20° C. Subsequently, 0.80 ml of N-methylmorpholine and 0.90 ml (6.92 mmol) of isobutyl chloroformate were added to the solution, and the latter was stirred at −20° C. for 20 min. After addition of a further 0.80 ml of methylmorpholine and 2.52 g (6.92 mmol) of α,(β-phenylacetyl)-4-cyanobenzylamine [sic], the reaction mixture was stirred for a further hour. For workup, the reaction mixture was diluted with 50 ml of DCM, and the organic solution was washed with 1 N HCl (3×40 ml), 5% strength NaHCO$_3$ solution (2×40 ml) and saturated NaCl solution (1×40 ml). After drying and concentration of the solution, 3.97 g of the crude product remained. This was purified by column chromatography (hexane/ethyl acetate). Yield: 3.43 g.

e) 3.43 g (5.77 mmol) of Boc-(D)-Phe-Pro-Phg(4-CN)—CH$_2$-Ph×HOAc were dissolved in 21.9 ml of pyridine and 9.85 ml of TEA. This solution was saturated with H$_2$S gas at room temperature and stirred overnight. Subsequently H$_2$S was removed as far as possible with nitrogen, and this solution was poured into 5% strength citric acid. The aqueous phase was extracted several times with ethyl acetate. The combined organic phases were washed with saturated NaCl solution and, after drying with Na$_2$SO$_4$, concentrated in a rotary evaporator. Crude yield: 4.13 g.

f) 4.13 g of the crude thioamide were stirred together with 23.3 ml of acetone and 4.05 ml of Mel [sic] for 18 h. The reaction solution was then concentrated in a rotary evaporator. The residue was dissolved in 9.1 ml of abs. MeOH and 9.1 ml of abs [sic] NH$_4$OAc solution (10% strength in MeOH) and stirred for 18 h. After this, the reaction mixture was evaporated to dryness and the residue was purified by reversed phase HPLC chromatography (acetonitrile/water). Yield: 680 mg (hydroacetate).

$^1$H-NMR ($d_6$-DMSO, δ in ppm): 9.4/9.2/8.8/8.6 (4d, 1, N—H); 7.9–7.5 (m, 4H, Ar—H); 7.3–7.0 (m, 11H, Ar—H/NH); 6.0/5.7 (2m, 1H, α-Phg); 4.4–2.6 (m, 8H); 2.2–1.6 m, 4H, β/γ-Pro); 1.3–1.2 (2sb, 9H, Boc)

MS: 612 (M+H$^+$), 512 (−Boc), 365, 161, 120

Example 21

H-(D)-Phe-Pro-(4-Am)-Phg-CH$_2$Ph

The compound was prepared by elimination of Boc (HCl/dioxane) from Example 20. $^1$H-NMR ($d_6$-DMSO, δ in ppm): 9.5/9.4 (2d, 1H, NH); 9.4/9.2 (2sb, 3H, N—H); 7.8 (d, 2H, Ar—H); 7.6 (d, 2H, Ar—H); 7.4–7.0 (m, 10H, Ar—H); 5.8/5.6 (2d, 1H, α-Phg); 4.35 (m, 2H, α-Phe/α-Pro); 4.1/3.9 (4d, 2H, CH2-Ph); 3.7 (m, 2H, CH2); 3.2/3.0 (2m, 2H, CH2); 1.8–1.6 (2m , 4H, β/γ-Pro)

MS: 512 (M+H$^+$), 393, 252, 161 (dihydrochloride)

Example 22

H-(D)-Phe-Pro-NH-pAm-[(D,L)-a-Me]-benzyl (a) N-(p-Cyanobenzyl)benzophenone imine 270 g (2.0 mol) of anhydrous K$_2$CO$_3$ were added to a solution of 150 g (0.8 mol) of 97% pure benzophenone imine and 144.8 g (0.74 mol) of p-cyanobenzyl bromide in 450 ml of acetonitrile, and the mixture was left to stir at room temperature for 6 h. After the organic salts had been removed by filtration with suction, the solvent was substantially removed by distillation, and the residue was mixed with 300 ml of water and extracted several times with ethyl acetate. The organic phase was washed 2× with water, dried over $Na_2SO_4$ and evaporated to dryness. Digestion with ether resulted in 180 g of white crystals, melting point 101–102° C.

(b) 1-(4-Cyanophenyl)ethylamine 20.7 g (0.07 mmol) of N-(p-cyanobenzyl)benzophenone imine were added dropwise to a solution of lithium diisopropylamide prepared from 8.15 g (0.08 mol) of diisopropylamine and 48.3 ml (0.08 mol) of 15% strength solution of butyllithium in hexane—in 100 ml of abs. tetrahydrofuran, at −70° C., and the mixture was stirred for 15 minutes. Then 9.94 g (0.07 mol) of methyl iodide were added dropwise, and the temperature of the reaction mixture was allowed to rise to room temperature. After addition of 100 ml of water and extraction several times with ether, the ether phase was washed with 5% strength citric acid solution, 5% strength $NaHCO_3$ solution and water and dried over $Na_2SO_4$, and the ether was distilled off. The residue was dissolved in 150 ml of tetrahydrofuran, 100 ml of 1N HCl were added, and the mixture was stirred at room temperature overnight. The tetrahydrofuran was distilled out of the reaction mixture under reduced pressure, the remaining acid phase was extracted several times with ether to remove the benzophenone, then the acid phase was made alkaline with aqueous $K_2CO_3$ solution while cooling in ice, and the oily base was extracted with methylene chloride. The extract was dried over $K_2CO_3$. After the methylene chloride had been stripped off, 9.7 g (95%) of a yellowish oil remained and was used without further purification in the next reaction.

(c) Boc-D-phenylalanyl-proline (D,L)-α-methyl-4-cyanobenzylamide 16.2 g of diisopropylamine and 22 ml (30 mmol) of propanephosphonic anhydride (50% strength solution in ethyl acetate) were added dropwise to a solution of 3.65 g (25 mmol) of 1-(4-cyanophenyl)ethylamine and 9.1 g (25 mmol) of Boc-D-Phe-Pro-OH in 150 ml of methylene chloride at −50° C. The mixture was stirred for 2 h, during which the temperature was allowed to rise from −5° to 20° C. The organic phase was washed with water, 5% strength sodium bicarbonate and 5% strength citric acid solutions, dried over $Na_2SO_4$ and evaporated to dryness. A pale yellowish crystalline residue was obtained and was used without further purification in the next reaction.

(d) (D)-Phenylalanyl-proline (D,L)-α-methyl-4-amidinobenzylamide 4.1 g of the above compound and 4 ml of triethylamine were dissolved in 40 ml of pyridine, saturated with $H_2S$ at 0° C. and left to stand at room temperature overnight. A TLC check ($CH_2Cl_2$/MeOH, 9/1) showed that conversion to the thioamide was complete. For isolation, the pyridine was substantially removed by distillation under reduced pressure, and the residue was taken up in 250 ml of ethyl acetate and washed with brine, 5% strength citric acid and $NaHCO_3$ solutions. Drying and removal of the solvent by distillation resulted in 4.1 g of pure crystalline thioamide.

The thioamide was dissolved in 150 ml of acetone and, after addition of 7 ml of methyl iodide, left to stand at room temperature for 6 h. After the solvent had been stripped off, the amorphous residue was extracted by stirring with dry ether and subsequently dried. The S-methyl thioimidic methyl ester hydroiodide was dissolved in 50 ml of ethanol, 15 ml of 10% strength ammonium acetate solution were added, and the mixture was heated at 60° C. for 3 h. For isolation, the solvent was stripped off, the residue was dissolved in 100 ml of $CH_2Cl_2$, the insoluble constituents were filtered off, and subsequently the $CH_2Cl_2$ was distilled off. Digestion with an ethyl acetate/diethyl ether mixture removed the impurities soluble therein. The remaining mixed iodide/acetate was dissolved in acetone/water (3/2) and converted into the pure acetate by means of an IRA acetate ion exchange, and subsequently freeze-dried. A white powder was isolated, melting point 110–115° C.; FAB-MS: 508 (M+H$^+$)

(e) H-(D)-Phe-Pro-NH-pAm[(D,L)-α-Me]-benzyl

The above compound was dissolved in 70 ml of $CH_2Cl_2$, and 80 ml of HCl-saturated ethyl acetate were added. After a short time, a precipitate separated out and was completed by adding ether. The latter was filtered off with suction, washed with ether until HCl-free and dried under reduced pressure. White crystals were obtained, melting point 190–195° C. (dihydrochloride), FAB-MS: 407 (M$^+$).

Example 23

Me-(D)-Phe-Pro-(D or L) (4 Am)-PhΨ[$CH_2OH$]/a

N-(p-Cyanobenzyl)-benzophenone imine was hydroxymethylated in acetonitrile with anhydrous potassium carbonate, tetrabutylammonium iodide and paraformaldehyde. White crystals: melting point 115–117° C. The alcohol group was subsequently etherified with t-butyldimethylsilyl chloride and cleaved with 0.1 N methanesulfonic acid in THF to give the protected (D,L)-α-hydroxymethyl-p-cyanobenzylamine. This amine was coupled under standard conditions with Z-Me-(D)-Phe-Pro-OH and converted with $H_2S$ into the thioamide which was separated into the diastereomers by column chromatography. Pure diastereomer a was amidated and subsequently the protective groups were eliminated with acid catalysis and by hydrogenolysis. The white crystals obtained after freeze drying melted at 175–180° C., FAB-MS: 438 (M+H$^+$).

Example 24

Me-(D)-Phe-Pro-(D or L)(4 Am)-PhΨ[$CH_2OH$]/b

Amorphous white crystals [sic] were obtained from the diastereomerically pure thioamide b by amidation and elimination of protective groups, FAB-MS: 438 (M+H$^+$).

Example 25

Boc-(D)-Phe(4-F)-Pro-NH-pAmb

Prepared by reacting Boc-D-Phe(4-F)-OH with N-(4-cyanobenzyl)prolinamide and subsequent amidation. White crystals, melting point 184–187° C. (hydroacetate)

Example 26

H-(D)-Phe(4-F)-Pro-NH-pAmb

Elimination of the Boc group under standard conditions from compound 25. Dihydrochloride: white crystals, melting point 225–230° C., FAB-MS: 412 (M+H$^+$)

Example 27

Boc-(D)-Phe(4-Cl)-Pro-NH-pAmb

The compound was prepared as in Example 3 from Boc-(D)-Phe(4-Cl)-OH; melting point 124–137° C. (hydroacetate)

Example 28

H-(D)-Phe(4-Cl)-Pro-NH-pAmb

Elimination of the Boc group from Example 27 was carried out as in A.I.c. The compound was obtained as dihydrochloride; melting point 221–234° C.

Example 29

Boc-(D,L)-Phe(4-Br)-Pro-NH-pAmb

The compound was prepared starting from Boc-(D,L)-Phe(4-Br)—OH and H-Pro-p-cyanobenzylamide×HCl as in Example 3.

$^1$H-NMR (D$_6$-DMSO, δ in ppm): 8.4/8.1 (t, 1H, NH); 7.78 (2d, 2H, Ar—H); 7.2 (m, 2H, Ar—H); 7.0 (2d, 1H, NH); 4.5–4.2 (m, 4H, CH2/2 α-H); 3.6 (m, 2H, Pro); 3.0–2.6 (m, 2H, CH2-Ph); 2.15–1.7 (m, 4H, β/γ-Pro); 1.3/1.2 (2d, 9H, Boc)

FAB-MS: 575/574 (M+H$^+$); melting point 171° C. (decomp.) (hydroacetate)

Example 30

H-(D,L)-Phe(4-Br)-Pro-NH-pAmb

The compound was prepared by elimination of Boc from Example 29.

$^1$H-NMR (d$_6$-DMSO, δ in ppm): 9.2 (b, 4H); 8.6/8.5 (2t, 1H, NH); 7.8 (2d, 2H, Ar—H); 7.4 (m, 4H, Ar—H); 7.2 (m, 2H, Ar—H); 7.2 (b, 3H, NH); 4.38 (2dd, 3H, CH2/α-H); 4.2 (m, 1H, α-H); 3.8–3.6 (m, 2H, Pro); 3.1–2.8 (m, 2H, CH2); 2.2–1.7 (m, 4H, Pro); FAB-MS: 474 (M+H$^+$); melting point 56° C. (decomp.) (dihydroacetate)

Example 31

H-(D)-Phe(4-OH)-Pro-NH-pAmb

The compound was obtained by elimination of the benzyl group by hydrogenolysis using Pd/C similar to the conventional cleavage of Z protective groups (A.I.b.) from Example 37. Removal of the catalyst by filtration and stripping off the solvent resulted in the dihydrochloride by precipitation with ethereal HCl.

Melting point 129–140° C.

Example 32

Boc-(D)-Phe(4-MeO)-Pro-NH-pAmb

Preparation took place as in Example 3 from Boc-(D)-Phe(4-MeO)OH; melting point 67–83° C. (hydroacetate)

Example 33

H-(D)-Phe(4-MeO)-Pro-NH-pAmb

Elimination of the Boc group from Example 32 was carried out as in A.I.C. Melting point 215–227° C. (dihydrochloride)

Example 34

Boc-(D,L)-Phe(4-EtO)-Pro-NH-pAmb

Preparation took place as in Example 3 from Boc-(D,L)-Phe(4-EtO)OH; melting point 115–145° C. (hydroacetate)

Example 35

H-(D,L)-Phe(4-EtO)-Pro-NH-pAmb

Elimination of the Boc group from Example 34 was carried out as in A.I.c.

Melting point 218–230° C. (Dihydrochlorid)

Example 36

Boc-(D)-Phe(4-BzlO)-Pro-NH-pAmb

The preparation took place as in Example 3 from Boc-(D)-Phe(4-BzlO)OH:

Melting point 111–125° C. (hydroacetate)

Example 37

H-(D)-Phe(4-BzlO)-Pro-NH-pAmb

Elimination of the Boc group from Example 36 was carried out as in A.I.c.;

Melting point 201–210° C. (dihydrochloride)

Example 38

Boc-(D,L)-Phe(4-Et)-Pro-NH-pAmb

Preparation took place as in Example 3 from Boc-(D,L)-Phe(4-Et)OH to give the product-hydroacetate.

$^1$H-NMR (DMSO-d$_6$, δ in ppm): 9.25 (2H, amidine), 8.85 (2H, amidine), 8.42 and 8.09 (together 1H, NH), 7.80–6.95 (9H, aromatic H and NH), 4.45–4.20 (4H, 2×CH and 1×CH$_2$), 3.75–ca. 3.0 (2H, CH$_2$), 3.0–2.6 (2H, CH$_2$), 2.6–ca. 2.5 (2H, CH$_2$), 2.3–1.5 (4H, 2×CH$_2$, 1.3–ca. 1.2 (9H, Boc), ca. 1.2–1.05 (3H, CH$_3$)

Example 39

H-(D,L)-Phe(4-Et)-Pro-NH-pAmb

The dihydrochloride was obtained by elimination of the Boc group from Example 38 as in A.I.c.

$^1$H-NMR (DMSO-d$_6$, δ in ppm): 9.55–9.40 (2H, amidine), 9.32–9.20 (2H, amidine), 8.90 and 8.70 (together 1H, NH), 8.85–8.75 and 8.40–8.30 (together 3H, NH$_3^+$), 7.90–7.05 (8H, aromatic H), 4.50–4.10 (4H, 1×CH$_2$ and 2×CH), 2.6–ca. 2.5 (2H, CH$_2$), 1.9–1.3 (4H, 2×CH$_2$), 1.2/1.1 (3H, CH$_3$)

Example 40

Boc-(D,L)-Phe(4-iPr)-Pro-NH-pAmb

The hydroacetate was obtained by reacting Boc-(D,L)-Phe(4-iPr)OH as in Example 3.

$^1$H-NMR (DMSO-d$_6$, δ in ppm): 9.25 (2H, amidine), 8.50 (2H, amidine), 8.43 and 8.09 (together 1H, NH), 7.80–6.95 (9H, aromatic H and NH), 4.45–4.20 (4H, 2×CH and 1×CH$_2$), 3.7–ca. 3.2 (2H, CH$_2$), 3.0–2.6 (3H, CH$_2$ and CH), 2.2–1.5 (4H, 2×CH$_2$), 1.3–ca. 1.2 (9H, Boc), ca. 1.2–1.05 (6H, 2×CH$_3$)

Example 41

H-(D,L)-Phe(4-iPr)-Pro-NH-pAmb

The dihydrochloride was obtained by eliminination of the Boc group from Example 40 as in A.I.c.

$^1$H-NMR (DMSO-d$_6$, δ in ppm): 9.50–9.40 (2H, amidine), 9.30–9.20 (2H, amidine), 8.90 and 8.70 (together 1H, NH), 8.75 and 8.30 (together 3H, $NH_3^+$), 7.85–7.10 (8H, aromatic H), 4.50–4.10 (4H, 1×$CH_2$ and 2×CH), ca. 3.8–3.3 (2H, $CH_2$), 3.3–2.8 (3H, $CH_2$ and CH), 2.4–1.3 (4H, 2×$CH_2$), 1.20 (6H, 2×$CH_3$)

Example 42

Z-(D)-Phe(4-tBuO)-Pro-NH-pAmb

The hydroacetate was obtained by reacting Z-(D)-Phe(4-tBuO)OH as in Example 3. Melting point 92–104° C.

Example 43

H-(D)-Phe(4-tBuO)-Pro-NH-pAmb

The Z protective group was eliminated from Example 42 by hydrogenolysis using Pd/C as in A.I.b. The product was obtained as in dihydroacetate;
Melting point 94–102° C.

Example 44

Boc-(D,L)-Phe(4-tBu)-Pro-NH-pAmb

The hydroacetate was obtained by reacting Boc-(D,L)-Phe(4-tBu)OH as Example 3.
Melting point 151–158° C.

Example 45

H-(D,L)-Phe(4-tBu)-Pro-NH-pAmb

The hydrochloride was obtained by elimination of the Boc group from Example 44 as in A.I.c.
Melting point 96–110° C.

Example 46

H-(D,L)-Phe(4-Ph)-Pro-NH-pAmb

Boc-(D,L)-Phe(4-Ph)OH was converted into Boc-(D,L)-Phe(4-Ph)-Pro-NH-pAmb hydroacetate as in Example 3, and the Boc group was subsequently eliminated as in A.I.c.

$^1$H-NMR (DMSO-$d_6$, δ in ppm): 9.50–9.40 (2H, amidine), 9.30–9.20 (2H, amidine), 8.90 and 8.70 (together 1H, NH), 8.80 and 8.35 (together 3H, $NH_3^+$), 7.85–7.25 (13H, aromatic H), 4.50–4.15 (4H, 1×$CH_2$ and 2×CH), ca. 3.8–3.2 (2H, $CH_2$), 3.10–2.95 (2H, $CH_2$), 2.6–1.3 (4H, 2×$CH_2$)

Example 47

Boc-(D,L)-Phe(4-nBu)-Pro-NH-pAmb

Compound 47 was synthesized starting from Boc-(D,L)-Phe(4-Bu)-OH and H-Pro-p-cyanobenzylamide×HCl as in Example 3.

$^1$H-NMR ($d_6$-DMSO, δ in ppm): 10.0–9.2 (b, NH); 8.4/8.0 (2t, 1H, NH); 7.78 (2d, 2H, Ar—H); 7.42 (m, 3H, Ar—H); 7.25–7.0 (m, 4H, Ar—H/NH); 4.4–4.2 (m, 4H, CH2/α-Phe/α-Pro); 3.7–3.0 (m, 2H, δ-Pro/CH2); 3.0–2.6 (m, 4H, 2 CH2-Ph); 2.2–1.7 (m, 5H, β/γ-Pro); a,5 (m, 3H, β/γ-Pro/CH2); 1.25 (m, 9H, Boc); 0.95 (t, 3H, CH3)-(hydroacetate)

MS: 550 (M+H$^+$); 4,50 (−Boc); 247, 185, 134

Example 48

H-(D,L)-Phe(4-nBu)-Pro-NH-pAmb

The compound was prepared by elimination of Boc from Example 47. $^1$H-NMR ($d_6$-DMSO, δ in ppm): 9.4 (d, 2H, NH); 9.2 (d, 2H, NH); 8.9/8.6 (2t, 1H, NH); 7.75 (2d, 2H, Ar—H); 7.45 (d, 2H, Ar—H); 7.23 (d, 1H, NH); 7.15 (m, 4H, Ar—H); 4.4–4.2 (3m, 4H, CH2/2 α-H); 3.6 (m, 2H, γ-Pro/CH2); 3.1/2.9 (2m, 2H, CH2-Ph); 2.56/2.4 (2m, 2H, CH2); 2.1/1.9/1.6/1.3 (4m, 11H, β/γ-Pro/CH2); 0.95 (2t, 3H, CH3)

MS: 450 (M+H$^+$); 247, 176; Example 48 is in the form of the dihydroacetate.

Example 49

Boc-(D)-Phe(4-COOMe)-Pro-NH-pAmb a) Boc-(D)-Phe(4-COOMe)-Pro-NH-p-cyanobenzyl 12.5 g of Boc-(D)-Tyr(Bzl)OH were converted as in Example 3 into 18.9 g of Boc-(D)-Tyr(Bzl)-Pro-p-cyanobenzylamide, dissolved in 780 ml of MeOH and hydrogenated with Pd/C at room temperature. After 6 h, the catalyst was filtered off and the solvent was stripped off. Boc-(D)-Tyr-Pro-p-cyanobenzylamide was obtained in quantitative yield.

12.5 g of this compound were dissolved in 50 ml of pyridine and stirred at 0° C. with 4.7 ml of trifluoromethane-sulfonic anhydride for 1 h. After a further hour at room temperature, the mixture was poured into water and extracted with ethyl acetate. The organic phase was washed with water and dried over $Na_2SO_4$. 14 g of Boc-(D)-Tyr($SO_2CF_3$)-Pro-p-cyanobenzylamide were obtained. 4 g of the triflate were introduced into 1.93 ml of TEA, 134 mg of bisdiphenylphosphinopropane, 73 mg of Pd-II acetate, 1 ml of MeOH and 40 ml of DMF, and carbon monoxide was passed in at 60–70° C. until no more gas was absorbed. The mixture was poured into saturated brine and extracted with ethyl acetate. Washing the organic phase with 10% strength citric acid solution, drying over $Na_2SO_4$ and stripping off the solvent resulted in 3.3 g of Boc-(D)-Tyr(4-COOMe)-Pro-p-cyanobenzylamide.

b) Boc-(D)-Phe(4-COOMe)-Pro-NH-pAmb 1.7 g of the above nitrile were converted into the amidine hydroiodide as in Example 3. 650 mg were obtained after purification by column chromatography on silica gel.

$^1$H-NMR (DMSO-$d_6$, δ in ppm): 9.4–8.7 (4H, amidine), 8.9/8.1 (1H, NH (2 rotamers)), 7.9–7.2 (9H, aromatic B and NH), 3.85 (3H, COOMe), 1.3–1.2 (9H, Boc)

Example 50

H-(D)-Phe(4-COOMe)-Pro-NH-pAmb 1.3 g of the compound from Example 49 were converted into the amidine hydroacetate on an acetate ion exchanger, and the Boc group was eliminated as in A.I.c. 1.0 g of the product was obtained as dihydrochloride; melting point 204–207° C. (decomposition)

Example 51

H-(D)-Phe(4-$NO_2$)-Pro-NH-pAmb a) Boc-proline (p-amidinobenzyl)amide

Boc-Proline (p-cyanobenzyl)amide (see Example 5 for preparation) was converted as in the A.III.1 method into the thioamide using $H_2S$ and subsequently into the amidine. The amidine was obtained in the form of white crystals, melting point 237–239° C.

FAB-MS (M+H⁺)=347.

b) N-(p-Amidinobenzyl)prolinamide dihydrochloride

The Boc protective group was eliminated from the above compound as in A.I.c. The dihydrochloride was isolated as a very hygroscopic powder, melting point 130 to 140° C. FAB-MS (M+H⁺)=247.

c) Boc-(D)-Phe(4-NO$_2$)-Pro-NH-pAmb

A solution of 3.9 g (12.6 mmol) of Boc-(D)-Phe(4-NO$_2$) OH in 40 ml of THF was stirred at room temperature for 4 h after addition of 1.9 g (12.6 mmol) of 1-hydroxybenzotriazole and 3.3 g (25 mmol) of dicyclohexylcarbodiimide. The precipitated urea was filtered off with suction and washed with a little THF.

A solution of 4.1 g (12.6 mmol) of N-(p-amidinobenzyl) prolinamide dihydrochloride and 1.6 g of sodium bicarbonate in 6 ml of water was added to this filtrate at 5° C. After stirring at room temperature for 48 h, the solvent was substantially removed by distillation, the residue was taken up in ethanol, insolubles were removed by filtration, and the solution was again concentrated.

The residue was purified on a silica gel column with a CH$_2$Cl$_2$MeOH/50% strength acetic acid mixture (45/5/1.5). The eluate of the pure fractions was distilled off, adding toluene towards the end, and the residue was recrystallized from 50 ml of acetone with the addition of a little water. 3.3 g (48% of theory) of amidine acetate were isolated in the form of white crystals, melting point 162 to 165° C. FAB-MS:=539.5 (M+H⁺)

d) H-(D)-Phe(4-NO$_2$)-Pro-NH-pAmb

The Boc group was eliminated as in A.I.c. Dihydrochloride: white crystals, melting point 218–225° C. (decomposition), FAB-MS: 439 (M+H⁺).

Example 52

Boc-(D,L)-Phe(3-F)-Pro-NH-pAmb

The compound was prepared starting from Boc-(D,L)-Phe(3-F)-OH and H-Pro-p-cyanobenzylamide×HCl as in Example 3.

$^1$H-NMR (d$_6$-DMSO, δ in ppm): 9.4–9.0 (b, N—H); 8.9/8.4/8.15 (3t, 1H, NH); 7.8 (sb, 2H, Ar—H); 7.45 (2d, 2H, Ar—H); 7.35–6.9 (2m, 5H, Ar—H/NH); 4.5–4.2 (m, 4H, NCH2/α-Phe/α-Pro); 3.7/3.5/3.2 (3m, 2H, δ-Pro); 3.0–2.7 (2m, 2H, Ar—CH2); 2.2–1.7 (3m, 4H, β/γ-Pro); 1.25 (2s, 9H, Boc)

FAB-MS: 511 (M+H⁺)

Example 53

H-(D,L)-Phe(3-F)-Pro-NH-pAmb

The compound was prepared by elimination of Boc from Example 52.

$^1$H-NMR (d$_6$-DMSO, δ in ppm): 9.4/9.2 (2d, 4H, N—H); 8.9/8.55 (1H, NH); 8.75/8.3 (2sb, 3H, NH3); 7.8 (sb, 2H, Ar—H); 7.45 (2d, 2H, Ar—H); 7.4–7.05 (m, 4H, Ar—H); 4.45–4.2 (m, 4H, NCH2/α-Phe/α-Pro); 3.9–3.3 (2H, δ-Pro); 3.2–2.8 (m, 2H, Ar—CH2); 2.2–1.8 (4H, β/γ-Pro)

FAB-MS: 411 (M+H⁺)-(dihydrochloride)

Example 54

Boc-(D,L)-Phe(3-Cl)-Pro-NH-pAmb

The hydroacetate was prepared from Boc-(D,L)-Phe(3-Cl)OH as in Example 3;

$^1$H-NMR (d$_6$-DMSO, δ in ppm): 9.4–8.6 (4H, amidine), 8.45/8.15 (1H, NH), 7.8–7.0 (9H, aromatic H and NH), 1.3–1.2 (9H, Boc)

Example 55

H-(D,L)-Phe(3-Cl)-Pro-NH-pAmb

The Boc group was cleaved off 54 as in A.I.c. The product was obtained as dihydrochloride.

$^1$H-NMR (d$_6$-DMSO, δ in ppm): 9.5–9.2 (4H, amidine), 8.95 (1H, NH), 8.8/8.4 (3H, NH$_3^+$), 7.9–7.2 (8H, aromatic H), 4.50–4.15 (4H, CH$_2$ and 2×CH), 3.8–ca. 3.3 (2H, CH$_2$), 3.25–2.95 (2H, CH$_2$), 2.2–1.5 (4H, 2×CH$_2$)

Example 56

H-(D,L)-Phe(3-OH)-Pro-NH-pAmb

The compound was prepared by elimination of Boc from Boc-(D,L)-Phe(3-OH)-Pro-NH-pAmb.

$^1$H-NMR (d$_6$-DMSO, δ in ppm): 9.6/9.0 (mb/N—H); 8.8/8.5 (2t, 1H, NH); 8.2 (sb, N—H); 7.8 (2d, 2H, Ar—H); 7.5 (2d, 2H, Ar—H); 7.1 (m, 1H, Ar—H); 6.8–6.6 (m, 3H, Ar—H), 4.4–4.1 (m, 4H, CH2/2 α-H); 3.8–3.6 (m, 2H, Pro); 3.0/2.8 (2m, 2H, CH2); 2.1–1.5 (m, 4H, β/γ-Pro)

FAB-MS: 410 (M+H⁺; mp: 168° C. (decomp.)-(dihydroacetate)

Example 57

Boc-(D,L)-Phe(3-MeO)-Pro-NH-pAmb

The hydroacetate was prepared from Boc-(D,L)-Phe(3-MeO)OH as in Example 3 $^1$H-NMR (d$_6$-DMSO, δ in ppm): 9.4–8.7 (4H, amidine), 8.4/8.1 (1H, NH), 7.8–6.7 (9H, aromatic H and NH), 3.7 (3H, OCH$_3$, 1.3–1.2 (9H, Boc)

Example 58

H-(D,L)-Phe(3-MeO)-Pro-NH-pAmb

The Boc group was cleaved off 57 as in A.I.c. The product was obtained as dihydrochloride.

$^1$H-NMR (DMSO-d$_6$, δ in ppm): 9.55–9.15 (4H, amidine), 8.9/8.7 (1H, NH), 8.75/8.30 (3H, NH$_3^+$), 7.9–6.7 (8H, aromatic H), 4.5–4.1 (4N, CH$_2$ and 2×CH), 3.75/3.72 (3H, OCH$_3$), 3.3–2.9 (2H, CH$_2$), 2.2–1.4 (4H, 2×CH$_2$)

Example 59

Boc-(D,L)-Phe(3-PhO)-Pro-NH-pAmb

The compound was prepared from Boc-(D,L)-Phe(3-PhO)OH. The amidine hydroacetate was obtained as in Example 3.

Example 60

H-(D,L)-Phe(3-PhO)-Pro-NH-pAmb

The dihydrochloride was obtained by elimination of Boc from Example 59.

$^1$H-NMR (d$_6$-DMSO, δ in ppm): 9.5–9.2 (4H, amidine), 8.9/~8.2 (1H, NH), 8.75/8.35 (3H, NH$_3^+$), 7.85–6.80 (8H, aromatic H), 4.50–4.10 (4H, CH$_2$ and 2×CH), 3.8–2.9 (4H, 2×CH$_2$), 2.8–1.5 (4H, CH$_2$)

Example 61

Boc-(D,L)-Phe(3-Me)-Pro-NH-pAmb

The compound was prepared starting from Boc-(D,L)-Phe(3-Me)-OH and B-Pro-p-cyanobenzylamide×HCl as in Example 3.

¹H-NMR (d₆-DMSO, δ in ppm): 8/8.4/8.05 (3t, 1H, NH); 7.74 (2d, 2H, Ar—H); 7.45 (2d, 2H, Ar—H); 7.2–6.9 (m, 5H, Ar—H/NH); 4.4–4.2 (m, 4H, NCH2/α-Pro/α-Phe); 3.7–3.1 (2m, 2H, δ-Pro); 2.9–2.7 (2H, Ar—CH2); 2.5 (2s, 3H, CH3); 2.1–1.6 (m, 4H, β/γy-Pro); 1.25 (2s, 9H, Boc)
MS: 508 (M+H⁺), 408 (–Boc), 277, 247-(hydroacetate)

Example 62

H-(D,L)-Phe(3-Me)-Pro-NH-pAmb

The compound was prepared by elimination of Boc from Example 61. MS: 408 (M+H⁺), 247, 185, 134, 93-(dihydroacetate)

Example 63

H-(D,L)-Phe(3-Ph)-Pro-NH-pAmb

The corresponding Boc-protected compound was prepared as in Example 3 from Boc-(D,L)-Phe(3-Ph)OH and subsequently cleaved to the dihydrochloride as in A.I.c.
¹H-NMR (DMSO-d₆, δ in ppm): 9.5–9.2 (4H, amidine), 8.9/ca. 8.7 (1H, NH), 8.8/8.35 (3H, NH₃⁺), 7.85–7.25 (13H, aromatic H), 4.5–4.15 (4H, CH₂ and 2×CH), 3.2–3.00 (2H, CH₂), 2.2–1.4 (4H, 2×CH₂)

Example 64

Boc-(D,L)-Phe(3-CF₃)-Pro-NH-pAmb

The compound was prepared starting from Boc-(D,L)-Phe(3-CF₃)—OH and H-Pro-p-cyanobenzylamide×HCl as in Example 3. ¹H-NMR (d₆-DMSO, δ in ppm): 10.0–9.2 (b, NH); 8.9/8.4/8.15 (3t, 1H, NH); 7.8–7.4 (8H, Ar—H); 7.22/7.05 (2d, 1H, NH); 4.6–4.2 (4H, N—CH2/α-Pro/α-H); 3.8–3.4 (2H, δ-Pro); 3.1/2.8 (2H, Ar—CH2); 2.1–1.6 (4H, β/γ-Pro); 1.2 (2s, 9H, Boc) MS: 562 (M+H⁺), 462 (–Boc), 247, 188, 134-(hydroacetate)

Example 65

H-(D,L)-Phe(3-CF₃)-Pro-NH-pAmb

The compound was prepared by elimination of Boc from Example 64. ¹H-NMR (d₆-DMSO, δ in ppm): 9.4 (2s, 2H, NH); 9.2 (2s, 2H, NH); 8.9/8.8 (2t, 1H, NH); 8.8/8.6/8.4 (3sb, 3H, NH3); 7.8–7.4 (8H, Ar—H); 4.42–4.1 (4H, N—CH2/α-Pro/α-H); 3.8 (m 1H, δ-Pro/Ar—CH2); 2.2–1.5 (4H, β/γ-Pro) Melting point 195–7° C.-(dihydroacetate)

Example 66

Boc-(D,L)-Phe(2-F)-Pro-NH-pAmb

The compound was prepared starting from Boc-(D,L)-Phe(2-F)—OH and H-Pro-NH-pCNb×HCl as in Example 3.
¹H-NMR (d₆-DMSO, δ in ppm): 9.8–9.2 (b, N—H); 8.5/8.2 (2t, 1H, NH); 7.75 (2d, 2H, Ar—H); 7.45 (2d, 2H, Ar—H); 7.4–7.0 (m, 5H, Ar—H/NH); 4.6–4.2 (m, 4H, NCH2/α-Phe/α-Pro); 3.6–3.0 (4m, 2H, δ-Pro); 2.9–2.7 (2m, 2H, Ar—CH2); 2.2–1.7 (3m, 4H, β/γ-Pro); 1.2 (2s, 9H, Boc) MS: 512 (M+H⁺), 412 (–Boc), 247, 134-(hydroacetate)

Example 67

H-(D,L)-Phe(2-F)-Pro-NH-pAmb

The compound was prepared by elimination of Boc from Example 66. ¹H-NMR (d₆-DMSO, δ in ppm): 9.4 (2s, 2H, N—H); 9.15 (2s, 2H, N—H), 8.9/8.6 (2sb, 3H, NH); 7.8 (2d, 2H, Ar—H); 7.45 (2d, 2H, Ar—H); 7.4–7.1 (m, 4H, Ar—H); 4.5–4.2 (3m, 4H, NCH2/α-Phe/α-Pro); 3.6–3.2 (2m, 2H, δ-Pro); 3.0/2.7 (2m, 2H, Ar—CH2); 2.2–1.5 (5m, 4H, β/γ-Pro) MS 412 (M+H⁺), 247, 134-(dihydrochloride)

Example 68

Boc-(D,L)-Phe(2-Cl)-Pro-NH-pAmb

The hydroacetate was prepared from Boc-(D,L)-Phe(2-Cl)—OH as in Example 3.

Example 69

H-(D,L)-Phe(2-Cl)-Pro-NH-pAmb

The dihydrochloride was obtained from Example 68 as in A.I.c. ¹H-NMR (d₆-DMSO, δ in ppm): 9.5–9.2 (4H, amidine), 8.9/8.7 (1H, NH); 8.85/8.45 (3H, NH₃⁺), 7.9–7.2 (8H, aromatic H), 4.5–4.1 (4H, CH₂ and 2×CH), 3.8–3.0 (4H, 2×CH₂), 2.2–1.4 (4H, 2×CH₂)

Example 70

Boc-(D,L)-Phe(2OH)-Pro-NH-pAmb

The compound was prepared starting from Boc-(D,L)-Phe(2-OH)—OH and H-Pro-p-cyanobenzylamide×HCl as in Example 3. ¹H-NMR (d₆-DMSO, δ in ppm): 8.4/8.0 (2t, 1H, NH); 7.7 (2d, 2H, Ar—H); 7.4 (2d, 2H, Ar—H); 7.2/7.15 (2d, 1H, NH); 7.0–6.6 (4H, Ar—H); 4.45–4.2 (m, 4H, H—CH2/α-Pro/α-H); 3.8–3.2 (2H, δ-Pro); 3.0/2.8 (2m, 2H, Ar—CH2); 2.1–1.6 (4H, β/γ-Pro); 1.2 (2s, 9H, Boc) MS: 510 (M+H⁺), 410 (–Boc), 247, 134-(hydroacetate)

Example 71

H-(D,L)-Phe(2-OH)-Pro-NH-pAmb

The compound was prepared by elimination of Boc from Example 70. ¹H-NMR (d₆-DMSO, δ in ppm): 9.4–9.0 (b, NH); 8.85/8.5 (2t, 1H, NH); 7.8 (2d, 2H, Ar—H); 7.5 (2d, 2H, Ar—H); 7.2–6.7 (4H, Ar—H); 4.4–3.7 (m, 4H, N—CH2/α-Pro/α-H); 3.4–3.2 (2H, δ-Pro); 3.1–2.75 (2H, Ar—CH2); 2.1–1.4 (4H, β/γ-Pro) MS: 410 (M+H⁺), 369, 277, 247-(dihydroacetate)

Example 72

Boc-(D,L)-Phe(2-MeO)-Pro-NH-pAmb

The hydroacetate was obtained from Boc-(D,L)-Phe(2-MeO)OH as in Example 3.

Example 73

H-(D,L)-Phe(2-MeO)-Pro-NH-pAmb

The dihydrochloride was obtained from Example 72 as in A.I.c. ¹H-NMR (d₆-DMSO, δ in ppm): 9.55–9.25 (4H, amidine), 8.90/8.65 (1H, NH); 8.7/8.2 (3H, NH₃⁺), 7.9–6.8 (8H, aromatic H), 4.5– 4.1 (4H, CH₂ and 2×CH), 3.80 (3H, OCH₃), –3.8–3.3 (2H, CH₂), 3.2–2.6 (2H, CH₂), 2.2–1.4 (4H, 2×CH₂)

Example 74

Boc-(D,L)-Phe(2-Me)-Pro-NH-pAmb

The compound was prepared starting from Boc-(D,L)-Phe(2-Me)-OH and H-Pro-p-cyanobenzylamide×HCl as in Example 3. ¹H-NMR (d₆-DMSO, δ in ppm): 8.4/8.05 (2t, 1H, NH); 7.75 (2d, 2H, Ar—H); 7.4 (2d, 2H, Ar—H); 7.2–7.0 (m, 5H, Ar—H)/NH); 4.6–4.2 (m, 4H, CH2/2 α-H); 3.7–3.55 (2m, 2H, δ-Pro); 3.0–2.6 (m, 2H, CH2); 2.3 (2s, 3H, CH3); 2.2–1.6 (m, 4H, β/γ-Pro); 1.35–1.2 (1s, 9H, Boc) FAB-MS: 508 (M+H$^+$)-(hydroacetate)

Example 75

H-(D,L)-Phe(2-Me)-Pro-NH-pAmb

The compound was prepared by elimination of Boc from Example 74. $^1$H-NMR (d$_6$-DMSO, δ in ppm): 9.35 (s, 2H, N—H); 9.05 (s, 2H, N—H); 8.8/8.5 (2t, 1H, NH); 7.8/7.75 (2d, 2H, Ar—H); 7.5/7.45 (2d, 2H, Ar—H); 7.2–7.0 (m, 4H, Ar—H); 4.4–4.2 (3m, 4H, CH2/2 α-H); 3.6/0.3 [sic] (2m, 2H, δ-Pro); 3.1/3.0 (2m, 2H, CH2); 2.38 (m, 3H, CH3); 2.2–1.3 (4H, β/γ-Pro) MS: 408 (M+H$^+$), 247, 185, 134-(dihydrochloride)

Example 76

Boc-(D,L)-Phe(2-iPr)-Pro-NH-pAmb

The hydroacetate was prepared from Boc-(D,L)-Phe(2-iPr)OH as in Example 3.

Example 77

H-(D,L)-Phe(2-iPr)-Pro-NH-pAmb

The dihydrochloride was obtained from Example 76 as in A.I.c. Melting point 220–221° C.

Example 78

Boc-(D,L)-Phe(2-Ph)-Pro-NH-pAmb

The hydroacetate was prepared from Boc-(D,L)-Phe(2-Ph)OH as in Example 3.

Example 79

H-(D,L)-Phe(2-Ph)-Pro-NH-pAmb

The dihydrochloride was obtained from Example 78 as in A.I.c. $^1$H-NMR (DMSO-d$_6$, δ in ppm): 9.5–9.2 (4H, amidine), 8.85/8.67 (1H, NH), 8.6/8.2 (3H, NH$_3^+$), 7.85–7.15 (13H, aromatic H), 4.4–3.0 (8H, 3×CH$_2$ and 2×CH), 2.2–1.4 (4H, 2×CH$_2$)

Example 80

Boc-(D,L)-Phe(3,4-(F)$_2$)-Pro-NH-pAmb

The hydroacetate was prepared from Boc-(D,L)-Phe(3,4-(F)$_2$)OH (J. Med. Chem. 1967, 10, 64) as in Example 3; white crystals; melting point 110–114° C.; FAB-MS: 530 (M+H$^+$)

Example 81

H-(D,L)-Phe(3,4-(F)$_2$)-Pro-NH-pAmb

The dihydrochloride was obtained from Example 80 by elimination of Boc as in A.I.c.; white crystals; melting point 190–195° C. (decomposition); FAB-MS: 430 (M+H$^+$)

Example 82

Boc-(D,L)-Phe(3,4-(Cl)$_2$)-Pro-NH-pAmb

The hydroacetate was obtained by reacting Boc-(D,L)-Phe(3,4-(Cl)$_2$)—OH (Int. J. Pept. Protein Res. 1987, 30, 13) as in Example 3; white crystals; melting point 135–138° C.; FAB-MS: 562 (M+H$^+$)

Example 83

H-(D,L)-Phe(3,4-(Cl)$_2$)-Pro-Ng-pAmb

The dihydrochloride was obtained from Example 82 by Boc elimination as in A.I.c.; white crystals; melting point 208–212 C.; FAB-MS: 462 (M+H$^+$)

Example 84

Boc-(D,L)-Phe(3-Cl-4-MeO)-Pro-NH-pAmb

The hydroacetate was prepared from Boc-(D,L)-Phe(3-Cl-4-MeO)OH as in Example 3.

Example 85

H-(D,L)-Phe(3-Cl-4-MeO)-Pro-NH-pAmb

The dihydrochloride was obtained from Example 84 by Boc elimination as in A.I.c. $^1$H-NMR (DMSO-d$_6$, δ in ppm): 9.58–9.30 (4H, amidine), 8.98/8.85 (1H, NH), 8.8/8.35 (3H, NH$_3^+$), 7.9–7.0 (7H, aromatic H), 4.50–4.20 (4H, CH$_2$ and 2×CH), 3.85/3.82 (3H, OCH$_3$), 3.2–2.9 (2H, CH$_2$), 2.2–1.5 (4H, 2×CH$_2$)

Example 86

Boc-(D,L)-Phe(3-Cl, 4-OEt)-Pro-NH-pAmb

The compound was prepared as hydroacetate starting from Boc-(D,L)-Phe(3-Cl, 4-OEt)-OH and H-Pro-p-cyanobenzylamide×HCl as in Example 3. FAB-MS: 573 (M+H$^+$)

Example 87

H-(D,L)-Phe(3-Cl, 4-OEt)-Pro-NH-pAmb

The compound was prepared as dihydrochloride by elimination of Boc from Example 86. $^1$H-NMR (d$_6$-DMSO, δ in ppm): 9.4 (d, 2H, NH); 9.2 (d, 2H, NH); 8.9/8.7 (2t, 1H, NH); 8.4–8.2 (b, 3H, NH3); 7.8 (2d, 2H, Ar—H); 7.45 (2d, 2H, Ar—H); 7.3 (m, 1H, Ar—H); 7.2/7.0 (2H, Ar—H); 4.5–4.2 (4H, N—CH2/α-Pro/α-Phe); 4.1 (m, 2H, OCH2); 3.7–3.1 (m, 2H, δ-Pro); 3.1–2.7 (m, H, Ar—CH2); 2.2–1.6 (m, 4H, β/γ-Pro); 1.35 (q, 3H, CH3) MS: 472 (M+H$^+$), 247, 134; 70

Example 88

H-(D,L)-Phe(3,4-(MeO)$_2$)-Pro-NH-pAmb

The corresponding Boc-protected compound was prepared as in Example 3 from Boc-(D,L)-Phe(3,4-(MeO)$_2$)OH and subsequently cleaved to give the dihydrochloride as in A.I.c. $^1$H-NMR (DMSO-d$_6$, δ in ppm): 9.55–9.25 (4H, amidine), 8.95/ca. 8.8 (1H, NH), 8.8/8.35 (3H, NH$_3^+$) 7.9–6.7 (7H, aromatic H), 4.50–4.15 (4H, CH$_2$ and 2×CR), 3.75–3.68 (6H, 2×OCH$_3$), 3.2–2.8 (2H, CH$_2$, 2.2–1.4 (4H, 2×CH$_2$)

Example 89

Boc-(D,L)-Phe(3,4-(Me)$_2$)-Pro-NH-pAmb

The hydroacetate was prepared from Boc-(D,L)-Phe(3,4-(Me)$_2$)OH as in Example 3; white crystals; melting point 108–112° C.; FAB-MS: 522 (M+H$^+$)

Example 90

H-(D,L)-Phe(3,4-(Me)$_2$)-Pro-NH-pAmb

The dihydrochloride was obtained from Example 89 by Boc elimination as in A.I.c.; white crystals; melting point 195–200° C.; FAB-MS: 422 (M+H$^+$)

Example 91

Boc-(D,L)-Phe(3-Me-4-iPr)-Pro-NH-pAmb

The hydroacetate was prepared from Boc-(D,L)-Phe(3-Me-4-iPr)OH as in Example 3.

Example 92

H-(D,L)-Phe(3-Me-4-iPr)-Pro-NH-pAmb

The dihydrochloride was obtained from Example 91 by Boc elimination as in A.I.c. $^1$H-NMR (DMSO-d$_6$, δ in ppm): 9.5–9.2 (4H, amidine), 8.9/9.6 (1H, NH), 8.85/8.40 (3H, NH$_3^+$), 7.9–6.85 (7H, aromatic H), 4.5–4.0 (4H, CH$_2$ and 2×CH), 3.2–2.9 (2H, CH$_2$), 2.32/2.30 (3H, CH$_3$), 2.2–1.4 (4H, 2×CH$_2$), 1.2–1.1 (6H, 2×CH$_3$)

Example 93

Boc-(D,L)-Phe(2,3-(MeO)$_2$)-Pro-NH-pAmb

The hydroacetate was prepared from Boc-(D,L)-Phe(2,3-(MeO)$_2$)OH as in Example 3.

Example 94

H-(D,L)-Phe(2,3-(MeO)$_2$)-Pro-NH-pAmb

The dihydrochloride was obtained from Example 93 by Boc elimination as in A.I.c. The 1.3:1 mixture of diastereomers showed a melting range of 138–140° C. (decomposition).

Example 95

Boc-(D,L)-Phe(2,5-(MeO)$_2$)-Pro-NH-pAmb

The hydroacetate was prepared from Boc-(D,L)-Phe(2,5-(MeO)$_2$)OH as in Example 3.

Example 96

H-(D,L)-Phe(2,5-(MeO)$_2$)-Pro-NH-pAmb

The dihydrochloride was obtained from Example 95 by Boc elimination as in A.I.c. $^1$H-NMR (DMSO-d$_6$, δ in ppm): 9.55–9.25 (4H, amidine), 8.95/ca. 8.7 (1H, NH), 8.7/8.2 (3H, NH$_3^+$), 7.9–7.4 and 7.0–6.7 (7H, aromatic H), 4.50–4.1 (4H, CH$_2$ and 2×CH), 3.8/3.7 (6H, 2×OCH$_3$), 3.25–2.65 (2H, CH$_2$), 2.2–1.5 (4H, 2×CH$_2$)

Example 97

Boc-(D,L)-Phe(3,5-(MeO)$_2$)-Pro-NH-pAmb

The hydroacetate was prepared from Boc-(D,L)-Phe(3,5-(MeO)$_2$)OH as in Example 3.

Example 98

H-(D,L)-Phe(3,5-(MeO)$_2$)-Pro-NH-pAmb

The dihydrochloride was obtained from Example 97 by Boc elimination as in A.I.c. $^1$H-NMR (DMSO-d$_6$, δ in ppm): 9.5–9.2 (4H, amidine), 8.95/ca. 8.7 (1H, NH), 8.7/8.3 (3H, NH$_3^+$), 7.85–7.40 and 6.60–6.35 (7H, aromatic H), 4.50–4.15 (4H, CH$_2$ and 2×CH), 3.75/3.72 (6H, 2×OCH$_3$), 3.2–2.8 (2H, CH$_2$), 2.2–1.4 (4H, 2×CH$_2$)

Example 99

Boc-(D,L)-Phe(3,4,5-(MeO)$_3$)-Pro-NH-pAmb

Preparation took place as in Example 3, preparing the precursor Boc((D,L)-Phe(3,4,5-(MeO)$_3$)OH by alkylation of benzophenone imine glycine ester with trimethoxybenzyl chloride, subsequent introduction of Boc-protective groups and ester hydrolysis. Melting point 109–121° C. (dihydroacetate)

Example 100

H-(D,L)-Phe(3,4,5-(MeO)$_3$)-Pro-NH-pAmb

Prepared from Example 99. Melting point 180–239° C. (dihydrochloride)

Example 101

Boc-(D,L)-Phe(2,4,6-(Me)$_3$)-Pro-NH-pAmb

The hydroacetate was prepared from Boc-(D,L)-Phe(2,4,6-(Me)$_3$)OH as in Example 3.

Example 102

H-(D,L)-Phe(2,4,6-(Me)$_3$)-Pro-NH-Amb

The dihydrochloride was obtained from Example 101 by Boc elimination as in A.I.c. $^1$H-NMR (DMSO-d$_6$, δ in ppm): 9.5–9.15 (4H, amidine), 8.85/ca. 8.7 (1H, NH), 8.8/8.5 (3H, NH$_3^+$), 7.9–7.4 and 6.9–6.75 (6H, aromatic H), 4.5–4.0 (4H, CH$_2$ and 2×CH), ca. 3.7–3.3 (2H, CH$_2$), 3.2–3.0 (2H, CH$_2$), 2.25–2.10 (6H, 3×CH$_3$), ca. 2.1–1.4 (4H, 2×CH$_2$)

Example 103

Boc-(D)-α-Nal-Pro-NH-pAmb

Preparation took place as in Example 3. Melting point 136–178° C. (hydroacetate)

Example 104

H-(D)-α-Nal-Pro-NH-pAmb

Prepared from Example 103. Melting point 228–234° C. (dihydrochloride)

Example 105

H-(D)-β-Nal-Pro-NH-pAmb

Prepared from Boc-(D)-β-Nal-Pro-NH-pAmb by Boc elimination; melting point 223–229° C. (dihydrochloride)

Example 106

Boc-(D,L)-α-Ngl-Pro-NH-pAmb

The compound was prepared starting from Boc-(D,L)-α-Ngl-OH and H-Pro-p-cyanobenzylamide×HCl as in Example 3. $^1$H-NMR (d$_6$-DMSO, δ in ppm): 10.0 (b, NH); 8.7/8.5 (2t, 1H, NH); 8.3–7.3 (12H, Ar—H/NH); 6.2/6.1 (2d, 1H, α-Ngl); 4.4 (3H, N—CH2/α-Pro); 3.8–2.8 (2H, δ-Pro); 2.2–1.7 (4H, β/γ-Pro); 1.3 (2s, 9H, Boc) MS: 530 (M+H$^+$), 430 (−Boc), 247, 134; mp: 183–5° C. (decomp.)-(hydroacetate)

Example 107

H-(D,L)-α-Ngl-Pro-NH-pAmb

The compound was prepared by elimination of Boc from Example 106. $^1$H-NMR (d$_6$-DMSO, δ in ppm): 9.5/9.3 (2d, 4H, NH); 9.0/8.8 (2t, 1H, NH); 8.7 (b, 3H, NH3); 8.4 (m, 1H, Ar—H); 8.1 (2d, 2H, Ar—H); 7.9 (2d, 2H, Ar—H); 7.7–7.7 (6H, Ar—H); 6.25/6.18 (2s, 1H, α-Ngl); 4.6–4.35 (m, 3H, N—CH2/α-Pro); 3.85/3.6/3.4 (3m, 2H, δ-Pro); 2.2–1.6 (4H, β/γ-Pro) MS: 430 (M+H$^+$), 3.69 [sic], 277-(dihydrochloride)

Example 108

Boc-(D,L)-β-Ngl-Pro-NH-pAmb

The compound was prepared starting from Boc-(D,L)-β-Ngl-OH and H-Pro-p-cyanobenzylamide×HCl as in Example 3. $^1$H-NMR (d$_6$-DMSO, δ in ppm): 9.8–9.2 (b, NH); 8.6/8.4 (2sb, 1H, NH); 8.0–7.75 (6H, Ar—H); 7.6–7.5 (5H, Ar—H); 7.35/7.18 (2sb, 1H, NH); 5.6/5.45/5.35 (3sb, 1H, α-Ngl); 4.4 (3H, N—CH2/α-Pro); 3.9/3.7 (2sb, 1H, δ-Pro); 3.2 (sb, 1H, δ-Pro); 2.2–1.85 (4H, β/γ-Pro); 1.4 (2s, 9H, Boc) MS: 530 (M+H$^+$), 430 (–Boc), 2.47 [sic], 185, 134; melting point 183–5° C. (decomp.)-(hydroacetate)

Example 109

H-(D,L)-β-Ngl-Pro-NH-pAmb

The compound was prepared as dihydroacetate by elimination of Boc from Example 108. $^1$H-NMR (d$_6$-DMSO, δ in ppm): 9.6–9.0 (b, NH); 8.75/8.6 2t, 1H, NH); 8.0–7.8 (6H, Ar—H); 7.6–7.4 (m, 5H, Ar—H); 5.2 (s, 1H, α-Ngl); 4.5–4.3 (m, 3H, N—CH2/α-Pro); 3.9–3.0 (2H, δ-Pro); 2.2–1.7 (4H, β/γ-Pro) MS: 430 (M+H$^+$), 247

Example 110

H-(D,L)-1-Tic-Pro-NH-pAmb

The compound was prepared as dihydroacetate starting from Example 255 by Boc elimination. $^1$H-NMR (d$_6$-DMSO, δ in ppm): 9.4/9.0 (2sb, 4H, NH); 8.7 (b, 1H, NH); 7.75 (2d, 2H, Ar—H); 7.45 (2d, 2H, Ar—H); 7.4–6.8 (4H, Ar—H); 5.2 (2s, 1H, α-Tic); 4.8–4.4 (3H, N—CH2/α-Pro); 3.6–3.2 (4H, Ar—CH2/δ-Pro); 3.0–2.7 (2H, N—CH2); 2.2–1.8 (4H, β/γ-Pro)

Example 111

Boc-(D)-3-Tic-Pro-NH-pAmb

The compound was prepared starting from Boc-(D)-3-Tic-PH [sic] and H-Pro-p-cyanobenzylamide×HCl as in Example 3. $^1$H-NMR (d$_6$-DMSO, δ in ppm): 8.44/8.2 (2sb, 1H, NH); 7.8/7.65 (2d, 2H, Ar—H); 7.5 (2d, 2H, Ar—H); 7.4/7.2 (m, 4H, Ar—H); 4.8–4.6 (m, 2H, CH2); 4.4–4.2 (m, 4H, CH2/2 α-H); 3.62 (m, 2H, Pro); 3.1–2.6 (m, 2H, CH2-Ph); 2.2–1.75 (m, 4H, Pro); 1.3 (2s, 9H, Boc) MS: 506 (M+H$^+$); 406 (–Boc); melting point 143° C.-(hydroacetate)

Example 112

H-(D)-3-Tic-Pro-NH-pAmb

The compound was prepared by elimination of Boc from Example 111. FAB-MS: 406 (M+H$^+$): melting point 204° C.-(dihydroacetate)

Example 113

1-Icc-Pro-NH-pAmb

The compound was prepared starting from 1-Icc-OH and H-Pro-p-cyanobenzylamide×HCl as in Example 3. FAB-MS: 402 (M+H$^+$)

Boc-(D,L)-2-Tgl-Pro-NH-pAmb

The compound was prepared as hydroacetate starting from Boc-(D,L)-2-Tgl-OH and H-Pro-p-cyanobenzylamide×HCl as in Example 3. $^1$H-NMR (d$_6$-DMSO, δ in ppm): 8.6(8.4 (2t, 1H, NH); 7.75 (2d, 2H, Ar—H); 7.45–6.9 (6H, Ar—H); 5.7–5.4 (1H, a-Tgl); 4.4 (m, 3H, N—CH$_2$/α-Pro); 3.8–3.2 (2H, δ-Pro); 2.1–1.7 (4H, β/γ-Pro); 1.35 (2s, 9H, Boc) MS: 486 (M+H$^+$), 386 (–Boc), 247, 185, 134

Example 115

H-(D,L)-2-Tgl-Pro-NH-pAmb

The compound was prepared by elimination of Boc from Example 114. IH-NMR (d$_6$-DMSO, δ in ppm): 9.4/9.2 (2sb,4H, NH); 8.9/8.75 (2t, 1H, NH); (sb, 3H, NH); 7.8 (2d, 2H, Ar—H); 7.62 (2d, 2H, Ar—H); 7.5 (2d, 2H, Ar—H); 7.4, sb, 1H, Ar—H; 7.1 (m, 1H, Ar—H); 5.65/5.6 (2s, 1H, α-Tgl); 4.5–4.4 (m, 3H, N—CH$_2$/α-Pro); 3.95–3.75 (2m, 1H, δ-Pro); 3.2/3.0 (2dd, 1H, 5-Pro); 2.2–2.0 (1H, β-Pro); 1.9–1.7 (3H, β/γ-Pro) FAB-MS: 386 (M+H$^+$)-(dihydroacetate)

Example 116

Boc-(D)-2-Tal-Pro-NH-pAmb

The compound was prepared starting from Boc-(D)-2-Tal-OH and H-Pro-p-cyanobenzylamide×HCl as in Example 3. $^1$H-NMR (d$_6$-DMSO, δ in ppm): 8.85/8.15 (2t, 1E, NH); 7.75 (2d, 2H, Ar—H); 7.45 (2d, 2H, Ar—H); 7.35 (d, 1H, Ar—H); 7.25 (sb, 1H, Ar—H); 7.0–6.7 (2H, Ar—H); 4.82–4.3 (4H, N—CH$_2$/α-Pro/α-Tal); 4.05/3.6 (2m, 1H, δ-Pro); 3.5–2.9 (m, 3H, Ar—CH$_2$/δ-Pro); 2.2–1.7 (4H, β/γ-Pro); 1.25 (2s, 9H, Boc) MS: 500 (M+H$^+$), 400 (–Boc), 247, 134-(hydroacetate)

Example 117

H-(D-)-2-Tal-Pro-NH-pAmb

The compound was prepared by elimination of Boc from Example 116. $^1$H-NMR (d$_6$-DMSO, δ in ppm): 9.4–9.0 (4H, NH); 8.85 (b, 3H, NH$_3$); 7.8 (d, 2H, Ar—H); 7.5 (d, 2H, Ar—H); 7.45 (d, 1H, Ar—H); 7.0 (dd(s, 2H, Ar—H); 4.4–4.15 (4H, N—CH$_2$//α-Pro/α-Tal); 3.8–2.9 (3H, Ar—CH/δ-Pro); 2.8 (dd, Ar—H); 1.8 (m, 2H, β-Pro); 1.75–1.55 (2m, 2H, γ-Pro) FAB-MS: 400 (M+H$^+$)-(dihydroacetate)

Example 118

Boc(D)-Phg-Pro-NH-pAmb

The hydroacetate was prepared from Boc-(D)-Phg-OH as in Example 3.

Example 119

H-(D)-Phg-Pro-NH-pAmb

The dihydrochloride was obtained from Example 118. $^1$H-NMR (d$_6$-DMSO, δ in ppm): 9.6–9.3 (4H, amidine); 9.1–8.7 (4H, NH und NH$_2^+$); 8.0–7.3 (9H, aromatic H); 5.4 (1H, CH); 4.6–4.3 (3H, CH$_2$ and CH); 3.1–2.7 (2H, CH$_2$); 2.2–1.6 (4H, 2×CH$_2$)

Example 120

Boc-(D,L)-Phg(4-MeO)-Pro-NH-pAmb

The hydroacetate was prepared from Boc-(D,L)-Phg(4-MeO)OH as in Example 3.

Example 121

H(D,L)-Phg(4-MeO)-Pro-NH-pAmb

The dihydrochloride was obtained from Example 120. $^1$H-NMR (d$_6$-DMSO, δ in ppm): 9.6–9.3 (4H, amidine), 9.0(8.9 (1H, NH); 8.8/8.6 (3H, NH$_3^+$); 7.9–7.8 and 7.55–7.45 and 7.05–6.90 (8H, aromatic H); 5.3 (1H, CH); 4.5–4.3 (3H, CH$_2$ and CH); 3.75 (3H, OCH$_3$); 2.2–1.6 (4H, 2×CH$_2$)

Example 122

Boc(D)-Chg-Pro-NH-pAmb a) 8 g (31.1 mmol) of Boc-(D)-Chg-OH, 9.88 g (37.3 mmol) of H-Pro-p-cyanobenzylamide×HCl, 32 ml (186.54 mmol) of DIPEA and 108 ml of PPA (50% strength in ethyl acetate) were mixed in a flask at 0° C. and stirred at 0° C.-RT for 18 h. The reaction mixture was subsequently diluted in ethyl acetate and extracted with 20% strength NaHSO$_4$ solution (5×), 5% strength NaHCO$_3$ solution and saturated brine. After drying and concentration of the organic solution, 13.8 g of pure Boc(D)-Chg-Pro-p-cyanobenzylamide remained.

b) 13.8 g of Boc(D)-Chg-Pro-p-cyanobenzylamide were dissolved in 113 ml of pyridine and 53 ml of TEA. The solution was saturated with H$_2$S gas and left to stand at RT overnight. For workup, the reaction mixture was first flushed with nitrogen and then poured into 1 l of 5% strength citric acid solution. The precipitate was filtered off, and the filtrate was extracted with ethyl acetate (3×). The precipitate was then dissolved in ethyl acetate and combined with the organic extracts. The combined phases were washed with 5% strength citric acid, dried with NaSO$_4$ [sic] and concentrated. The crude product was used in the next reaction without further purification.

c) The crude thioamide was dissolved in 120 ml of acetone and 21 ml of MeI [sic] and stirred at RT overnight. The reaction mixture was subsequently evaporated to dryness under reduced pressure, and the residue was dissolved at [sic] 48 ml of MeOH. 48 ml of a methanolic ammonium acetate solution (10% strength) was added and then the solution was stirred at RT for 18 h. To work up the amidine, the solvent was removed in a rotary evaporator, the residue was taken up in DCM, the precipitate was filtered off with suction, and the filtrate was concentrated under reduced pressure. 24.6 g of crude product were obtained. This was purified by means of reversed phase HPLC chromatography. Yield 7 g-(hydroacetate) $^1$H-NMR (d$_6$-DMSO, δ in ppm): 9.6–9.2 (b, N—H); 8.7/8.1 (2t, 1H, NH); 7.75 (2d, 2H, Ar—H); 7.45 (2d, 2H, Ar—H); 7.0/6.9 (2d, 1H, NH); 4.4 (m, 3H, CH$_2$/α-Pro); 4.0 (t, 1H, α-Chg); 3.6–3.0 (2H, γ-Pro); 2.1–1.5 (m, 11H, β,γ-Pro/Ch$_2$); 1.4/1.3 (2s, 9H, Boc); 1.1–0.9 (m, 4H) MS: 486 (M+H$^+$), 386 (–Boc), 247, 134

Example 123

H-(D-)-Chg-Pro-NH-pAmb

The compound was prepared by elimination of Boc from Example 122. $^1$H-NMR (d$_6$-DMSO, δ in ppm): 9.4–9.0 (b, NH); 8.9 (t, 1H, NH); 8.4 (b, NH); 7.8 (d, 2H, Ar—H); 7.5 (d, 2H, Ar—H); 4.4 (m, 3H, N—CH$_2$/α-Pro); 3.9–3.6 (2m, 2H, α-Pro); 3.8 (d, 1H, α-Pro); 2.0–1.5 (m, 10H, Ch/β/γ-Pro); 1.2–1.0 (m, 4H, Ch) MS: 386 (M+H$^+$), 247, 185; melting point 133° C.-(dihydrochloride)

Example 124

EtOOC-(D)-Chg-Pro-NH-pAmb

Firstly H-(D)-Chg-Pro-p-cyanobenzylamide×HCl was prepared from Boc-(D)-Chg-OH and H-Pro-p-cyanobenzylamide×HCl as in Example 3.

Then 2.5 g (6.17 mmol) of H-(D)-Chg-Pro-p-cyanobenzylamide×HCl, 2.33 ml (13.58 mmol) of DIPEA, 0.075 g (0.617 mmol) of DMAP and 0.652 ml of ethyl chloroformate were consecutively added to 25 ml of DCM at RT, and the reaction solution was stirred at RT for 18 h. The reaction mixture was subsequently diluted with DCM, washed with 20% strength NaHSO$_4$ solution, dried and concentrated. Crude yield of EtOOC—H-(D)-Chg-Pro-p-cyanobenzylamide: 2.51 g. The intermediate obtained in this way was converted into the corresponding amidine as in A.III.1. The crude product was purified by reversed phase HPLC chromatography (acetonitrile/water). Yield: 0.483 g. $^1$H-NMR (d$_6$-DMSO, δ in ppm): 8.7/8.1 (2t, 1H, NH); 7.8 (2d, 2H, Ar—H); 7.4 (2d, 2H, Ar—H); 7.4 (2d, 2H, Ar—H); 7.39/7.3 (2d, 1H, NH); 4.9/4.4 (2m, 3H, CH$_2$/α-Pro); 4.0 (2t, 1H, α-Chg); 3.8 (t, 2H, OCH$_2$); 3.7–3.3 (3m, 2H, δ-Pro); 2.1 (m, 1H, β-Pro); 1.9–1.5 (m, 11H, CH$_2$/β/γ-Pro); 1.2–0.9 (m, 9H, CH$_2$/CH$_3$) MS: 458 (M+H$^+$), 247, 134, 70-(hydroacetate)

Example 125

HOOC—CH$_2$-(D)-Chg-Pro-NH-pAmb

The compound was prepared from Example 126 by cleavage of the t-butyl ester. $^1$H-NMR (d$_6$-DMSO, δ in ppm): 8.5/8.3 (2t, 1H, NH); 7.8 (2d, 2H, Ar—H); 7.6/7.45 (2d, 2H, Ar—H); 4.4–4.2 (m, 3H, N—CH$_2$/α-Pro); 4.1 (m, 1H, α-Chg); 3.8–3.2 (4H, HOOCCH$_2$/δ-Pro); 2.1–1.4 (m, 11H); 1.2–0.9 (m, 4H) MS: 444 (M+H$^+$), 386, 247-(hydrochloride)

Example 126 tBuOOC—CH$_2$-(D)-Chg-Pro-NH-pAmb

The compound was prepared in a similar way to the tert-butyl ester precursor of Example 246. $^1$H-NMR (d$_6$-DMSO, δ in ppm): 8.4 (t, 1H, NH); 7.75 (d, 2H, Ar—H); 7.4 (d, 2H, Ar—H); 4.4 (m, 4H, N—CH$_2$/α-Pro/α-Chg); 3.8–2.9 (4H, HOOCCH$_2$/δ-Pro); 2.1–0.9 (m, 15H); 1.3 (s, 9H, tBu) MS: 500 (M+H$^+$), 444, 247, 170-(hydroacetate)

Example 127

Boc-(D)-Chα-Pro-NH-pAmb

Compound 127 was synthesized as in Example 3. $^1$H-NMR (d$_6$-DMSO, δ in ppm): 9.4 (b, 4H, NH); 8.8/8.15 (2t, 1H, NH); 7.75 (2d, 2H, Ar—H); 7.45 (2d, 2H, Ar—H); 7.05 (d, 1H, NH); 4.8/4.35 (d/m, 3H, N—CH$_2$/α-Pro/α-Chg); 3.75/3.5–3.2 (2H, α-Pro); 2.1–1.85 (4H, β/γ-Pro); 1.7–1.3 (m, 6H); 1.3 (2d, 9H, Boc); 1.4–0.9 (m, 7H) MS: 500 (M+H$^+$), 400 (–Boc), 247, 134; melting point 125–7° C. (hydroacetate)

Example 128

Me-(D)-Chα-Pro-NH-pAmb

The compound was synthesized by elimination of Cbz from Example 129. $^1$H-NMR (d$_6$-DMSO, δ in ppm): 9.3/8.9 (2s, 4H, NH); 8.85/8.8 (2sb, 2H, NH); 8.7 (t, 1H, NH); 7.8 (2d, 2H, Ar—H); 7.5 (2d, 2H, Ar—H); 4.4 (m, 3H, N—CH$_2$/α-Pro); 4.25 (db, 1H; α-Chg); 3.9/3.4 (2m, 2H, δ-Pro); 2.5 (s, 3H, NCH$_3$); 2.2 (m, 1H, β-Pro); 2.5 (s, 3H, NCH$_3$); 2.2 (m, 1H, β-Pro); 2.0–1.8 (m, 4H); 1.8–1.5 (m, 6H); 1.4–0.9 (6H) MS: 414 (M+H$^+$), 247, 140-(hydroacetate)

Example 129

Me-(Z )-(D)-Chα-Pro-NH-pAmb

The compound was prepared starting from Me-(Z)-(D)-Chα-OH and H-Pro-p-cyanobenzylamide×HCl as in Example 3. ¹H-NMR (d₆-DMSO, δ in ppm): 9.8–9.2 (b, 4H, NH); 8.8/8.5 (2t, 1H, NH); 7.8 (2d, 2H, Ar—H); 7.5 (2d, Ar—H); 7.4 (m, 5H, Ph-H); 5.2–5.0 (2H, OCH₂); 4.95–4.5 (1H, α-Pro); 4.4 (m, 3H, N—CH₂/α-Cha); 3.6–3.0 (2H, δ-Pro); 2.82/2.75/2.7 (3s, 3H, NCH₃); 2.1 (m, 1H, β-Pro); 1.9–1.4 (m, 11H, β/γ-Pro/CH₂); 1.2–0.8 (m, 5H) FAB-MS: 548 (M+H⁺)-(hydroacetate)

Example 130

N,N-Me-(D)-Chα-Pro-NH-pAmb

The compound was synthesized starting from N,N-dimethylcyclohexylalanine and H-Pro-p-cyanobenzylamide×HCl as in Example 3. ¹H-NMR (d₆-DMSO, δ in ppm): 8.8/8.4 (2t, 1H, NH); 7.8 (2d, 2H, Ar—H); 7.45 (2d, 2H, Ar—H); 4.45–4.3 (d/m, 3H, N—CH₂/α-Pro); 3.9 (m, 1H, α-Cha); 3.6–3.2 (2H, δ-Pro); 2.2 (2s, 6H, NCH₃); 2.1–1.5 (m, 13H); 1.3–0.8 (m, 4H) FAB-MS: 428 (M+H⁺)-(hydroacetate)

Example 131

Boc-(D)-Trp(Boc)-Pro-NH-pAmb

The compound was synthesized starting from Boc-(D)-Trp(Boc)-OH and H-Pro-p-cyanobenzylamide×HCl as in Example 3. ¹H-NMR (d₆-DMSO, δ in ppm): 9.8–9.2 (b, N—H); 8.8–8.5 (2sb, 1H, NH); 8.25(8.0/7.8–7.2 (m, 10H, Ar—H/NH); 4.85/4.5–4.2 (d/m, 4H, CH₂-H); 3.6/3.5 (2m, 2H, CH₂, Pro); 3.1–2.8 (m, 2H, CH₂); 2.2–1.6 (m, 4H, Pro), 1.3 (2s, 18H, Boc) FAB-MS: 633 (M+H⁺)-(hydroacetate)

Example 132

H-(D)-Trp-Pro-NH-pAmb

The compound was prepared by elimination of Boc from Example 131. ¹H-NMR (d₆-DMSO, δ in ppm): 11.1 (s, 1H, NH); 9.4/9.15 (2s, 4H, N—H); 8.8 (t, 1H, NZ); 8.6 (8, 3H, N—H); 7.75 (d, 2H, Ar—H); 7.45 (d, 3H, Ar—H); 7.35 (d, 1H, Ar—H); 7.25 (s, 1H, Ar—H); 7.0 (2t, 2H, Ar—H); 4.3 (m, 2H, CH₂), 4.18 (sb, 1H, α-H); 3.5 (m, 2H, CH₂, Pro); 3.3–3.1 (m, 2H, CH₂), 2.15 (dd, 1H, Pro); 1.6/1.4 (2m, 3H, β/γ-Pro) FAB-MS: 433 (M+H⁺)-(dihydrochloride)

Example 133

Boc-(D,L)-Dpα-Pro-NH-pAmb

The compound was synthesized starting from Boc-(D)-Dpa-OH and H-Pro-p-cyanobenzylamide×HCl as in Example 3. ¹H-NMR (d₆-DMSO, δ in ppm): 8.6/8.1 (2t, 1H, NH); 7.75 (2d, 2H, Ar—H); 7.45–7.0 (m, 13H, Ar—H/NH); 5.25/5.1 (2t, 1H, α-Dpa); 4.4–4.1 (3H, N—CH₂/α-Pro); 3.75 (m, 1R, CH); 3.6–2.95 (2H, δ-Pro); 2.0–1.5 (4H, β/γ-Pro); 1.2 (2ds, 9H, Boc) MS: 570 (M+H⁺), 470 (–Boc), 247, 196, 134, melting point 156° C.-(hydroacetate)

Example 134

H-(D or L)-Dpα-Pro-NH-pAmb/a

Compound 134 was synthesized by elimination of Boc from Example 133 and subsequent separation of the diastereomers by reversed phase HPLC separation. ¹H-NMR (d₆-DMSO, δ in ppm): 9.3 (2s, 4H, NH); 8.9/8.2 (2t, 1H, NH); 8.4 (b, 3H, NH); 7.8 (2d, 2H, Ar—H); 7.6 (2d, 2H, Ar—H); 7.5–7.1 (1OH, Ar—H); 5.1/4.6 (2d, 1H, α-Dpa); 4.4–4.1 (4H, N—CH₂/α-Pro/CH); 3.8–3.0 (2H, δ-Pro); 2.1–1.1 (4H, β/γ-Pro) FAB-MS: 470 (M+H⁺)-(dihydroacetate)

Example 135

H-(D or L)-Dpα-Pro-NH-pAmb/b

¹H-NMR (d₆-DMSO, δ in ppm): 9.3/9.2 (2s, 4H, NH); 8.4 (t, 1H, NH); 8.35 (sb, 3H, NH); 7.8/7.65 (2d, 4H, Ar—H); 7.4–7.1 (1OH, Ar—H); 5.0 (d, 1H, α-Dpa); 4.4/3.9 (M,4H, n-CH₂/α-Pro/CH); 3.6/2.9 (2m, 2H, δ-Pro); 1.7–1.3 (4H, β/γ-Pro) FAB-MS: 470 (M+H⁺)-(dihydroacetate)

Example 136

EtOOC-(D oder L)-Dpα-Pro-NH-pAmb/a

To prepare the abovementioned compound, Boc-(D,L)-Dpa-Pro-p-cyanobenzylamide (intermediate for synthesizing Example 133) was firstly converted using dioxane/HCl into the corresponding hydrochloride H-(D,L)-Dpa-Pro-p-cyanobenzylamide×HCl. Subsequently, the salt was converted as in Example 124 into the diastereomeric pair of products. The two diastereomers were separated from one another by reversed phase HPLC chromatography (acetonitrile/water). ¹H-NMR (d₆-DMSO, δ in ppm): 8.6/6.6 (2t, 1H, NH); 7.8–7.0 (m, 15H, Ar—H, NH); 5.3/5.1 (2t, 1H, α-Dpa); 4.4 (2d, 1H, α-Pro); 4.3/4.1 (2t, 2H, CH₂); 4.0 (m, 1H, CH); 3.85 (t, 2H, OCH₂); 3.6/3.3/3.0 (3m, 2H, δ-Pro); 2.0–1.4 (m, 4H, β/γ-Pro); 1.0 (m, 3H, CH₃) MS: 542 (M+H⁺), 268, 134, 70-(hydroacetate)

Example 137

EtOOC-(D or L)-Dpα-Pro-NH-pAmb/b

The compound was prepared as in Example 3. ¹H-NMR (d₆-DMSO, δ in ppm): 8.2 (2t, 1H, NH); 7.75 (d, 2H, Ar—H); 7.6 (d, 2H, Ar—H); 7.4–7.2 (m, 12H, Ar—H); 5.15 (m, 1H, α-Dpa); 4.4 (m, 3H, NCH₂/α-Pro); 3.95 (m, 1H, CH); 3.8/3.1 (2m, 2H, δ-Pro); 3.7 (m, 2H, OCH₂); 1.8–1.4 (m, 4H, β/γ-Pro); 1.0 (m, 3H, CH₃) MS: 542 (M+H⁺), 268, 134, 70-(hydroacetate)

Example 138

HOOC—CH₂-(D or L)-Dpa-Pro-NH-PAmb/a

Firstly, the Boc group was eliminated from Boc-(D,L)-Dpa-Pro-p-cyanobenzylamide (intermediate in the synthesis of Example 133) using dioxane/HCl. 3.42 g (7 mmol) of the hydrochloride obtained in this way were dissolved in 20 ml of MeOH and, after addition of 0.6 g (6.65 mmol) of glyoxylic acid hydrate and 1.75 g (28 mmol) of NaCNBH₃, stirred overnight. For workup, the reaction mixture was concentrated, the residue was taken up in DCM, and the organic solution obtained in this way was extracted with water. The residue after drying and concentration of the organic phase was dissolved in 5 ml of MeOB, and the required product was precipitated by dropwise addition to diisopropyl ether. Crude yield: 3.7 g. The crude product was converted without further purification to the corresponding amidine as in Example A.III.1. The mixture of diastereomers was separated by reversed phase HPLC (acetonitrile/water). MS: 528 (M+H⁺), 254-(hydroacetate)

Example 139

HOOC—CH₂-(D or L)-Dpa-Pro-NH-pAmb/b

MS: 528 (M+H⁺), 254, 134, 83-(hydroacetate)

Example 140

Boc(D or L)-Dpa(4,4'-(Cl)$_2$)-ProNH-pAmb/a

The compound was prepared starting [lacuna] Boc-(D.L)-Dpa(4,4'-(Cl)$_2$)—OH and H-Pro-p-cyanobenzylamide×HCl as in Example 3. The synthesized pair of diastereomers was separated by reversed phase HPLC chromatography. MS: 638 (M+H$^+$), 538 (–Boc), 303, 277, 247-(hydroacetate)

Example 141

Boc(D or L)-Dpa-(4,4'-(Cl)$_2$)-Pro-NH-pAmb/b

MS: 638 (M+H$^+$), 538 (–Boc), 303, 247, 134, 70-(hydroacetate)

Example 142

H-(D or L)-Dpa(4,4'-(Cl)$_2$)-Pro-NH-pAmb/a

The compound was prepared by elimination of Boc from Example 140. $^1$H-NMR (d$_6$-DMSO, δ in ppm): MS: 538 (M+H$^+$), 303, 247, 134, 70-(hydroacetate)

Example 143

H-(D or L)-Dpa(4,4'-(Cl)$_2$)-Pro-NH-pAmb/b

The compound was prepared by elimination of Boc from Example 141. MS: 538 (M+H$^+$), 303, 264, 247, 134, 70-(hydroacetate)

Example 144

EtOOC-(D or L)-Dpa(4,4'-(Cl)$_2$)-Pro-NH-pAmb/a

To prepare the abovementioned compound, Boc-(D,L)-Dpa(4,4'-(Cl)2)-Pro-p-cyanobenzylamide (intermediate for synthesizing Example 141) was firstly converted using dioxane/HCl into the corresponding hydrochloride H-(D,L)-Dpa(4,4'-(Cl)$_2$)-Pro-p-cyanobenzylamide×HCl. The salt was subsequently converted into the mixture of diastereomeric products as in Example 124. The two diastereomers were separated from one another by reversed phase HPLC chromatography (acetonitrile/water). $^1$H-NMR (d$_6$-DMSO, δ in ppm): 8.6 (2t, 1H, NH); 7.75 (2d, 2H, Ar—H); 7.6–7.1 (11H, Ar—H/NH); 5.2/5.0 (2t, 1H, α-Dpa); 4.4/4.38 (2d, 1H, CH); 4.3 (m, 1H, α-Pro); 4.0 (m, 2H, NCH2); 3.75 (m, 2H, OCH2); 3.7–3.3 (2H, 5-Pro); 2.0 (m, 1H, β-Pro); 1.95–1.4 (m, 4H, β/γ-Pro); 1.0 (2t, 3H, CH3) MS: 610 (M+H$^+$), 247, 134, 70-(hydroacetate)

Example 145

EtOOC-(D or L)-Dpa(4,4'-(Cl)$_2$)-Pro-NH-pAmb/b $^1$H-NMR (d$_6$-DMSO, δ in ppm): 8.2 (2t, 1H, NH); 7.75 (2d, 2H, Ar—H); 7.6–7.1 (11H, Ar—H/NH); 5.1 (2t, 1H, α-Dpa); 4.4 (2d, 1H, CH); 4.3 (m, 2H, NCH2); 4.0/4.39 (m, 1H, α-Pro); 3.85 (m, 2H, OCH2); 3.7 (2H, δ-Pro); 1.9–1.5 (4H, β/γ-Pro); 1.0 (2t, 3H, CH3) MS: 610 (M+H$^+$), 247, 185, 134, 93-(hydroacetate)

Example 146

HOOC—CH$_2$-(D or L)-Dpa(4,4'-(Cl)$_2$)-Pro-NH-pAmb/a

Firstly the Boc group was eliminated from Boc-(D,L)-Dpa(4,4'-Cl)-Pro-p-cyanobenzylamide (intermediate in the synthesis of Example 140) using dioxane/HCl. The required product was subsequently prepared as in Example 138. $^1$H-NMR (d$_6$-DMSO, δ in ppm): 11.2 (b, COOH); 8.9/8.6 (2sb, 1H, NH); 7.8–7.2 (14H, Ar—H/NH); 4.4–4.0 (5H, CH7N—CH2/α-Dpa/α-Pro); 3.8–3.0 (2H, δ-Pro); 2.8 (2d, 2H, HOOC—CH2); 2.0–1.4 (4H, β/γ-Pro) MS: 596 (M+H$^+$), 247, 134, 93, 70-(hydroacetate)

Example 147

HOOC—CH$_2$-(D or L)-Dpa(4,4'-(Cl)$_2$)-Pro-NH-pAmb/b

FAB-MS: 596 (M+H$^+$)

Example 148

H-(D or L)-Dch-Pro-NH-pAmb/a

Compound 148 was synthesized starting from Boc-(D,L)-Dch-OH and H-pro-p-cyanobenzylamide×HCl as in Example 3. The synthesized pair of diastereomers was separated by reversed phase HPLC chromatography. $^1$H-NMR (d$_6$-DMSO, δ in ppm): 9.3–9.0 (b, NH); 8.9/8.5 (2t, 1H, NH); 7.75/7.5 (2d, 4H, Ar—H); 4.5–4.0 (4H, N—CH2/α-Pro/α-Dch); 3.7–3.0 (2H, δ-Pro); 2.2–1.0 (4H, β/γ-Pro) FAB-MS: 481 (M+H$^+$); mp: 127° C.-(dihydroacetate)

Example 149

H-(D or L)-Dch-Pro-NH-pAmb/b

FAB-MS: 481 (M+H$^+$); mp: 127° C.-(dihydroacetate)

Example 150

Boc-(D)-Val-Pro-NH-pAmb

Prepared as in Example 3. Melting point 132–145° C.-(hydroacetate)

Example 151

H-(D)-Val-Pro-NH-pAmb

Prepared from Example 150. Melting point 60–80° C.-(dihydrochloride)

Example 152

Boc-(D)-Leu-Pro-NH-pAmb

Prepared as in Example 3. Melting point 68–82° C.-(hydroacetate)

Example 153

H-D-Leu-Pro-NH-pAmb

Prepared from Example 152. Melting point 228–233° C.-(dihydrochloride)

Example 154

Boc-(D)-Gly(α-tBu)-Pro-NH-pAmb

Prepared as in Example 3. Melting point 211–220° C.-(hydroacetate)

Example 155

H-(D)-Gly(α-tBu)-Pro-NH-pAmb

Prepared from Example 154. Melting point 236–239° C.-(dihydrochloride)

Example 156

Boc-(D)-Ala(P-tBu)-Pro-NH-pAmb

Prepared as in Example 3. Melting point 185–192° C. (hydroacetate)

Example 157

H-(D)-Ala(P-tBu)-Pro-NH-pAmb

Prepared from Example 156. Melting point 225–231° C. (dihydrochloride)

Example 158

H-(D or L)-Msu-Pro-NH-pAmb/a

The dihydrochloride was prepared as in Example 3 from Boc-(D,L)-Msu-OH and then the Boc group was eliminated as in A.I.c. The diastereomers were separated by HPLC. $^1$H-NMR (DMSO-$d_6$, δ in ppm): 9.40/9.20 (4H, amidine), 8.9 (1H, Ne), 8.55 (3H, $NH_3^+$), 7.85/7.50 (4H, aromatic H), 4.50–4.35 (4H, $CH_2$ and 2×CH), 3.85–ca. 3.3 (4H, 2×$CH_2$), 2.95 (3H, $CH_3$), 2.3–1.8 (6H, 3×$CH_2$)

Example 159

H-(D or L)-Msu-Pro-NH-pAmb/b (Dihydrochloride); $^1$H-NMR (DMSO-$d_6$, δ in ppm): 9.45/9.30 (4, amidine), 8.95 (1H, NH), 8.85 (3H, $NH_3^+$), 7.80/7.45 (4H, aromatic H), 4.4–4.2 (4H, $CH_2$ and 2×CH), 3.85–ca. 3.3 (4H, 2×$CH_2$), 3.00 (3H, $CH_3$), 2.3–1.7 (6H, 3×$CH_2$)

Example 160

Boc-(Cyclo)Leu-Pro-NH-pAmb

Compound 160 was synthesized starting from Boc-(cyclo)Leu-OH and H-Pro-p-cyanobenzylamide×HCl as in Example 3. MS: 472 (M+H$^+$), 372 (–Boc); 247, 185, 140- (hydroacetate)

Example 161

H-(Cyclo)Leu-Pro-NH-pAmb

The compound was synthesized by elimination of Boc from Example 160. FAB-MS: 372 (M+H$^+$)-(dihydroacetate)

Example 163

H-Gly-Pro-NH-pAmb

The dihydrochloride was obtained by elimination of Boc from Boc-Gly-Pro-NH-pAmb which was prepared starting from Boc-Gly-OH as in Example 3. $^1$H-NMR (DMSO-$d_6$, δ in ppm): 9.50/9.25 (4H, amidine), 8.85 (1H, NH), 8.30 (3H, ($NH_3^+$), 7.80/7.45 (4H, aromatic H), 4.5–4.2 (3H, $CH_2$ and CH), 3.9–ca. 3.3 (4H, 2×$CH_2$), 2.2–1.7 (4H, 2×$CH_2$)

Example 166

Ph-$CH_2$-Gly-Pro-NH-pAmb

The dihydrochloride was obtained by elimination of Boc from Ph-$CH_2$-(Boc)Gly-Pro-NH-pAmb hydroacetate. $^1$H-NMR (DMSO-$d_6$, δ in ppm): 9.6 (2H, $NH_2^+$), 9.4/9.2 (4H, amidine), 8.80 (1H, NH), 7,.80 [sic]–7.35 (9H, aromatic H), 4.40–4.25 (3H, $CH_2$ and CH), 4.10 (2H, $CH_2$), 3.95 (2H, $CH_2$), 3.6–3.4 (2H, $CH_2$, 2.2–1.8 (4H, 2×$CH_2$)

Example 176

β-Naphtyl-$SO_2$-Pro-NH-pAmb [sic]

Prepared by coupling β-naphthyl-$SO_2$Cl with H-Pro-$OCH_3$, subsequently hydrolyzing the ester, coupling with p-cyanobenzylamine and converting the nitrile functionality into the amidine group. Melting point 66–72° C. (hydroacetate)

Example 177 p-Tol-$SO_2$-Pro-NH-pAmb

Prepared as in Example 176. Melting point 89–95° C. (hydroacetate)

Example 178

Ph-$CH_2$—$CH_2$—$SO_2$-Pro-NH-pAmb

Prepared as in Example 176. Melting point 61–69° C. (hydroacetate)

Example 179

H-Asp-Pro-NH-pAmb

The Boc group was eliminated from Boc-Asp(OBzl)-Pro-NH-pAmb as in A.I.c., and the benzyl ester was hydrogenated to the acid with Pd/C. The dihydrochloride was obtained by treatment with ethereal HCl. $^1$H-NMR (DMSO-$d_6$, δ in ppm): 9.4/9.2 (4H, amidine), 8.6 (1H, NH), 8.45 (3N, $NH_3^+$), 7.80/7.45 (4H, aromatic H), 4.45–4.30 (4H, $CH_2$ and 2×CH), 3.8–ca. 3.5 (2H, $CH_2$), 3.2–ca. 2.6 (2H, $CH_2$), 2.2–1.7 (4H, 2×$CH_2$)

Example 191

H-(D)-Asp-Pro-NH-pAmb

The dihydrochloride was prepared as in Example 179. $^1$H-NMR (DMSO-$d_6$, δ in ppm): 9.45/9.30 (4H, amidine), 9.05 (1H, NH), 8.9 (3H, $NH_3^+$), 7.80/7.45 (4H, aromatic H), 4.45–4.15 (4H, $CH_2$ and 2×CH), 2.2–1.7 (4H, 2×$CH_2$); FAB-MS: 362 (M+H$^+$)

Example 193

H-(D)-Asp(OtBu)-Pro-NH-pAmb

The dihydroacetate was prepared from Z-(D)-Glu(OtBu)-Pro-NH-pAmb by hydrogenation on Pd/C. $^1$H-NMR (DMSO-$d_6$, δ in ppm): 9.3 (4H, amidine), 8.5 (1H, NH), 8.3 (3H, $NH_3^+$), 7.75/7.25 (4H, aromatic H), 4.4–4.3 (4H, $CH_2$ and 2×CH), 2.9–2.6 (2H, $CH_2$, 2.2–1.8 (4H, 2×$CH_2$), 1.4 (9H, tBu); FAB-MS: 418 (M+H$^+$)

Example 199

(D)-Ph-$CH_2$—CHOH—CO-Pro-NH-pAmb (a) 3-Phenyl-D-lactyl-proline (p-cyanobenzyl)amide 5.5 g (20.4 mmol) of o-tetrahydropyranyl-3-phenyl-D-lactic acid (WO 93/18060) were dissolved in 30 ml of DMF and, successively, 5.4 g (20.4 mmol), N-(p-cyanobenzyl) prolin-amide, 3.3 g (20.4 nmol) of N-hydroxybenzotriazole, 3.0 g DIPEA and 4.33 g (20.6 mmol) of dicyclohexylcarbodiimide were added. The mixture was left to stir at room temperature for 48 h. The precipitated urea was filtered off with suction and then the solvent was substantially removed under reduced pressure, and the residue was mixed with 50 ml of water and extracted with ethyl acetate. After washing with water, NaHCO$_3$ solution and drying over Na$_2$SO$_4$, the ethyl acetate was distilled off, the remaining oily residue was dissolved in methanol, and the pH was. adjusted to 2 with p-toluenesulfonic acid. This solution was left to stand at room temperature for 6 h. The methanol was then distilled off, and the residue was taken up in ethyl acetate and washed with water, 5% strength citric acid and NaBCO$_3$ solutions. The residue obtained after drying over Na$_2$SO$_4$ and removal of the solvent by distillation was purified by column chromatography (eluent: methylene chloride/acetone/methanol, 45/5/2). 2.5 g of white crystals were obtained, and these melted at 108° C.–110° C. after crystallization from an ether/hexane mixture.

(b) 3-Phenyl-D-lactyl-proline (p-amidinobenzyl) amide acetate 2.0 g of the above compound and 3 ml of triethylamine were dissolved in 30 ml of pyridine, saturated with H$_2$S at 0° C. and left to stand at room temperature overnight. A TLC check (CH$_2$Cl$_2$/MeOH, 9/1) showed that conversion to the thioamide was complete. For isolation, the pyridine was substantially removed by distillation under reduced pressure, and the residue was taken up in 250 ml of ethyl acetate and washed with brine, 5% strength citric acid and NaHCO$_3$ solution. Drying and removal of the solvent by distillation resulted in 2.3 g of amorphous thioamide.

The thioamide was distilled in 40 ml of acetone and, after addition of 4 ml of methyl iodide, left to stand at room temperature for 6 h. The solvent was stripped off and then the amorphous residue was stirred with dry ether and subsequently dried. The S-methyl thioimidic methyl ester hydroiodide was dissolved in 50 ml of ethanol, 15 ml of 10% strength ammonium acetate solution were added, and the mixture was heated at 60° C. for 3 h. For isolation, the solvent was stripped off, the residue was dissolved in 100 ml of CH$_2$Cl$_2$, the insoluble constituents were filtered off and subsequently the CH$_2$Cl$_2$ was distilled off. Digestion with an ethyl acetate diethyl-ether mixture removed the impurities soluble therein. The remaining mixed iodide/acetate was dissolved in acetone/water (3/2) and converted into the pure acetate using an IRA acetate ion exchanger and subsequently purified by column chromatography (eluent: methylene chloride/methanol/50% strength acetic acid 40/10/1.5). The pure fractions were freeze dried after removal of the eluent. 1.1 g of white powder remained, melting point 185° C.–187° C., FAB-MS: 395 (M+H$^+$).

Example 200

(D)-Man-Pro-NH-pAmb

The hydroacetate was prepared as in Example 199 starting from O-tetrahydropyranyl-(D)-mandelic acid (WO 93/18060); white crystals; melting point 211–213° C.; FAB-MS: 381 (M+H$^+$)

Example 202

H-(D)-Phe-Aze-NH-pAmb

The mixed hydroiodide/hydrochloride was prepared by reacting Boc-(D)-Phe-OH with H-Aze-p-cyanobenzylamide as in Example 3 as far as the amidine and subsequent Boc cleavage. $^1$H-NMR-(DMSO-d$_6$, δ in ppm): 9.3/9.1 (4H, amidine), 9.0 (1H, NH, 8.7 (3H, NH$_3^+$), 7.8–7.2 (9H, aromatic H, 4.5–ca. 3.3 (6H, 2×CH$_2$ and 2×CH), 3.2–2.8 (2H, CH$_2$), 2.2–1.8 (2H, CH$_2$)

Example 204 and Example 205

H-(D)-Phe-(D or L)-Pic-NH-pAmb/a and H-(D)-Phe-(D or L)-Pic-NH-PAmb/b

The dihydrochloride of the pair of diastereomers was prepared from Boc-(D)-Phe-OH and H-(D,L)-Pic-p-cyanobenzylamide as far as the amidine as in Example 3. The Boc group was subsequently eliminated. $^1$H-NMR-(DMSO-d$_6$, δ in ppm): 9.6–9.3 (4H, amidine), 9.1–8.7 (4H, NH and NH$_3^+$), 7.8–7.2 (9H, aromatic H), 4.6–4.3 (4H, CH$_2$ and 2×CH), 3.3–2.8 (2H, CH$_2$), 2.3–0.9 (6H, 3×CH$_2$); FAB-MS: 408 (M+H$^+$)

The pair of diastereomers was subsequently separated by HPLC chromatography into Examples 204 and 205.

Example 207

H-(D)-Phe-(D,L/trans)-Pic(4-Me)-NH-pAmb

The dihydrochloride was synthesized starting from Boc-(D)-Phe-OH and H-(D,L/trans)-Pic(4-Me)-p-cyanobenzylamide as in Example 204/205; Melting point 160–170° C.

Example 208

Boc-(D)-Phe-Pyr-NH-pAmb

Compound 160 was synthesized starting from Boc-(b)-Phe-OH and H-Pyr-p-cyanobenzylamide×HCI [sic] as in Example 3. MS: 492.5 (M+H$^+$), 392, 245, 133

Example 209

H-(D)-Phe-Pyr-NH-pAmb

The compound was synthesized by elimination of Boc from Example 208. $^1$H-NMR (d$_6$-DMSO, δ in ppm): 9.4–9.2 (b, N—H); 8.8–8.2 (b, N—H); 8.6 (2t, 1H, NH); 7.75 (2d), 2H, Ar—H); 7.45 (2d, 2H, Ar—H; 7.35–7.1 (m, 5H, Ar—H); 6.15/6.0/5.85/5.75 (4sb, 2H, CH═CH); 5.5/4.9 (sb, 1H, α-Pyr); 4.4–4.2 (m, 4H, CH$_2$/α-Phe/δ-Pyr); 3.6 (d, 1H, δ-Pyr); 3.1–3.0 (m, 2H, CH$_2$-Ph) FAB-MS: 392 (M+H$^+$)

Example 210

Boc-(D)-Phe-Hyp(OtBu)-NH-pAmb

The compound was synthesized starting from Boc-(D)-Phe-Hyp(OtBu)-OH and p-cyanobenzylamine×HCI [sic] as in Example 1. MS: 566 (M+H$^+$), 466(–Boc), 319 (466-Phe Example 211

H-(D)-Phe-Hyp-NH-pAmb

The compound was synthesized by elimination of Boc and tButyl from Example 210. $^1$H-NMR (DMSO-d$_6$, δ in ppm): 9.35 (s, 2H, N—H); 9.1 (s, 2H, N—H); 8.8 (t, 1H, NH); 8.5 (sb, 3H, N—H); 7.75 (2d, 2H, Ar—H); 7.45 (2d, 2H, Ar—H); 7.35–7.2 (m, SH, Ar—H); 4.4–4.2 (m, 5H, CH$_2$/2 α-H/CHOH; 3.8 (m, 1H, Pro); 3.0 (m, 2H, CH$_2$); 2.75 (m, 1H, Pro); 1.95 (m, 1H, Pro); 1.8 (m, 3H, Pro) FAB-MS: 410 (M+H$^+$)

Example 213

H-(D)-Phe-(Me)Val-NH-pAmb

The dihydrochloride was synthesized starting from Boc-(D)-Phe-OH and H-(Me)Val-p-cyanobenzylamide as in Example 3. $^1$H-NMR(DMSO-d$_6$, δ in ppm): 9.45/9.25 (4H, amidine), 8.8 (1H, NH), 8.6 (3H, NH$_3^+$), 7.8/7.5/7.3 (9H, aromatic H), 4.65 (1H, CH), 4.60 (2H, CH$_2$), 4.45–4.20 (2H, CH$_2$), 3.20–2,95 (2H, CH$_2$), 2.85 (3H, N—CH$_3$), 2.0 (1H, CH), 0.8/0.45 (6H, 2×CH$_3$)

Example 216

Boc-(D)-Phe-Tia-NH-pAmb

The compound was synthesized starting from Boc-(D)-Phe-Tia-OH and p-cyanobenzylamine hydrochloride as in Example 1. MS: 512 (M+H$^+$), 412 (–Boc), 265, 204, 133

Example 217

H-(D)-Phe-Tia-NH-pAmb

The compound was synthesized by elimination of Boc from Example 216. $^1$H-NMR (DMSO-d$_6$, δ in ppm): 9.4/9.2 (2sb, 4H, N—H); 9.0 (t, 1H, NH; 7.75 (2d, 2H, Ar—H); 7.45 (2d, 3H, Ar—H); 7.4–7.2 (m, 5H, Ar—H); 4.8 (d, 1H, α-Tia); 4.7/3.7 (2d, 2H, NCH2S); 4.4–4.2 (m, 3H, CH$_2$/α-Phe); 3.2/3.1 (2m, 2H, SCH$_2$); 3.0/2.7 (m, 3H, CH$_2$-Ph) FAB-MS: 412 (M+H$^+$)

Example 218

H-(D)-Phe-Pro-NH-3-(6-am)-pico a) 2-Cyano-5-(azidomethyl)pyridine 14.5 g (0.07 mol) of trifluoroacetic anhydride dissolved in 20 ml of methylene chloride were added dropwise to a solution of 8.8 g (0.07 mmol [sic]) of 2-cyano-5-(hydroxymethyl)-pyridine (WO 83/01446) and 6.9 g of triethylamine in 200 ml of methylene chloride at room temperature and subsequently stirred for 2 h. After the methylene chloride had been removed by distillation, the residue was dissolved in a mixture of 50 ml of toluene and 50 ml of dimethyl sulfoxide, 11.2 g (0.17 mol) of sodium azide and 0.7 g of tetrabutyl-ammonium bromide were added, and the mixture was stirred at room temperature overnight.

The reaction mixture was poured into 300 ml of water and extracted several times with ether. After drying with Na$_2$SO$_4$ and removal of the ether by distillation, 6.8 g of yellowish crystals remained (melting point 62–64° C.) and were used in the mixed reaction without further purification.

b) 2-Cyano-5-(aminomethyl)pyridine

The compound obtained in a) was dissolved in 45 ml of tetrahydrofuran and 1.2 ml of water and, while stirring, 11.2 g of triphenylphosphine were added in portions. The reaction mixture was left to stand at room temperature overnight.

The residue after removal of the solvent by distillation was taken up in 100 ml of ether, the precipitated triphenylphosphine oxide was filtered off with suction, and the filtrate was adjusted to pH 2 with ethereal hydrochloric acid. The precipitated hydrochloride was filtered off with suction, washed with ether and digested successively with toluene and hot isopropanol. 4.7 g (40%) of hydrochloride were isolated, melting point 253–256° C. (decomposition).

c) Boc-D-phenylalanylproline (6-cyano-3-picolyl) amide 8.12 g of diisopropylethylamine and subsequently 11 ml (15 mmol) of propanephosphonic anhydride (50% strength solution in ethyl acetate) were added dropwise to a solution of 2.11 g (12.5 mmol) of 2-cyano-5-(aminomethyl)pyridine and 4.5 g (12.5 mmol) of Boc-D-Phe-Pro-OH in 70 ml of CH$_2$Cl$_2$ at –5° C. The mixture was then stirred for 2 h, during which the temperature was allowed to rise from –5° to 20° C. The organic phase was washed with water, 5% strength sodium bicarbonate and 5% strength citric acid solutions, dried over Na$_2$SO$_4$ and evaporated to dryness. A pale yellowish crystalline residue was obtained, melting point 167–170° C., and was used without further purification in the next reaction.

d) Boc-D-phenylalanylproline (6-amidino-3-picolyl) amide 1.15 g (16.5 mmol) of hydroxylamine hydrochloride were suspended in 5 ml of ethanol, 1.2 g of 25% strength ammonia solution were added, and the mixture was stirred for 10 min. After addition of 45 ml of ethanol, the precipitated salt was filtered off with suction and 3.14 g (6.6 mmol) of the above compound (stage c) were added to the solution. The hydroxyamidine compound separated out after a short time and, after stirring for 30 minutes, was filtered off with suction and washed with a little cold water and ethanol. The residue moist with ethanol was dissolved in 40 ml of ethanol and 8 ml of glacial acetic acid, 250 mg of 10% Pd/C were added and hydrogenation was carried out at about 50° C. After 5 hours, TLC (CH$_2$Cl$_2$/MeOH/50% strength acetic acid, 20/5/1) showed no detectable starting material.

After removal of the catalyst by filtration with suction through a layer of Cellite [sic], the solvent was removed by distillation, with addition of toluene toward the end. After addition of 50 ml of acetone, the amidine acetate crystallized out and was filtered off. White crystals, melting point 130–4° C., FAB-MS: 495 (M+H$^+$).

e) H-(D)-Phe-Pro-NH-3-(6-am)-pico

The Boc group was eliminated from compound d) under standard conditions. Dihydrochloride; white crystals, melting point 235–240° C. FAB-MS: 395 (M+H$^+$)

Example 219

Boc-(D)-Chg-Pro-NH-3-(6-Am)-pico a) Boc-D-Cyclohexylglycyl-proline 29 g (0.113 mol) of Boc-(D)-cyclohexylglycine and 18.7 g (0.113 mol) of proline methyl ester hydrochloride were suspended in 300 ml of CH$_2$Cl$_2$ and dissolved by dropwise addition of 58.3 g (0.45 mol) of diisopropylethylamine. After cooling to –15° C., 113 ml (0.147 mol) of propanephosphonic anhydride (50% strength solution in ethyl acetate) were added dropwise, and the mixture was stirred for 1 hour.

After addition of 200 ml of water, the organic phase was separated off and washed with aqueous K$_2$CO$_3$ solution, 0.5 N hydrochloric acid and 5% strength bicarbonate solution. After drying with Na$_2$SO$_4$, the solvent was dissolved off, the oily residue (41 g) was dissolved in 400 ml of ethanol, 120 ml of 1 N NaOH were added, and the mixture was stirred at room temperature for 2 hours.

After removal of the alcohol by distillation, the aqueous phase was diluted with water and extracted several times with methyl tert-butyl ether. The aqueous phase was acidified with KHSO$_4$ solution and extracted 3×with CH$_2$Cl$_2$. The oily residue after drying and removal of the methylene chloride by distillation was crystallized from diisopropyl etherin-hexane (1/3). 28 g of white crystals were isolated, melting point 145–148° C.

b) Boc-(D)-Cyclohexylglycylproline (6-cyano-3-picolyl)amide 26.6 g (0.075 mol) of Boc-(D)-cyclohexylglycylproline and 12.7 g (0.075 mol) of 6-cyano-3-picolylamine hydrochloride were suspended in 300 ml of $CH_2Cl_2$, and 47 g (0.364 mol) of diisopropylethylamine were added. Subsequently, at −10° C., 66 ml of propanephosphonic anhydride (50% strength solution in ethyl acetate) were added dropwise and, after stirring at 0° C. for 1 hour, 200 ml of water were added and the $CH_2Cl_2$ phase was separated off. The organic phase was washed with 0.1 N sodium hydroxide solution and water and then dried, and the solvent was distilled off. The residue was taken up in 100 ml of ethyl acetate, whereupon crystallization rapidly started and was completed by adding 150 ml of n-hexane. Filtration with suction and drying resulted in isolation of 31.4 g (89% of theory) of white crystals, melting point 150–151° C.

c) Boc-(D)-Cyclohexylglycylproline (6-amidino-3-picolyl)amide

The amidine formation took place as in Example 218, stage d. Acetate: white crystals, melting point 160–8° C. (decomposition); FAB-MS: 487 (M+H$^+$)

Example 220

H-(D)-Chg-Pro-NH-3-(6-Am)-pico

The Boc group was eliminated from stage c of the above compound under standard conditions. Dihydrochloride: white crystals, melting point 235–238° C. (decomposition); FAB-MS: 387 (M+H$^+$).

Example 221

HOOC—CH$_2$-(D)-Chg-Pro-NH-3-(6-Am)-pico a) H-(D)-Cyclohexylglycylproline (6-cyano-3-picolyl)amide 46.9 g (0.1 mol) of Boc-(D)-cyclohexylglycylproline (6-cyano-3-picolyl)amide (compound 219, stage b) were suspended in 300 ml of ether and, while stirring, 600 ml of HCL-saturated ether were added at room temperature and the mixture was stirred overnight. The suspension was then run into 1.5 l of 15% strength sodium hydroxide solution while stirring and cooling in ice. After addition of 80 ml of $CH_2CH_2$ [sic], the organic phase was separated off and the alkaline phase was extracted 6× with an ether/$CH_2CH_2$ [sic] mixture (7/3). The combined organic phases were dried over $Na_2SO_4$ and evaporated to dryness. 27.2 g of amorphous white powder remained and, according to TLC ($CH_2Cl_2$/MeOH, (4/1) still contained about 5–10% of the amide compound produced by hydrolysis of the cyano group.

b) N-(t-Butoxycarbonylmethyl)-(D)-cyclohexylglycylproline (6-cyano-3-picolyl)amide 14 g (0.072 mol) of t-butyl bromoacetate were added dropwise to a solution of 27.2 g (0.074 mmol) of the above compound (stage a) and 28.6 g (0.22 mol) of diisopropylethylamine in 150 ml of methylene chloride while stirring at room temperature, and the mixture was left to stir overnight.

The reaction solution was washed with water and dried over $Na_2SO_4$, and the residue after removal of the solvent by distillation was chromatographed on a silica gel column with a $CH_2Cl_2$/acetone/MeOH (45/5/1) eluent. 28.6 g (80% of theory) of amorphous white powder were isolated. A sample crystallized from diisopropyl ether with addition of a little ether and melted at 89–91° C.

c) N-t-Butoxycarbonylmethyl-(D)-cyclohexylglycylproline (6-amidino-3-picolyl)amide The above compound was converted into the amidine as in Example 218 stage d). Acetate: white, amorphous powder, FAB-MS: 501 (M+H$^+$)

d) N-(Carboxymethyl)-(D)-cyclohexylglycyl-proline (6-amidino-3-picolyl)amide 2.4 g of the above amidine acetate were dissolved in 50 ml of a $CH_2Cl_2$/$CF_3COOH$ mixture (1/1) and left to stand at room temperature overnight.

The solution was concentrated under reduced pressure, the residue was taken up in methylene chloride, again distilled off with the addition of toluene, and subsequently chromatographed on a silica gel column with methanol/25% strength aqueous ammonia (50/2). After removal of the eluent by distillation, the product was taken up in water and, after treatment with active carbon, lyophilized. The lyophilizate (1.45 g) showed a melting point of 202–205° C., FAB-MS: 445 (M+H$^+$)

Example 222

HOOCCH$_2$-(D)-Chg-Pyr-NH-3-(6-Am)-pico a) 5.2 g (14.75 mmol) of Boc-(D)-Chg-Pyr-OH, 2.88 g (17 mmol) of 6-cyano-3-aminomethylpyridine, 12.2 ml of DIPEA and 17 ml of PPA (50% strength in ethyl acetate) were mixed in 50 ml of DCM at 0° C. The reaction mixture was then allowed to reach room temperature, while stirring, over the course of 1.5 h. For workup, the solution was diluted with 250 ml of ethyl acetate and washed with saturated NaCl solution (3×), 20% strength NaHSO$_4$ (3×) and saturated NaCl solution (1×). The solution was dried with MgSO$_4$ and then ethyl acetate was removed in a rotary evaporator. Crude yield: 7.8 g. The crude product was used without further purification in the next reaction.

Boc-(D)-Chg-Pyr-NH-3-(6-CN)-pico were [sic] introduced into 10 ml of DCM. After the solution had been cooled to 0° C., 20 ml of TFA (50% strength in DCM) were added. The reaction mixture was then allowed to warm to room temperature over the course of 3 h, and the solution was then concentrated in a rotary evaporator. The residue was taken up in toluene, and the solution was concentrated again under reduced pressure. This procedure was repeated once more. Crude yield: 13.5 g.

13.5 g of H-(D)-Chg-Pyr-NH-3-(6-CN)-pico×TFA were introduced into 100 ml of acetonitrile. After addition of 2.69 g of KI, 6.11 g of K$_2$CO$_3$ and 2.87 g of t-butyl bromoacetate, the suspension was stirred at room temperature for 5 h. Subsequently, K$_2$CO$_3$ and KI were removed by filtration, acetonitrile was removed under reduced pressure in a rotary evaporator, and the residue was taken up in ethyl acetate. The solution was washed with water (2×) and saturated NaCl solution (1×), dried with Na$_2$SO$_4$ and concentrated. Crude yield: 6.4 g.

d) 6 g tBuOOCCH$_2$-(D)-Chg-Pyr-NH-3-(6-CN)-pico were dissolved in 42 ml of pyridine and 19.4 ml of TEA and saturated with H$_2$S gas. After the solution had stood at room temperature for 18 hours it was first flushed with nitrogen and then poured into 2 l of ice-water. The aqueous solution was extracted with ethyl acetate (6×), and the combined organic extracts were washed with 5% strength NaHSO$_4$ solution. After drying and concentration, 6.1 g of tBuOOCCH$_2$-(D)-Chg-Pyr-NH-3-(6-CSNH$_2$)-pico crude product remained.

e) 6.1 g of crude tBuOOCCH$_2$-(D)-Chg-Pyr-NH-3-(6-CSNH$_2$)-pico were dissolved in 7.4 ml of MeI and 70 ml of acetone and stirred at room temperature for 4.5 h. The solution was then concentrated, taken up in toluene and again evaporated to dryness in a rotary evaporator. Crude yield: 6.1 g.

f) 6.1 g of tBuOOCCH$_2$-(D)-Chg-Pyr-NH-3-(6-CSMe=NH)-pico were mixed in a one-neck flask with 30 ml of MeOH and 30 ml of methanolic ammonium acetate solution (20% strength) and left to stand at room temperature for 18 h. The solution was concentrated and the residue was taken up in DCM. The organic solution was washed with water (3×20 ml), dried with Na$_2$SO$_4$ and concentrated in a rotary evaporator. After reprecipitation of the crude product from ethyl acetate/diisopropyl ether, 2.7 g of crude product were obtained. The crude product was purified by reversed phase HPLC chromatography. Yield: 0.364 g.

g) 0.28 g of tBuOOCCH$_2$-(D)-Chg-Pyr-NH-3-(6-am)-pico was introduced into 5 ml of dioxane at 0° C. and, after addition of 5 ml of dioxane/HCl, stirred at room temperature for 48 h. The crude product was purified, after concentration of the solution, by column chromatography (MeOH/3% concentrated NH$_3$ solution). Yield: 180 mg. FAB-MS: 443 (M+H$^+$)

Example 223

HOOCCB$_2$-(D)-Chg-2-Phi-NH-3-(6-Am)-pico tBuOOC—CH$_2$-(D)-Chg-2-Phi-NH-3-(6-CN)-pico was prepared starting from Boc-(D)-Chg-2-Phi-OH and 3-aminomethyl-6-cyanopyridine as in Example 222. This intermediate was converted into Example 223 as follows:

a) 8 g (14.9 mmol) of tBuOOC—CH$_2$-(D)-Chg-2-Phi-NH-3-(6-CN)-pico were stirred together with 8 ml of TEA, 2.58 g of hydroxylamine hydrochloride and 90 ml of EtOH at 70° C. for 18 h. Subsequently, the suspension was concentrated, the residue was dissolved in DCM, and the solution was washed 3×with 5 ml of HOAC (30% strength) each time. After drying over Na$_2$SO$_4$, DCM was removed in a rotary evaporator. The N-hydroxyamidine was used without further purification in the next reaction.

b) 5 g of the N-hydroxyamidine were mixed in a reaction flask together with 6 g of Raney nickel, 40 ml of EtOH and 9 ml of HOAc and reduced under a hydrogen atmosphere at 60° C. The crude product was separated by reversed phase HPLC chromatography (acetonitrile/water). Yield 0.7 g.

c) 0.7 g of tBuOOC—CH$_2$-(D)-Chg-2-Phi-NH-3-(6-Am)-pico was converted into the free acid as in Example 222. FAB-MS: 499 (M+H$^+$)

Example 224

HOOC—CH(Me)-(D)-Chg-Pro-NH-3-(6-Am)-pico a) 7.4 g (15.22 mmol) of H-(D)-Chg-Pro-NH-3-(6-CN)-pico×TFA, 6.3 g of K$_2$CO$_3$ and 3.69 g of benzyl 2-bromopropionate was [sic] stirred in 100 ml of acetonitrile at 50° C. for 12 h. After the precursor was completely converted, the solid was filtered off and the filtrate was concentrated. After this, the residue was dissolved in ethyl acetate and washed 2× with water. After the organic solution had dried, the ethyl acetate was removed in a rotary evaporator. Crude yield: 5 g. 3 g of product remained after column chromatography on silica gel.

b) 3 g of BzlOOC—CH(Me)-(D)-Chg-Pro-NH-3-(6-CN)-pico were converted into the corresponding amidine as in Example 223. Yield: 0.8 g.

c) The free acid was obtained by hydrogenation of the benzyl ester under standard conditions. The crude product was purified by reversed phase HPLC chromatography. Yield: 0.4 g. FAB-MS 459 (M+H$^+$)

Example 225

Boc-(D)-Phe-Pro-NH-3-(2-Me-6-Am)-pico

Prepared as in Example 227; melting point 130–140° C.; (hydroacetate)

Example 226

H-(D)-Phe-Pro-NH-3-(2-Me-6-Am)-pico

Prepared as in Example 228; (dihydrochloride) $^{13}$CNMR d$^6$-DMSO δ in ppm: 170.79, 167.62, 161.85, 156.34, 140.72, 138.41, 135.87, 134.53, 129.30, 128.49, 127.29, 120.70, 60.23, 52.18, 46.61, 39.1, 36.48, 29.22, 23.33, 21.72

Example 227

Boc-(D)-Chg-Pro-NH-3-(2-Me-6-Am)-pico a) Preparation of Boc-(D)Chg-Pro-NH-3-(2-Me)-pico 6.4 g of Boc-(D)-Chg-Pro-OH (18.05 mmol) were introduced together with 4.0 g of 2-methyl-3-picolylamine (20.5 mmol, for preparation see Arch. Pharm 308 (1975) 969–76) and 14 ml of DIPEA (81.8 mmol) into 200 ml of DCM and cooled to 5° C. and, at this temperature, 18.8 ml of 50% strength propanephosphonic anhydride solution in ethyl acetate (23.92 mmol) ere added dropwise. After warming to room temperature, reaction was allowed to continue for 1 h, and the mixture was subsequently concentrated under reduced pressure. The residue was taken up in ethyl acetate, and the ethyl acetate phase was extracted about 10 times with water, dried over magnesium sulfate and concentrated in a rotary evaporator. Extraction by stirring of the residue with diisopropyl ether resulted in 7.2 g (87%) of Boc-(D)-Chg-Pro-NH-3-(2-Me)-pico as white solid substance.

Preparation of Boc-(D)-Chg-Pro-NH-3-(2-Me-1-Oxo)-pico 5.3 g of Boc-(D)-Chg-Pro-NH-3-(2-Me)-pico (11.58 mmol) were stirred together with 3.1 g of 98% pure m-chloroperbenzoic acid (18.14 mmol) in 150 ml of DCM at room temperature for 2 h. Subsequently, gaseous ammonia was passed in to saturation, the mixture was stirred at room temperature for 1 h, the precipitate was filtered off with suction and washed with DCM, and the filtrate was again saturated with ammonia. The DCM phase was then washed 3 times with water, dried over magnesium sulfate and concentrated under reduced pressure. 5.5 g of Boc-(D)-Chg-Pro-NH-3-(2-Me-1-Oxo)-pico were obtained as a white solid substance.

c) Preparation of Boc-(D)-Chg-Pro-NH-3-(2-Me-1-MeO)-pico 3.6 g of Boc-(D)-Chg-Pro-NH-3-(2-Me-1-Oxo)-pico (7.58 mmol) were dissolved in 10 ml of DCM, 2.0 ml of dimethyl sulfate (21.1 mmol) in 20 ml of DCM were added, the mixture was stirred at room temperature overnight, the solution was concentrated under reduced pressure and the residue was extracted by stirring with ether 3 times.

4.55 g (100%) of Boc-(D)-Chg-Pro-NH-3-(2-Me-1-MeO)-pico$^\oplus$ CH$_3$OSO$_3$$^\ominus$ were obtained as a white solid substance which was used without further purification in the next reaction.

d) Preparation of Boc-(D)-Chg-Pro-NH-3-(2-Me-6-CN)-pico 4.55 g of Boc-(D)-Chg-Pro-NH-3-(2-Me-1-MeO)-pico$^\oplus$ CH$_3$OSO$_3$$^\ominus$ (7.58 mmol) were dissolved in 10 ml of DMF and, at room temperature, 0.5 g of sodium cyanide (10.02 mmol) dissolved in 30 ml of DMF was added dropwise (slightly exothermic reaction). After stirring at room temperature for one hour, DMF was removed by distillation under reduced pressure (1 mbar), the residue was taken up in 1 M potassium bisulfate solution and extracted with ether, and the organic phases were dried over magnesium sulfate and concentrated under reduced pressure in a rotary evaporator. 2.8 g (76%) of Boc-(D)-Chg-Pro-NH-3-(2-Me-6-CN)-pico were obtained as a white foam.

Preparation of Boc-(D)-Chg-Pro-NH-3-(2-Me-6-Ham)-pico 3.63 g of Boc-(D)-Chg-Pro-NH-3-(2-Me-6-CN)-pico (7.51 mmol) were stirred together with 1.9 g of hydroxylammonium chloride (18.76 mmol) and 6.4 ml of DIPEA (37.525 mmol) in 50 ml of DCM at room temperature for 4 h and then concentrated under reduced pressure in a rotary evaporator, the residue was taken up in ethyl acetate and washed 6 times with dilute hydrochloric acid (pH 4), and the organic phase was dried over magnesium sulfate and concentrated under reduced pressure in a rotary evaporator. 3.8 g (98%) of Boc-(D)-Chg-Pro-NH-3-(2-Me-6-Ham)-pico were obtained as a white solid substance.

f) Preparation of Boc-(D)-Chg-Pro-NH-3-(2-Me-6-Am)-pico 3.8 g of Boc-(D)-Chg-Pro-NH-3-(2-Me-6-Ham)-pico (7.35 mmol) were hydrogenated with two spatula tips of 10% Pd/c [sic] in 80 ml of ethanol and 15 ml of acetic acid at 60° C. for 8 h under slightly elevated pressure, the catalyst was removed by filtration through a glass fiber filter and washed with ethanol, and the filtrate was concentrated under reduced pressure (1 mbar). After the residue had been extracted twice by stirring with ether, 4.0 g (97%) of Boc-(D)-Chg-Pro-NH-3-(2-Me-6-Am)-pico were obtained as a white solid substance. Melting point 144–153; (hydroacetate)

Example 228

H-(D)-Chg-Pro-NH-3-(2-Me-6-Am)-pico 2.8 g of Boc-(D)-Chg-Pro-NH-3-(2-Me-6-Am)-pico× CH$_3$COOH (4.99 mmol) were stirred in 10 ml of DCM and 15 ml of methanol with 25 ml of ethereal hydrochloric acid (>3 M) at room temperature for 4 h. The solution was concentrated under reduced pressure and codistilled several times with DCM, methanol, and the residue was extracted by stirring with ether/DCM and ether/methanol. 2.5 g of H-(D)-Chg-Pro-NH-3-(2-Me-6-Am)-pico×2 HCl were obtained as a white solid substance. Melting point 128–135° C.; (dihydrochloride) $^{13}$C-NMR d$_6$-DMSO, δ in ppm: 170.96, 167.72, 161.86, 156.30, 140.76, 138.53, 135.85, 120.72, 60.56, 55.17, 47.43, 39.20, 38.78, 29.66, 27.75, 25.40, 25.31, 25.20, 23.71, 21.76

Example 229 tBuOOC—CH$_2$-(D)-Chg-Pro-NH-3-(2-Me-6-Am)-pico a) Preparation of H-(D)-Chg-Pro-NH-3-(2-Me)pico 7.8 g of Boc-(D)-Chg-Pro-NH-3-(2-Me)-pico (17.0 mmol) were stirred in 35 ml of DCM and 35 ml of ethereal hydrochloric acid (>3M) at room temperature for 2 h, the solution was concentrated under reduced pressure in a rotary evaporator and codistilled several times with methanol/DCM and the residue was extracted by stirring with ether. 7.3 g (100%) of H-(D)-Chg-Pro-NH-3-(2-Me)-pico×2 HCl were obtained as a white solid substance.

b) Preparation of tBuOOC—CH$_2$-(D)-Chg-Pro-NH-3-(2-Me)-pico 9.4 g of H-(D)-Chg-Pro-NH-3-(2-Me)-pico×2HCl (21.79 mmol) were stirred together with 11.26 g (14.9 ml) of DIPEA (81.16 mmol) and 4.89 g (3.69 ml) of tert-butyl bromoacetate (25.0 mmol) in 150 ml DCM (dried over molecular sieves) at room temperature for 16 h. Since precursor was still present according to TLC, a further 0.4 ml of tert-butyl bromoacetate and 1.5 m [sic] of DIPEA were added and stirring was continued at room temperature for 3 h. The reaction mixture was subsequently concentrated first under waterpump vacuum and then under 1 mbar at max. 40° C. The residue was extracted by stirring with ether, filtered off and washed with ether. The crystals were taken up in water and then extracted at pH 7.5 several times with ethyl acetate, and these ethyl acetate extracts were combined with the above ether filtrate, dried and concentrated under reduced pressure in a rotary evaporator. The residue was taken up in ether and then ethereal hydrochloric acid was added to pH 3, he [sic] precipitate was filtered off with suction, thoroughly washed with ether and extracted by stirring twice more with ether. 9.1 g (82%) of tBuOOC—CH$_2$-(D)-Chg-Pro-NH-3-(2-Me)-pico×HCl were obtained as a white solid substance.

c) Preparation of t-BuOOC—CH$_2$-(Boc)(D)-Chg-Pro-NH-3-(2-Me)-pico 9.5 g of tBuOOC—CH$_2$-(D)-Chg-Pro-NH-3-(2-Me)-pico×HCl (18.66 mmol) were introduced together with 18.66 g of (Boc)$_2$O (18.66 mmol) into 160 ml of DCM and, over the course of 5 min, 5.3 g (7.03 ml) of DIPEA (41.05 mmol) were added, and the mixture was then stirred at room temperature overnight. After further addition of DCM, the solution was washed with 0.5 M HCl solution until DIPEA was no longer present in the DCM (TLC check), then dried over magnesium sulfate and concentrated under reduced pressure in a rotary evaporator. Column chromatography on silica gel with DCM and 0–5% methanol resulted in 5.8 g (54%) of tBuOOC—CH$_2$-(Boc)(D)-Chg-Pro-NH-3-(2-Me)-pico as white solid substance.

d) Preparation of tBuOOC—CH$_2$-(Boc)-(D)-Chg-Pro-NH-3-(2-Me-1-Oxo)-pico 5.8 g of tBuOOC—CH$_2$-(Boc)-(D)-Chg-Pro-NH-3-(2-Me)-pico (10.12 mmol) were stirred together with 9.99 g of 70% pure m-chloroperbenzoic acid (40.5 mmol) in 200 ml of DCM at room temperature for 2 h. Subsequently, gaseous ammonia was passed in to saturation, the mixture was stirred at room temperature for 1 h, the precipitate was filtered off with suction and washed with DCM, and the filtrate was again saturated with ammonia. The DCM phase was then washed 3 times with water, dried over magnesium sulfate and concentrated under reduced pressure. 5.95 g (100%) were obtained.

e) Preparation of tBuOOC—CH$_2$-(Boc)(D)-Chg-Pro-NH-3-(2-Me-1-MeO)-pico$^\oplus$·CH$_3$OSO$_3^\ominus$:

5.95 g of tBuOOC—CH$_2$-(Boc)-(D)-Chg-Pro-NH-3-(2-Me-1-Oxo)-pico (10.12 mmol) were dissolved in 25 ml of DCM, and 28 ml of a 5% strength solution of dimethyl sulfate in DCM were added. After stirring at 40° C. for 5 hours and leaving to stand at room temperature overnight, the mixture was diluted to 100 ml of DCM, rapidly washed 3 times with water, dried over magnesium sulfate and concentrated under reduced pressure in a rotary evaporator. The resulting tBuOOC—CH$_2$-(Boc)-(D)-Chg-Pro-NH-3-(2-Me-1-Meo)-pico$^\oplus$·CH$_3$OSO$_3^\ominus$ was used as crude product in the next reaction.

f) Preparation of tBuOOC—CH$_2$-(Boc)-(D)-Chg-Pro-NH-3-(2-Me-6-CN)-pico

The crude product of tBuOOC—CH$_2$-(Boc)(D)-Chg-Pro-NH-3-(2-Me-1-MeO)-Pico$^\oplus$·CH$_3$OSO$_3^\ominus$ obtained from the above reaction was added dropwise over the course of 20 min to a solution of 1.1 g of sodium cyanide (21.3 mmol) in 50 ml of DMF, maintaining the temperature at 23–25° C. by cooling. After a further 20 min, DMF was removed by distillation under reduced pressure (1 mbar), the residue was taken up in ether and washed successively with water, KHSO$_4$ solution (pH 2), water and saturated brine, and the ether phase was dried over magnesium sulfate and concentrated under reduced pressure in a rotary evaporator. Purification by column chromatography on silica gel (eluent DCM with 0–2% MeOH) resulted in 4.1 g of solid substance which was extracted by stirring with ether. Yield: 4.0 g (66%) of tBuOOC—CH$_2$-(Boc)(D)-Chg-Pro-NH-3-(2-Me-6-CN)-pico g) Preparation of tBuOOC—CH$_2$-(Boc)(D)-Chg-Pro-NH-3-(2-Me-6-Ham)-pico 3.95 g of tBuOOC—CH$_2$-(Boc)(D)-Chg-Pro-NH-3-(2-Me-6-CN)-pico (6.6 mmol) were heated under reflux together with 1.15 g of hydroxylamine hydrochloride (16.52 mmol) and 5.12 g (6.78 ml) of DIPEA (39.6 mmol) in 75 ml of DCM (dried over molecular sieve) for 2 h and subsequently stirred at room temperature overnight. After addition of further DCM, the mixture was washed with dilute hydrochloric acid (pH 4), and the organic phase was dried over magnesium sulfate and concentrated under reduced pressure in a rotary evaporator. The resulting 4.2 g of crude product of tBuOOC—CH$_2$-(Boc)(D)-Chg-Pro-NH-3-(2-Me-6-Ham)-pico were used as crude product in the next reaction.

h) Preparation of tBuOOC—CH$_2$-(Boc)-(D)-Chg-Pro-NH-3-(2-Me-6-Am)-pico 4.2 g of crude product of tBuOOC—CH$_2$-(Boc)(D)-Chg-Pro-NH-3-(2-Me-6-Ham)-pico were hydrogenated in a mixture of 15 ml of acetic acid and 80 ml of ethanol over Pd/C (10%) with hydrogen at 50° C. for 5 h. The catalyst was subsequently filtered off and washed with ethanol, the filtrate was concentrated under reduced pressure (1 mbar) in a rotary evaporator, and the residue was codistilled several times with toluene/DCM, taken up in 100 ml of ether and washed 3 times with 4 ml of water each time. The combined aqueous phases were concentrated under reduced pressure (1 mbar) in a rotary evaporator at max. 35–40° C., and the residue was codistilled with ethanol. 4.2 g of almost pure tBuOOC—CH$_2$-(Boc)-(D)-Chg-Pro-NH-3-(2-Me-6-Am)-pico×CH$_3$COOH (94% over two stages) were obtained as a white solid substance.

i) Preparation of tBuOOC—CH$_2$-(D)-Chg-Pro-NH-3-(2-Me-6-Am)-pico 2.0 g of tBuOOC—CH$_2$-(Boc)(D)-Chg-Pro-NH-3-(2-Me-6-Am)-pico×CH$_3$COOH (2.96 mmol) were stirred in 10 ml of DCM together with 10 ml of ethereal hydrochloric acid (ether saturated with HCl) at room temperature for 1 h 20 min and subsequently concentrated under reduced pressure in a rotary evaporator, and the residue was taken up in water and extracted several times with ethyl acetate. The aqueous phase was concentrated under reduced pressure (1 mbar) in a rotary evaporator at max. 35–40° C. and codistilled several times with acetone. After the resulting mixture had been separated by column chromatography on silica gel (eluent DCM/methanol/acetic acid 100/10/2→100/20/5), 0.7 g of tBuOOC—CH$_2$-(D)-Chg-Pro-NH-3-(2-Me-6-Am)-pico×(HX)$_{1,2}$ (X$^\ominus$ =Cl and/or CH$_3$CO$_2^\ominus$ ) was obtained as a white solid substance which melted above 205° C. with decomposition.

Example 230

HOOC—CH$_2$-(D)-Chg-Pro-NH-3-(2-Me-6-Am)-pico 2.2 g of tBuOOC—CH$_2$-(Boc)-(D)-Chg-Pro-NH-3-(2-Me-6-Am)-pico×CH$_3$COOH (3.25 mmol) were stirred in 30 ml of DCM together with 15 ml of ethereal hydrochloric acid at room temperature for several hours, during which a solid slowly precipitated. The solid was filtered off with suction, extracted by stirring with hot DCM several times and subsequently chromatographed on silica gel (eluent methanol/25% aqueous ammonia solution in the ratio 95/5). 1.3 g (94%) of HOOC—CH$_2$-(D)-Chg-Pro-NH-3-(2-Me-6-Am)-pico were obtained as a white solid substance which melted above 210° C. with decomposition.

Example 231

MeOOC—CH$_2$-(D)-Chg-Pro-NH-3-(2-Me-6-Am)-pico 0.45 g of HOOC—CH$_2$-(D)-Chg-Pro-NH-3-(2-Me-6-Am)-pico (0.1 mmol) were [sic] introduced into 30 ml of methanol (dried over molecular sieves), 1 ml of thionyl chloride was added dropwise, and the mixture was stirred under reflux for 2 h. After addition of a further 0.3 ml of thionyl chloride and stirring under reflux for 1 h, the solution was concentrated under reduced pressure in a rotary evaporator and codistilled several times with methanol/DCM, and the residue was purified by column chromatography on silica gel (eluent: DCM/methanol/acetic acid 100/20/5). After codistillation with toluene several times, 0.38 g of MeOOC—CH$_2$-(D)-Chg-NH-3-(2-Me-6-Am)-pico.(HX)$_{1,2}$ (X$^\ominus$ =Cl and/or CH$_3$COO$^\ominus$ ) was obtained as a white solid subtance which melted at 155–160° C.

Example 232

Boc-(D)-Chg-Pro-NH-2-(5-Am)-pico a) 5-Carboxamido-2-picolylamine 3 g of Raney Ni were added to a solution of 3.5 g (24 mmol) of 2-cyano-5-carboxamidopyridine in 80 ml of methanol and 20 ml of concentrated ammonia, and hydrogenation was carried out at room temperature. Hydrogen uptake was complete after about 7 h.

After removal of the catalyst by filtration with suction, the filtrate was concentrated and the residue was dissolved in 20 ml of 2 N hydrochloric acid and 20 ml of methanol. Addition of 150 ml of ethyl acetate resulted in separation out of the hydrochloride, which was filtered off with suction and dried (3.7 g). The free base melted at 198–202° C.

b) 5-Cyano-2-picolylamine 41 g (0.22 mol) of 5-carboxamido-2-picolylamine were suspended in 150 ml of methanol and 300 ml of methylene chloride, cooled to 10° C. and dissolved by adding 150 ml of triethylamine. A solution of 47.6 g (0.22 mmol) of $(Boc)_2O$ was subsequently added dropwise, and the mixture was stirred at room temperature for 4 h. After the solvent had been stripped off, the residue was mixed with a saturated $K_2CO_3$ solution and extracted 5× with methylene chloride. The combined extracts were dried and the solvent was removed by distillation, with addition of toluene toward the end. 5.4 g of the residue were suspended in 40 ml of dioxane and 15 ml of methylene chloride, 4.3 g of pyridine were added and then, at 0° C., 5.2 g of trifluoroacetic anhydride were added dropwise, resulting in a clear solution. 100 ml of water were added and, after extraction with ethyl acetate, the organic phase was washed with dilute citric acid solution, $NaHCO_3$ solution and water. After drying and stripping off the solvent, a yellow oil (about 5 g) remained, and this was dissolved in 15 ml of isopropanol and 30 ml of ethyl acetate, and 35 ml of ethereal hydrochloric acid solution were added. After standing overnight, the precipitated hydrochloride was filtered off with suction and dried. 4 g of white crystals were isolated. Melting point 230–234° C.

c) Boc-(D)-cyclohexylglycylproline (5-cyano-2-picolyl)amide

Preparation as in Example 219, stage b), by coupling Boc-(D)-cyclohexylglycylproline with 5-cyano-2-picolylamine. White crystals, melting point 128–129° C.

d) Boc-D-Cyclohexylglycylproline (6-amidino-2-picolyl)amide

Amidation of the above compound took place as in Example 218, stage d). Acetate: white crystals, melting point 98–100° C. (decomposition); FAB-MS: 487 (M+H$^+$)

Example 233

H-(D)-Chg-Pro-NH-2-(5-Am)-pico

Compound 233, stage d) was deprotected under standard conditions. Dihydrochloride: white crystals, melting point 233–235° C. (decomposition) FAB-MS: 386 (MH$^+$).

Example 234

HOOC—CH$_2$-(D)-Chg-Pro-NH-2-(5-Am)-pico

The title compound was obtained as in Example 221, stage a), b), c) and d) from Boc-(D)-cyclohexylglycylproline (5-cyano-2-picolyl)amide by elimination of the Boc group, with no amide formation occurring, N-alkylation with t-butyl bromoacetate, amidine formation and acidic hydrolysis of the t-butyl ester. White crystals, melting point 162–4° C., FAB-MS: 445 (MH$^+$)

Example 235

HOOC—CH$_2$-(D)-Chg-Pro-NH-5-(2-Am)-pym a) 2-Thiomethyl-5-aminomethylpyrimidine [sic] hydrochloride 28.1 g (182.2 mmol) of 2-thiomethyl-5-formylpyrimidine [sic] (Z. Arnold et al. J. Heterocyclic Chem. 1991, 28, 1281) were introduced into 880 ml of MeOH/THF (1:1) at −23° C. Addition of 12.8 g (34.3 mmol) of $CeCl_3×7H_2O$ was followed by addition of 5.19 g (137.2 mmol) of sodium borohydride in portions. After a reaction time of 1.5 h, 1.5 l of saturated NaCl solution were added to the reaction solution, and the mixture was extracted with DCM (4×130 ml). The combined organic phases were dried and concentrated under reduced pressure. Yield: 26.9 g.

26.89 g (172.14 mmol) of 2-thiomethyl-5-hydroxymethylpyrimidine [sic] were dissolved in 390 ml of DCM (abs.) and, after addition of 1 drop of DMF and 27 ml (370.37 mmol) of $SOCl_2$, stirred at 0° C. for 45 min. For workup, the reaction solution was evaporated to dryness.

The 2-thiomethyl-5-chloromethylpyrimidine [sic] obtained in this way was stirred together with 16.79 g (258.2 mmol) of $NaN_3$ in 84 ml of DMSO at room temperature overnight. Because conversion was incomplete, a further 4.2 g of $NaN_3$ were added. After a further reaction time of 2 h, the chloride derivative had completely reacted. For workup, the reaction mixture was poured into 300 ml of water, and the aqueous phase was extracted with $Et_2O$ (5×100 ml). The combined organic extracts were washed with water (3×25 ml) and dried, subsequently the ether was almost completely removed under reduced pressure.

The concentrated ethereal 2-thiomethyl-5-azidomethylpyrimidine [sic] solution was dissolved in 28 ml of THF and cautiously added to a solution of 45.15 g (172.1 mmol) of $Ph_3P$ in 84 ml of THF while cooling in ice. After 15 min, the ice cooling was removed, 4.65 ml of water were added to the reaction mixture and the reaction solution was stirred at RT for 18 h. For workup, the reaction mixture was evaporated to dryness under reduced pressure, and the resulting residue was taken up in 70 ml of 3N HCl. The aqueous solution was washed with ethyl acetate/$Et_2O$ (1/1; 4×50 ml). The solution was subsequently adjusted to pH 9 with $Na_2CO_3$ and extracted with DCM (12×50 ml). The combined organic extracts were dried and concentrated. The residue was dissolved in DCM/ethyl acetate, and the free amine was precipitated as hydrochloride with dioxane/HCl. Yield: 30.48 g. 1H-NMR (d$_6$-DMSO, δ in ppm): 2.55 (s, 3H, CH3); 4.1 (q, 2H, N—CH$_2$); 8.8 (s, 2H, Ar—H); 10.8 (sb, NH)

b) Boc-Pro-NH-5-(2-SMe)-pym 12.9 g (60 mmol) of Boc-Pro-OH were introduced together with 15 g (65.8 mmol) of 2-thiomethyl-5-aminomethylpyrimidine [sic] hydrochloride and 61.4 ml (359 mmol) of DIPEA into 150 ml of DCM at 0° C. After addition of 63.4 ml of PPA (50% strength in ethyl acetate), the reaction mixture was stirred at 0° C.—room temperature for 6 h. After the Boc-Pro-OH was completely reacted (TLC check: DCM/MeOH 95:5), the reaction mixture was taken up in 300 ml of ethyl acetate. The organic phase was washed with 20% strength sodium bisulfate solution (2×), water (2×) and saturated NaCl solution. The organic phase was dried with sodium sulfate and then ethyl acetate was removed under reduced pressure. 16.7 g of the required product remained.

c) Boc-Pro-NH-5-(2-SO$_2$Me)-pym 20.5 g (58.1 mmol) of Boc-Pro-NH-5-(2-SMe)-pym were introduced into 700 ml of DCM at room temperature. Then 42.94 g (174 mmol) of m-CPBA were added in portions over the course of 30 min. to the solution. After a total reaction time of 2 h, the reaction mixture was extracted with 20% strength NaHSO$_4$ (2×), 5% strength NaHCO$_3$ solution (6×)

and 20% strength $Na_2S_2O_5$ solution (3x). After the solution had been dried and the DCM had been removed, 21.7 g of the sulfone Boc-Pro-NH-5-(2-$SO_2$Me)-pym remained.

d) Boc-Pro-NH-5-(2-CN)-pym 21.7 g (56.4 mmol) of Boc-Pro-NH-5-(2-$SO_2$Me)-pym were dissolved in 30 ml of DMSO and, after addition of 2.84 g of NaCN, stirred at room temperature overnight. The solution was then poured into 150 ml of water, and the aqueous solution was extracted with DCM (5x100 ml). The combined organic phases were washed with saturated NaCl solution (5x) and water (2x). Drying and concentration of the organic solution resulted in 15.3 g of the required cyanide.

e) H-Pro-NH-5-(2-CN)-pymx3 TFA 13.98 g (42.1 mmol) of Boc-Pro-NH-5-(2-CN)-pym were introduced into DCM. After addition of 13 ml (170 mmol) of TFA, this solution was stirred at room temperature until the precursor had completely reacted (TLC check). The required salt remained after concentration of the solution under reduced pressure and was used further in the next reactions without further purification.

f) H-(D)-Chg-Pro-NH-5-(2-CN)-pymx3 TFA 10 mmol of H-Pro-NH-5-(2-CN)-pymx3 TFA, 2.44 g (9.5 mmol) of Boc-D-Chg-OH and 9.8 ml (57 mmol) of DIPEA were introduced at 0° C. After addition of 10.1 ml of PPA (50% strength in ethyl acetate), the reaction mixture was stirred while reaching room temperature over the course of 6 h. For workup, it was diluted with 300 ml of ethyl acetate, and the organic phase was washed with 20% strength sodium bisulfate solution (2x), water (2x) and saturated NaCl solution. The organic phase was dried with sodium sulfate and then ethyl acetate was removed under reduced pressure. 4.74 g of the required product remained. The crude product obtained in this way was converted as described above into the corresponding trifluoroacetic acid salt.

g) tBuOOC—$CH_2$-(D)-Chg-Pro-NH-5-(2-CN)-pym 4.1 g (11.07 mmol) of H-(D)-Chg-Pro-NH-5-(2-CN)-pymx3 TFA were stirred together with 1.68 g (12.17 mmol) of potassium carbonate and 1.63 ml (11.07 mmol) of t-butyl bromoacetate at RT. After reaction was complete, the potassium carbonate was filtered off and the filtrate was concentrated in a rotary evaporator. The residue was dissolved in ethyl acetate, and the organic solution was washed with sodium bicarbonate solution (5% strength) and saturated sodium chloride solution. The solvent was then removed under reduced pressure (crude yield: 3.66 g). The crude product was purified by column chromatography (DCM/MeOH 98/2+0.5% conc. $NH_3$ solution). 1.3 g of the pure product were obtained.

h) tBuOOC—$CH_2$-(D)-Chg-Pro-NH-5-(2-Am)-pym 1.3 g (2.68 mmol) of tBuOOC—$CH_2$-(D)-Chg-Pro-NH-5-(2-SMe)-pym were dissolved in 15 ml of EtOH and, after addition of 0.5 g (6.71 mmol) of hydroxylammonium chloride and 2.5 ml of DIPEA, stirred at 60° C. for 4 h. The reaction mixture was concentrated in a rotary evaporator and taken up in DCM. After the organic solution had been washed with a little water, dried and concentrated, the crude product was redissolved in EtOH and, after addition of Raney nickel, hydrogenated under a hydrogen atmosphere at 60° C. for 4 h. After removal of the Raney nickel by filtration, the ethanolic solution was concentrated and the crude product was purified by column separation on silica gel (DCM/MeOH/50% HOAc 40/10/2). Yield: 250 mg.

i) HOOC—$CH_2$-(D)-Chg-Pro-NH-5-(2-Am)-pym 250 mg of tBuOOC—$CH_2$-(D)-Chg-Pro-NH-5-(2-Am)-pym were cleaved to the acid with TFA/DCM and the crude product was purified by column chromatography (MeOH/3% conc. $NH_3$). Yield: 108 mg. MS: 446 (M+H$^+$), 369

Example 236

(D)-Man-Pro-NH-4-(1-Am)-pip

A solution of 4.2 g (12.6 mmol) of O-tetrahydropyranyl-(D)-2-phenyl-2-hydroxyacetyl-(L)-proline (WO 93/18060) in 40 ml of THF was, after addition of 1.9 g (12.6 mmol) of 1-hydroxybenzotriazole and 3.3 g (25 mmol) of dicyclohexylcarbodiimide, stirred at room temperature for 4 h. The precipitated urea was filtered off with suction and washed with a little THF. To this filtrate was added, at 5° C., a solution of 2.9 [lacuna] (12.6 mmol) of 1-amidino-4-aminomethylpiperidine dihydrochloride and 1.6 g of sodium bicarbonate in 6 ml of water. After stirring at room temperature for 48 h, the solvent was substantially removed by distillation, the residue was taken up in ethanol, insolubles were removed by filtration, and the solution was again concentrated. The residue was purified on a silica gel column with a $CH_2Cl_2$/MeOH/50% strength acetic acid mixture (45/5/1.5). The eluate of the pure fractions was distilled off, adding toluene toward the end, and the residue was recrystallized from 50 ml of acetone with the addition of a little water. 3.5 g of acetate were isolated in the form of white crystals, melting point 199–202° C. (decomposition); FAB-MS: 388 (M+H$^+$).

Example 239

Boc-(D)-Phe-Pro-NH-(2-MeO)-pAmb a) Boc-Pro-(4-cyano-2-methoxy)benzylamide 16.0 g of Boc-proline (50 mmol), dissolved in 80 ml of THF, were stirred with 5.7 g of hydroxysuccinimide and 10.2 g of DCC at 0° C. for 30 min. Subsequently 8.0 g (50 mmol) of 4-aminomethyl-3-methoxybenzonitrile, dissolved in 50 ml of THF, were added dropwise at 0° C., and the mixture was stirred at RT for 20 h. The solid was filtered off, and the filtrate was mixed with the same volume of ethyl acetate and washed with cold 5% strength $NaHSO_4$ solution and saturated NaCl solution. 11.5 g (65%) of product were obtained. $^1$H-NMR (DMSO-d$_6$; δ in ppm): 8.38 (m, NH); 7.50–7.35 (m, 3H);

4.40–4.05 (m, 3H, N—C$\underline{H}_2$—Ar/N—C$\underline{H}$—CO); 3.87 (s, OC$\underline{H}_3$); 3.50–3.25 (m, 2H, N—C$\underline{H}_2$); 2.2.5 [sic]–2.00 (m, 1H); 1.90–1.65 (m, 3H); 1.40 and 1.30 (2s; 9H)

b) H-Pro-(4-cyano-2-methoxy)benzylamide 11.4 g (31.7 mmol) of Boc-proline (2-methoxy-4-cyano)-benzylamide were dissolved in 130 ml of DCM and saturated with HCl gas at 0–5° C. After 2 h, the Boc group was completely eliminated. The solvent was removed under reduced pressure, and the product was used in the next reactions without further purification. $^1$H-NMR (DMSO-d$_6$, δ in ppm): 10.25 (s, 1H); 8.60 (s, 1H); 7.50 (d, 1H); 7.42 (dd, 1H); 7.39 (d, 1H); 4.40–4.20 (m, 3H); 3.88 (s, 3H); 3.20 (m, 2H); 2.35 (m, 1); 2.00–1.80 (m, 3H)

c) Boc-(D)-Phe-Pro-(4-cyano-2-methoxy)benzylamide 3.54 g (13.35 mmol) of Boc-(D)-Phe-Pro-OH, 9.9 ml of DIPEA and 4.80 g (13.35 mmol) of H-Pro-(4-cyano-2- methoxy)benzylamide hydrochloride were mixed at −5° C. with 11.1 ml (15.0 mmol) of PPA (50% strength in ethyl acetate) in 100 ml of DCM and stirred at 0° C. for 2 h. The reaction mixture was washed successively with 1N NaOH, 1N HCl and saturated brine and dried over $Na_2SO_4$. Stripping of the solvent resulted in 6.5 g (96%) of the product. $^1$H-NMR (DMSO-$d_6$, δ in ppm): 8.75/7.88 (1H, NH (2 rotamers)), 7.5–7.1 (9H, aromatic H and NH), 4.4–4.1 (4H, $CH_2$ and 2×CH), 3.85 (3H, $OCH_3$), 3.7–3.4 (2H, $CH_2$), 3.0–2.7 (2H, $CH_2$), 2.3–1.5 (4H, 2×$CH_2$), 1.3–1.1 (9H, Boc)

d) Boc-(D)-Phe-Pro-(4-amidino-2-methoxy) benzylamide

The nitrile from the preceding stage was converted into 4.6 g of amidine hydroiodide as in A.III.1. $^1$H-NMR (DMSO-$d_6$, δ in ppm): 9.25/8.85 (4H, amidine), 8.75/7.95 (1H, NH (2 rotamers)), 7.4–7.1 (9H, aromatic H and NH), 4.45–4.10 (4H, $CH_2$ and 2×CH), 3.90 (3H, $OCH_3$), 3.65–ca. 3.4 (2H, $CH_2$), 3.0–2.7 (2H, $CH_2$), 1.95–1.55 (4H, 2×$CH_2$, 1.3–1.2 (9H, Boc)

Example 240

H-(D)-Phe-Pro-NH-(2-MeO)-pAmb

The amidine hydroiodide (Example 239) was converted into the amidine hydroacetate on an acetate ion exchanger (IRA 420) and then dissolved in 50 ml of DCM and saturated with HCl gas at 0° C. After 1 h, the solvent was stripped off. 3.0 g of the amidine were obtained as dihydrochloride. $^1$H-NMR (DMSO-$d_6$, δ in ppm): 9.50/9.27 (4H, amidine), 8.80 (3H, $NH_3^+$), 8.75 (1H, NH), 7.50–7.20 (8H, aromatic H), 4.35–4.10 (4H, $CH_2$ and 2×CH), 3.90 (3H, $OCH_3$), ca. 1.9–1.35 (4H, 2×$CH_2$)

Example 241

Boc-(D)-Phe(4-MeO)-Pro-NH-(2-MeO)-pAmb a) Boc-(D)-Phe(4-MeO)-Pro-(4-cyano-2-methoxy) benzylamide 1.55 g (5.25 mmol) of Boc-(D)-Phe(4-OMe)-OH, 3.9 ml of DIPEA and 1.55 g (5.25 mmol) of proline (2-methoxy-4-cyano)benzylamide hydrochloride were mixed at −5° C. with 4.4 ml (5.9 mmol) of PPA (50% strength in ethyl acetate) in 35 ml of DCM and stirred at 0° C. for 1 h. The reaction mixture was washed successively with 1N NaOH, 1N HCl and saturated brine and dried over $Na_2SO_4$. After the solvent was stripped off, 2.4 g of solid remained. $^1$H-NMR (DMSO-$d_6$, δ in ppm): 8.72 and 7.87 (t, 2H); 7.42 (1H);

7.35 (m, 3H); 7.15 (d, 2H); 6.85 (d, 2H); 7.00/6.70 (2d, 1H (2 rotamers)) 1H; 4.40–4.10 (m, 4H); 3.85 (s, 3H); 3.70 (s, 3H); 3.05–2.55 (m, 2H); 1.95–1.55 (m, 4H); 1.2 (s, 9H)

b) Boc-(D)-Phe(4-MeO)-Pro-NH-(2-MeO)-pAmb 2.4 g of the nitrile (Example 241/a) were converted as in A.III.1. after purification by column chromatography on silica gel (mobile phase: DCM/MeOH 9:1) into 1.7 g of the amidine hydroiodide. $^1$H-NMR (DMSO-$d_6$, δ in ppm): 9.25/8.85 (4H, amidine), 7.95 (1H, NH), 7.4–6.8 (8H, aromatic H and NH), 4.4–4.1 (4H, $CH_2$ and 2×CH), 3.90/3.70 (6H, 2×$OCH_3$), ca. 3.7–2.9 (2H, $CH_2$), 3.0–2.6 (2H, $CH_2$), 1.9–1.5 (4H, 2×$CH_2$), 1.3–1.2 (9H, Boc)

Example 242

H-(D)-Phe(4-MeO)-Pro-NH-(2-MeO)-pAmb 1.7 g the amidine hydroiodide (Example 241) were converted into the acetate on an acetate ion exchanger (IRA 420) and then the Boc group was eliminated as in Example 240. 1.0 g of the dihydrochloride was obtained. $^1$H-NMR (DMSO-$d_6$, δ in ppm): 9.50/0.25 (4H, amidine), 8m85–8.65 (4H, NH and $NH_2^+$), 7.50–7.30 and 7.15/6.90 (7H, aromatic H), 4.28–4.05 (4H, $CH_2$ and 2×CH), 3.90/3.75 (6H, 2×$OCH_3$), 3.20–2.85 (2H, $CH_2$), 1.95–1.40 (4H, 2×$CH_2$); FAB-MS: 454 (M+H$^+$)

Example 243

HOOC—$CH_2$-(D)-Phe(4-MeO)-Pro-NH-(2-MeO)-pAmb

The Boc group in the compound from Example 241 a) was cleaved as in Example 240. 3.5 g of this cleavage product were dissolved in 80 ml of DCM and stirred together with 4.45 ml of DIPEA and 1.09 ml of tert-butyl bromoacetate at room temperature for 3 days. The product was worked up as in Example 246 a). 3.0 g of the resulting compound tBuOOC—$CH_2$-(D)-Phe(4-MeO)-Pro-(2-methoxy-4-cyano)benzylamide were reacted as in Example 246 b) with hydroxylamine hydrochloride, and 3.1 g of the resulting hydroxyamidine were hydrogenated with 185 mg of Raney nickel in 65 ml of methanol to which 0.31 ml of glacial acetic acid was added, at 50° C., to give the amidine hydroacetate. The catalyst was filtered off and the tBuOOC—$CH_2$-(D)-Phe(4-MeO)-Pro-(2-MeO)-pAmb hydroacetate was purified by column chromatography on silica gel (mobile phase: DCM +10% methanol +2% (50% strength) acetic acid). 1.3 g of the tert-butyl ester were obtained (FAB-MS: 568 (M+H$^+$)) and 1.15 g thereof were converted as in Example 246 d) into 850 mg of HOOC—$CH_2$-(D)-Phe(4-MeO)-Pro-NH-(2-MeO)-pAmb. $^1$H-NMR (DMSO-$d_6$, δ in ppm): 9.9–9.7 and 9.2–9.0 (2H, $NH_2^+$), 9.60/9.35 (4H, amidine), 7.50–6.73 (5H, aromatic H), 4.50–3.45 (8H, 3×$CH_2$ and 2×CH), 3.90 (3H, $OCH_3$), 3.73 (3H, $OCH_3$), 3.40–3.27 and 3.06–2.87 (2H, $CH_2$), 2.43–1.25 (4H, 2×$CH_2$)

Example 244

Boc-(D)-Chg-Pro-NH-(2-MeO)-pAmb a) Boc-(D)-Cyclohexylglycylproline (2-methoxy-4-cyano)benzylamide 20.8 ml of DIPEA (121 mmol), 4.58 g (28.2 mmol) of 2-methoxy-4-cyanobenzylamine and 25 ml of PPA (50% strength solution in ethyl acetate) were added to 10.0 g (28.2 mmol) of Boc-(D)-Chg-Pro-OH in 70 ml of absolute dichlormethane at −5° C. and stirred at 0° C. for 2 h. The solution was subsequently washed successively with 0.5 N sodium hydroxide solution, 1N HCl and saturated brine and dried with $Na_2SO_4$, and the solvent was completely stripped off under reduced pressure. The product which resulted in virtually quantitative yield was reacted without further purification in the next steps. $^1$H-NMR (DMSO-$d_6$, δ in ppm): 7.9 (1H, NH), 7.45 and 7.35 (3H, aromatic H), 7.1 (1H, NH), 4.45–3.50 (6H, 2×$CH_2$ and 2×CH), 3.86 (3H, $OCH_3$), 2.2–1.0 (24H, cyclohexyl+2×$CH_2$+Boc)

b) Boc-(D)-Cyclohexylglycylproline (2-methoxy-4-hydroxyamidino)benzylamide 12.0 g (24 mmol) of the cyano precursor (a) were reacted with hydroxylamine hydrochloride as in Example 246 b). The product precipitated virtually quantitatively as voluminous precipitate. $^1$H-NMR (DMSO-$d_6$, δ in ppm): 9.7–9.5 (1H, OH), 5.8 (2H, $NH_2$)

c) Boc-(D)-Cyclohexylglycyl-proline (2-methoxy-4-amidino)benzylamide

The hydroxyamidino compound (b) was hydrogenated with Raney nickel as in Example 243. The product was purified by column chromatography on silica gel (mobile phase: dichloromethane/10%–20% MeOH/2% (50% strength) acetic acid). 10.5 g of the amidine were obtained as acetate (yield: 75%—starting from the nitrile (a)); $^1$H-NMR (DMSO-d$_6$, δ in ppm): the amidino group shows as acetate an extremely broad signal from about 10–8 ppm; 7.95 (1H, NH), 7.4–7.3 (3H, aromatic H), 7.05 (1H, NH), 4.4–3.4 (6H, 2×CH$_2$ and 2×CH), 3.89 (3H, OCH$_3$), 2.2–1.0 (24H, cyclohexyl+2×CH$_2$+Boc)

Example 245

H-(D)-Chg-Pro-NH-(2-MeO)-pAmb 10.5 g of Boc-(D)-Chg-Pro-(2-methoxy-4-amidino) benzylamide were dissolved in 200 ml/10 ml of absolute dichloromethane/MeOH and HCl was passed in at 0–5° C. for 1 h. After stirring at 0° C. for a further hour, the solvent was completely stripped off under reduced pressure to result in 7.6 g (86%) of the product as dihydrochloride. $^1$H-NMR (DMSO-d$_6$, δ in ppm):9.60 and 9.33 (4H, amidine), 8.87 (1H, NH), 8.62 (3H, NH$_3^+$), 7.5–7.3 (3H, aromatic H), 4.45–4.15 (4H, CH$_2$ and 2×CH), 3.95 (3H, OCH$_3$), 3.95–3.82 (1H, CH$_2$), 3.65–3.55 (1H, CH$_2$), 2.2–1.0 (15H, cyclohexyl and 2×CH$_2$)

Example 246

HOOC—CH$_2$-(D)-Chg-Pro-NH-(2-MeO)-pAmb

(a) N-tert-Butyloxycarbonylmethyl-(D)-cyclohexylglycylproline (2-methoxy-4-cyano) benzylamide 0.72 g (1.65 mmol) of H-(D)-Chg-Pro-(2-methoxy-4-cyano)benzylamide hydrochloride was introduced into 30 ml of absolute dichloromethane. 1 ml (5.8 mmol) of DIPEA was added and then a solution of 1.65 mmol of tert-butyl bromoacetate and 15 ml of dichloromethane was added dropwise at room temperature in min. The reaction mixture was stirred at room temperature for 3 days and then washed successively with 0.5 N sodium hydroxide solution, 0.5 NHCl [sic] and saturated brine. Drying resulted in 0.7 g of the crude product which was used without further purification in the next steps.

(b) N-tert-Butyloxycarbonylmethyl-(D)-cyclohexylglycylproline (2-methoxy-4-hydroxyamidino)benzylamide 1.45 g (2.8 mmol) of the 2-methoxy-4-cyanobenzylamide (a) were dissolved in 20 ml of 1:1 dichloromethane/MeOH and stirred together with 0.49 g (7.1 mmol) of hydroxylamine hydrochloride and 2.8 ml of DIPEA at room temperature for 20 h. After the solvent had been stripped off, the product was taken up in dichloromethane, washed with water and saturated brine and dried. 1.2 [lacuna] of crude product were obtained and were immediately used further.

(c) N-tert-Butyloxycarbonylmethyl-(D)-cyclohexylglycylproline (2-methoxy-4-amidino) benzylamide The hydroxyamidino compound (b) was hydrogenated with Raney nickel as in Example 243. After purification by column chromatography on silica gel (mobile phase: dichloromethane/10%–20% MeOH/2% (50% strength) acetic acid), 0.5 g of product was obtained as acetate.

d) N-Hydroxycarbonylmethyl-(D)-cyclohexylglycyl-proline (2-methoxy-4-amidino)benzylamide 0.5 g (0.85 mmol) of the amidino acetate (c) was dissolved in ml of absolute dichloromethane. HCL gas was passed in at 0–50° C. until the solvent was saturated. After 40 min, stirring was continued at room temperature for one hour. After the solvent had been stripped off under reduced pressure, 370 mg of pure product were obtained as dihydrochloride. $^1$H-NMR (DMSO-d$_6$, δ in ppm): 9.57 and 9.33 (4H, amidine); 9.8–9.1 (2H, NH$_2^+$), 7.6–7.3 (3H, aromatic H); 4.5–4.1 (4H, 1×CH$_2$ and 2×CH); 3.93 (3H, OCH$_3$), 3.9–3.4 (4H, 2×CH$_2$), 2.3–1.0 (15H, cyclohexyl and 2×CH$_2$)

Example 247

Boc-(D)-Chg-Aze-NH-(2-MeO)-pAmb

(a) Boc-(L)-Azetidine-2-carboxylic acid (2-methoxy-4-cyano)-benzylamide 1.22 g (10.5 mmol) of hydroxysuccinimide and 2.18 g (10.5 mmol) of DCC were added to 2.12 g of Boc-(L)-azetidine-2-carboxylic acid (10.5 mmol) in 50 ml of THF at 0–50° C., and the mixture was stirred for 30 min. Then, at 0–5° C., 2.10 g (10.5 mmol) of 2-methoxy-4-cyanobenzylamine hydrochloride and finally 1.48 ml of Et$_3$N were added. The reaction mixture was stirred at room temperature overnight. The precipitated urea was removed on a suction filter funnel, and the filtrate was taken up in ethyl acetate and washed successively with 0.5 N HCl, 0.5 N sodium hydroxide solution and saturated brine. The solvent was dried over Na$_2$SO$_4$ and then completely stripped off under reduced pressure. 3.1 g (85%) of product were obtained and were used without further purification. $^1$H-NMR (DMSO-d$_6$, δ in ppm): 8.5 (1H, NH); 7.48 and 7.40–7.25 (3H, aromatic H); 4.55 (dd, 1H, CH); 4.45–4.15 (2H, CH$_2$), 3.88 (3H, OCH$_3$), 3.9–3.7 (2H, CH$_2$), 2.5–2.3 (1H, CH$_2$); 2.15–1.95 (1H, CH$_2$); 1.35 (9H, Boc)

(b) (L)-Azetidine-2-carboxylic acid (2-methoxy-4-cyano)benzylamide 3.0 g (8.7 mmol) of Boc-Aze-(2-methoxy-4-cyano) benzylamide were converted in almost quantitative yield into the required product (b) as in Example 239 (b). $^1$H-NMR (DMSO-d$_6$, δ in ppm): 10.0–9.85 (1H, NH$_2^+$), 7.50 and 7.45–7.35 (3H, aromatic H); 5.10–4.95 (1H, CH); 4.35 (d, 2H, CH$_2$); 4.05–3.65 (2H, CH$_2$); 3.89 (3H, OCH$_3$); 2.8–2.6 (1H, CH$_2$); 2.5–2.3 (1H, CH$_2$)

(c) Boc-(D)-Cyclohexylglycyl-(L)-azetidine-2-carboxylic acid (2-methoxy-4-cyano)benzylamide 2.2 g of Boc-(D)-Chg-OH were reacted as in Example 241 (a) with 2.4 g of H-Aze-(2-methoxy-4-cyano-)benzylamide hydrochloride. 3.5 g were obtained.

(d) Boc-(D)-Cyclohexylglycyl-(L)-azetetine-2-carboxylic [sic] acid (2-methoxy-4-amidino) benzylamide 3.4 g of the nitrile (c) were reacted with hydroxylamine hydrochloride as in Example 246 (b), and the resulting hydroxyamidine was hydrogenated with Raney nickel as in Example 243. 3.1 g of the amidine were obtained as hydroacetate.

Example 248

H-(D)-Chg-Aze-NH-(2-MeO)-pAmb 3.1 g of the Boc compound (Example 247) were cleaved to the dihydrochloride as in Example 245. $^1$H-NMR (DMSO-d$_6$, δ in ppm): 9.45/9.20 (4H, amidine); 9.0 (1H, NH); 8.55 (3H, NH$_3^+$); 7.45/7.40 (3H, aromatic H); 4.75–4.10 (4H, CH$_2$ and 2×CH); 3.90 (3H, OCH$_3$), 2.7–1.0 (13 H, cyclohexyl and CH$_2$)

Example 249

Boc-(D)-Chg-Pro-NH-(2-iPrO)-pAmb 4.1 g (11.5 mmol) of Boc-(D)-Chg-Pro-OH were reacted as in Example 239 (a) with one equivalent each of hydroxysuccinimide, DCC, 4-aminomethyl-3-isopropoxy-benzonitrile hydrochloride and Et$_3$N. 5.7 g (94%) of crude product were obtained and were used without further purification in the next steps. $^1$H-NMR (DMSO-d$_6$, δ in ppm): 7.85 (1H, NH); 7.43 and 7.30 (3H, aromatic H); 7.08 (1H, NH); 4.80–3.50 (7H, 2×CH$_2$, 3×CH); 2.2–1.0 (30H, Boc+ cyclohexyl+2×CH$_3$+2×CH$_2$)

Example 250

H-(D)-CHg-Pro-NH-(2-iPro)-pAmb 5.7 g of the Boc compound (Example 249) were reacted as in Example 246 (b) with hydroxylamine hydrochloride, and the resulting hydroxyamidine was hydrogenated with Raney nickel as in Example 243. The resulting amidine hydroacetate was cleaved as in Example 245. 3.1 g of the product were obtained as dihydrochloride. $^1$H-NMR (DMSO-d$_6$, δ in ppm): 9.40/9.15 (4H, amidine); 8.75 (1H, NH); 8.55 (3H, NH$_3^+$); 7.40–7.25 (3H, aromatic H); 4.80 (1H, CH); 4.4–3.5 (6H, 2×CH$_2$ and 2×CH); 2.3–1.0 (15H, cyclohexyl and 2×CH$_2$), 1.3 (6H, 2×CH$_3$)

Example 251

Boc-(D)-Chg-Pro-NH-(2-Cl)-pAmb (a) Boc-Proline (2-chloro-4-cyano)benzylamide 5.4 g (24 mmol) of Boc-Pro-OH were reacted as in Example 244 (a) with 20 ml of PPA, 17.9 ml of DIPEA and 4.0 g (24 mmol) of 2-chloro-4-cyanobenzylamine to give Boc-Pro-(2-chloro-4-cyano)benzylamide. 7.0 g (80%) of product were obtained. $^1$H-NMR (DMSO-d$_6$, δ in ppm): 8.57 (1H, NH); 8.05–7.45 (3H, aromatic H); 4.50–4.10 (3H, CH$_2$ and CH); 3.4–3.2 (2H, CH$_2$); 2.25–1.70 (4H, 2×CH$_2$); 1.4–1.3 (9H, Boc)

(b) Proline (2-chloro-4-cyano)benzylamide hydrochloride

The Boc group was eliminated as in Example 239 (b). 5.6 g (97%) of the hydrochloride were obtained. $^1$H-NMR (DMSO-d$_6$, δ in ppm): 10.2 and 8.6 (NH$_2^+$), 9.45 (1H, NH); 8.05–7.50 (3H, aromatic H); 4.45 (d, 2H, CH$_2$); 4.28 (1H, CH); 3.20 (2H, CH$_2$), 2.40–1.80 (4H, 2×CH$_2$)

c) Boc-(D)-Cyclohexylglycyl-proline (2-chloro-4-cyano)benzylamide 4.76 g (18.7 mmol) of Boc-(D)-cyclohexylglycine were reacted as in Example 241 (a) with 15.5 ml of PPA, 14 ml of DIPEA and 5.6 g (18.7 mmol) of the hydrochloride (b) to give Boc-(D)-Chg-Pro-(2-chloro-4-cyano)benzylamide. 8.7 g (92%) of product were obtained.

(d) Boc-(D)-Cyclohexylglycylproline (2-chloro-4-hydroxyamidino)benzylamide

The cyano group in substance (c) was reacted as in Example 246 (b) with hydroxylamine to give Boc-(D)-Chg-Pro-(2-chloro-4-hydroxyamidine)benzylamide [sic] in virtually quantitative yield. 4.6 g of product were obtained. $^1$H-NMR (DMSO-d$_6$, δ in ppm): 9.75 (1H, OH); 5.90 (2H, NH$_2$)

(e) Boc-(D)-Cyclohexylproline (2-chloro-4-amidino)benzylamide 4.6 g of the hydroxyamidine (d) were hydrogenated to the amidine with Raney nickel as in Example 243. Purification by column chromatography on silica gel (mobile phase: dichloromethane/15% MeOH/2% (50% strength) acetic acid) resulted in 5.4 g of the amidine as acetate. $^1$H-NMR (DMSO-d$_6$, $^1$H-NMR (DMSO-d$_6$, δ in ppm): the signal of the amidine as acetate could not be located because of its width; 8.15 (1H, NH), 7.9–7.5 (3H, aromatic H), 7.05 (1H, NH), 4.5–3.4 (6H, 2×CH$_2$ and 2×CH), 2.2–1.0 (24, cyclohexyl+2×CH$_2$+Boc)

Example 252

H-(D)-Chg-Pro-NH-(2-Cl)-pAmb

The Boc group was eliminated from Example 251 as in Example 245. 3.0 g (65%) of the product were obtained as dihydrochloride. $^1$H-NMR (DMSO-d$_6$, δ in ppm): 9.55 and 9.34 (4H, amidine), 9.05 (1H, NH), 8.60 (3H, NH$_3^+$), 7.95–7.48 (3H, aromatic H), 4.5–3.5 (6H, 2×CH$_2$, 2×CH), 2.25–1.0 (15H, cyclohexyl+2×CH$_2$)

Example 253

H-(D)-Phe-Pro-(D,L)(4-Am)-PhgOMe

The compound was prepared by elimination of Cbz from Example 18. $^1$H-NMR (d$_6$-DMSO, δ in ppm): 9/9.2/8.85/8.8 (4d, 1H, NH); 7.8 (m, 2H, Ar—H); 7.6 (m, 2H, Ar—H); 7.3–7.0 (m 5H, Ar—H); 5.7/5.6 (2d, 1H, α-H); 4.8/4.4 (2dd, 1H, α-Phe); 3.9 (m 1H, α-Pro); 3.75 (2s, 3H, OCH$_3$); 3.6 (2H, δ-Pro); 3.0–2.6 (m, 2H, CH$_2$-Ph); 2.2–1.6 (m, 4H, β/γ-Pro) MS: 452 (M+H$^+$), 305, 192; melting point 71–73° C. (dihydroacetate)

Example 256

H-(D)Chg-Pro-NH-3-(2-MeO-6-Am)-pico a) 2-Methoxy-3-picolyl alcohol.HCl 20.0 g of 2-methoxynicotinic acid (130.59 mmol) were introduced together with 28.7 ml of N-methylmorpholine (261.18 mmol) into THF at −10° C., and 25.4 ml of isobutyl chloroformate (195.89 mmol) in 50 ml of THF were rapidly added dropwise, during which a precipitate separated out.

After stirring at 0° C. for one hour, 16.3 g of sodium borohydride (430.95 mmol) were added in portions and subsequently 250 ml of methanol were slowly added dropwise (vigorous evolution of gas and exothermic reaction). After the precipitated salt had been filtered off with suction, the filtrate was concentrated under reduced pressure in a rotary evaporator, and the residue was taken up in ethyl acetate, washed with water, dilute hydrochloric acid (pH=2), saturated brine (water phases were kept very small), dried over magnesium sulfate and concentrated in a rotary evaporator. The residue was taken up in ether, ethereal hydrochloric acid was added, and the precipitate was filtered off with suction and extracted by stirring with ether. 16.3 g (71%) of 2-methoxy-3-picolyl alcohol hydrochloride were obtained as a white salt.

b) 2-Methoxy-3-picolyl chloride.HCl 51 ml of thionyl chloride (696.67 mmol) were added dropwise to 17 g of 2-methoxy-3-picolyl alcohol.HCl (96.76 mmol) suspended in 60 ml of DCM, the solution was stirred at room temperature for 1 h, the solvent and excess thionyl chloride were removed under reduced pressure, and the residue was codistilled 4 times with methanol under reduced pressure and subsequently extracted by stirring with ether. 15.2 g of is 2-methoxy-3-picolyl chloride hydrochloride (81%) were obtained as a white crystalline salt.

c) 2-Methoxy-3-picolylamine 2HCl 15.1 g of 2-methoxy-3-picolyl chloride hydrochloride (77.76 mmol) were slowly added dropwise to a mixture of 600 ml of 30% strength ammonia solution in water and 250 ml of methanol at 35° C. while continuously passing in gaseous ammonia. After the solution had been stirred at 35° C. for 1 h it was concentrated under reduced pressure in a rotary evaporator, the residue was made alkaline with 20% strength NaOH solution (water phases were kept small) and extracted several times with DCM, and the org. phases were dried over magnesium sulfate and concentrated under reduced pressure in a rotary evaporator. The residue was taken up in ether and, after addition of ethereal hydrochloric acid, filtration with suction and washing of the precipitate with ether, 11.0 g (67%) of 2-methoxy-3-picolylamine.2HCl were obtained as white crystals.

d) Boc-(D)Chg-Pro-NH-3-(2-MeO)-pico

Prepared as for Boc-(D)Chg-Pro-NH-3-(2-Me)-pico (see Example 227) Yield 92%.

e) Boc-(D)Chg-Pro-NH-3-(2-MeO-1-oxo)-pico 4.9 g of Boc-(D)Chg-Pro-NH-3-(2-MeO)-pico (10.32 mmol) were dissolved in 100 ml of DCM, 3.6 g of meta-chloroperbenzoic acid (20.64 mmol) were added and the mixture was stirred at room temperature for several days (only partial conversion according to TLC). The solution was subsequently diluted with DCM, dried over magnesium sulfate and saturated with gaseous ammonia, the precipitate was filtered off and the filtrate was concentrated under reduced pressure. The product mixture was taken up in ether and extracted with 1 M potassium bisulfate solution (pH 2), and the aqueous phase was made alkaline with potassium carbonate, extracted by shaking several times with DCM, dried over magnesium sulfate and concentrated under reduced pressure in a rotary evaporator. 1.6 g of Boc-(D) Chg-Pro-NH-3-(2-MeO)-1-oxo)-pico were obtained as a solid foam. It was possible to recover 3.1 g of precursor from the acidic ether extract and use it again in the N-oxide preparation. A total of 4.2 g of product were obtained by repetition several times.

f) Boc-(D)Chg-Pro-NH-3-(2-MeO-6-CN)-pico 4.2 g of Boc-(D)Chg-Pro-NH-3-(2-MeO-6-CN)-pico (8.56 mmol) were used together with 16 ml of trimethylsilyl cyanide, 5 ml of 1,2-dichlorethane and 10 ml of dimethyl-carbamoyl chloride, immediately heated to 70° C. and stirred at this temperature for 10 min. After concentration under reduced pressure, the product mixture was separated (2 main components, TLC: Rf=0.46 and 0.26, eluent DCM/MeOH=95/5) by column chromatography on silica gel (eluent: DCM with 0.5 increasing to 1.5% MeOH).

The first main fraction contains 1.17 g of Boc-(D)Chg-Pro-NH-3-(2-MeO-6-CN)-pico.

g) Preparation of Boc-(D)Chg-Pro-NH-3-(2-MeO-6-Ham)-pico 1.17 g of Boc-(D)Chg-Pro-NH-3-(2-MeO-6-CN)-pico (2.34 mmol) were stirred together with 0.41 g of hydroxy-lammonium chloride and 2 ml of DIPEA (11.7 mmol) in 10 ml of DCM at room temperature for 4 h and subsequently concentrated under reduced pressure in a rotary evaporator, the residue was taken up in ethyl acetate and extracted several times with dilute hydrochloric acid (pH 4) and the org. phase was dried over magnesium sulfate and concentrated under reduced pressure in a rotary evaporator. The resulting product mixture (2 components, TLC: Rf=0.54 and 0.42, eluent DCM/MeOH=9/1) was separated by column chromatography on silica gel (eluent: DCM with 0.5 increasing to 1.5% MeOH). The first main fraction contained 300 mg of Boc-(D)Chg-Pro-NH-3-(2-MeO-6-Ham)-Pico. $^{13}$C-NMR (d$_6$-DMSO, δ in ppm): 171.16, 170.46, 159.13, 155.69, 148.89, 145.44, 135.84, 120.76, 111.53, 77.80, 59.55, 56.66, 52.84, 46.56, 38.4, 36.32, 28.87, 28.38, 28.17, 27.72, 27.57, 25.37, 25.29, 25.09, 23.65.

h) Boc-(D)Chg-Pro-NH-3-(2-MeO-6-Am)-pico 300 mg of Boc-(D)Chg-Pro-NH-3-(2-MeO-6-Ham)-pico (0.56 mmol) were hydrogenated in 10 ml of ethanol and 2 ml of acetic acid on Pd/C (10%) at 60° C. for 4 h. Removal of the catalyst by filtration and concentration of the reaction solution under reduced pressure resulted in 260 mg of Boc-(D)Chg-Pro-NH-3-(2-MeO-6-Am)-pico crude product which was used without further purification in the following reaction.

i) H-(D)Chg-Pro-NH-3-(2-MeO-6-Am)-pico 260 mg of Boc-(D)Chg-Pro-NH-3-(2-MeO-6-Am)-pico crude product were stirred in 5 ml of DCM and 5 ml of methanol together with 5 ml of ethereal hydrochloric acid at room temperature overnight, the reaction mixture was concentrated under reduced pressure, and the residue was codistilled several times with toluene/methanol and subsequently extracted by stirring with ether. 210 mg of Boc-(D)Chg-Pro-NH-3-(2-MeO-6-Am)-pico.(HCl)$_{1.2}$ were obtained as white crystalline solid substance. Melting point 205–212° C. FAB-MS: (M+H)$^+$=417

We claim:

1. A compound of the formula

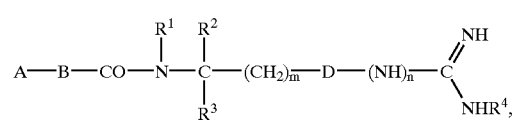

or a salt thereof or a stereoisomer thereof, in which the substituents have the following meanings:

A is
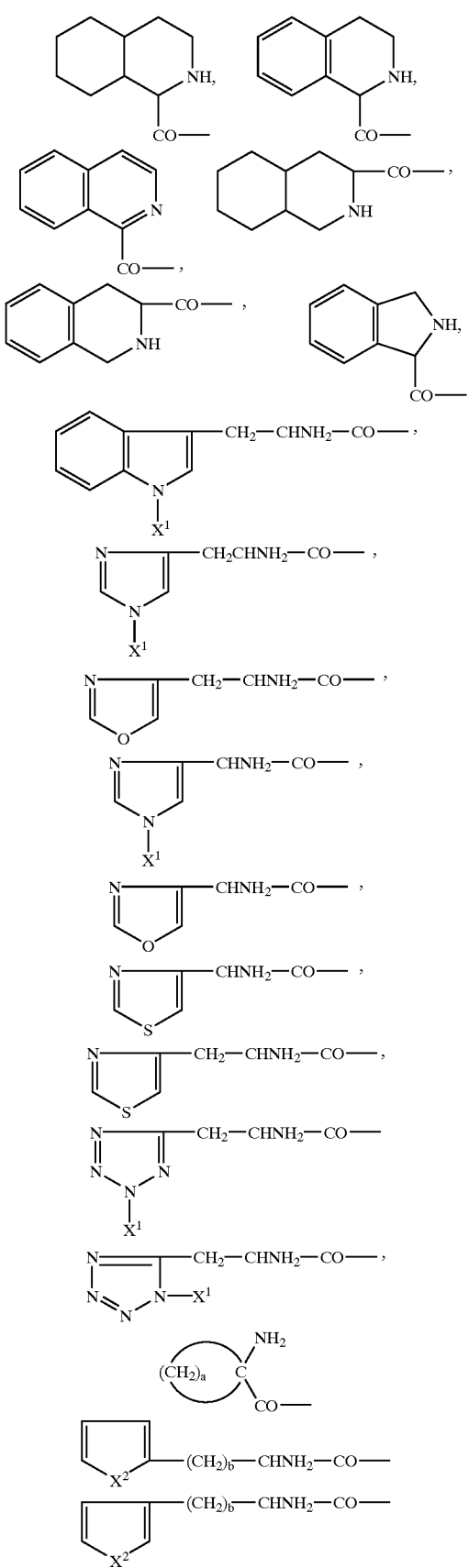
-continued
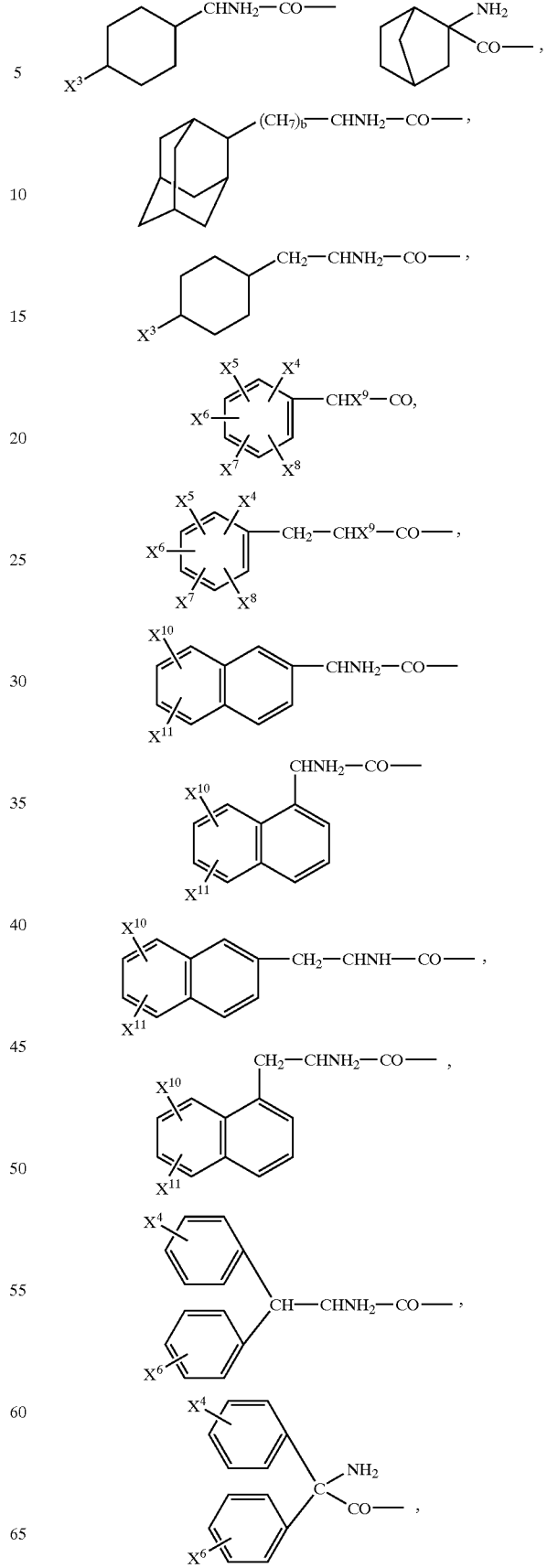

-continued

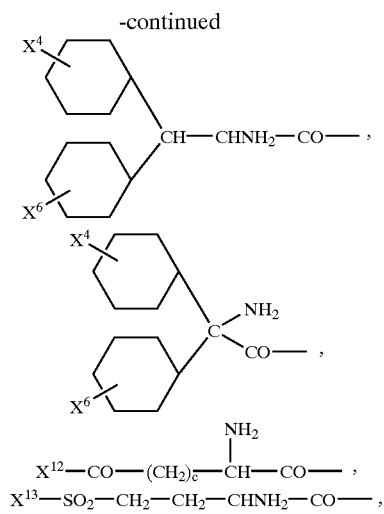

$X^{12}$—CO—$(CH_2)_c$—CH(NH_2)—CO—, $X^{13}$—SO_2—CH_2—CH_2—CHNH_2—CO—,

H_2N—CH_2—CO— or H_2N—CHX$^{13}$—CO—, wherein $X^1$ is H, $C_{1-4}$-alkyl, $C_{1-4}$-alkylphenyl, $C_{1-5}$-acyl or $C_{1-4}$-alkoxycarbonyl;

a is 2–6, and a $CH_2$ group may be replaced by O, S, NH or $NC_{1-4}$-alkyl;

$X^2$ is O, $NX^1$ or S;

b is 0 or 1;

$X^3$ is H, $C_{1-4}$-alkyl, F, Cl, OH or $OCH_3$;

$X^4$ is H, F, Cl, $CF_3$, Br, $C_{1-4}$-alkyl, phenyl, benzyl, OH, $C_{1-4}$-alkoxy, $NO_2$, —COOH or —COOC$_{1-4}$-alkyl;

$X^5$ is H, F, Cl, Br, $C_{1-4}$-alkyl, phenyl, benzyl, OH, $C_{1-4}$-alkoxy, phenyloxy, phenyl-$C_{1-4}$-alkoxy, —COOH or —COOC$_{1-4}$-alkyl;

$X_6$ is H, F, Cl, Br, $C_{1-4}$-alkyl, OH or $C_{1-4}$-alkoxy;

$X^7$ is H, F or Cl;

$X^8$ is H, F or Cl;

$X^9$ is $NH_2$ or OH;

$X^{10}$ and $X^{11}$ are each H, $C_{1-4}$-alkyl, OH or $OCH_3$;

c is 1 or 2;

$X^{12}$ is OH, $C_{1-4}$-alkoxy, phenyl-$C_{1-4}$-alkoxy, $NH_2$, NH—$C_{1-4}$-alkyl or —$NX^{13}X^{14}$;

$X^{13}$ is $C_{1-8}$-alkyl;

$X^{14}$ is $C_{1-4}$-alkyl or, in —$NX^{13}X^{14}$, $X^{13}$ and $X^{14}$ together may be —$(CH_2)_d$—, wherein d is 3, 4, 5, 6, 7, where in all of the above recited A radicals the NH or $NH_2$ group a to the carbonyl group can be mono- or disubstituted by $C_{1-12}$-alkyl, phenyl-$C_{1-4}$-alkylene, $X^{12}OC$—$C_{1-6}$alkylene, $X^{12}OC$—$C_{1-6}$alkylcarbonyl, α- or β-naphthyl-$C_{1-4}$-alkylene, $C_{1-12}$-alkylcarbonyl, phenyl-$C_{1-4}$-alkylcarbonyl, $C_{1-7}$-alkoxycarbonyl, phenyl-$C_{1-5}$-alkoxycarbonyl, -α- or β-naphthyl-$C_{1-14}$-alkylcarbonyl-, $C_{1-6}$-alkylaminocarbonyl or phenyl-$C_{1-4}$-alkylaminocarbonyl, or A is $X^1$—NH—CH_2—CH_2—CO—, $X^1$—NH—CH_2—CH_2—CH_2—CO— or $X^{15}$—$(CH_2)_f$—SO_2—, wherein f is 0, 1, 2, 3, 4 and $X^{15}$ is a phenyl or α- or β-naphthyl group which is unsubstituted or substituted by 1–3 $CH_3$ and/or $CH_3O$ groups, or one of the groups

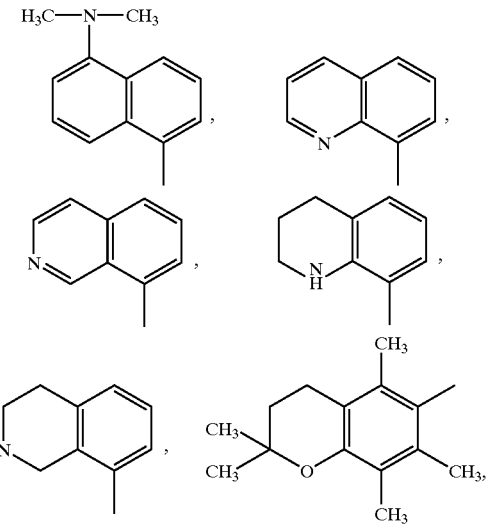

or A is

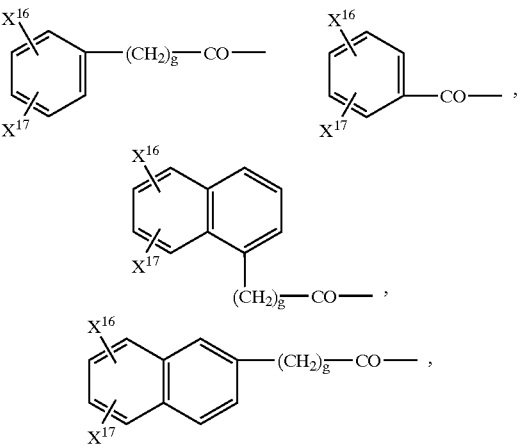

$X^{18}$—O—CO—$C_{1-4}$-alkylene —CO—, $C_1$–$C_{12}$-alkyl-CO—, $C_1$–$C_{10}$-alkyl-NH—CO-phenyl-$C_{1-4}$-alkylene-NH—CO—, α- or β-naphthyl-CO— or $C_{3-7}$-cycloalkyl-CO—, wherein $X^{16}$ is H, F, Cl, Br, $CF_3$, OH, $C_{1-8}$-alkyl or $C_{1-4}$-alkoxy;

$X^{17}$ is H, OH, $C_{1-4}$-alkyl or $C_{1-4}$-alkoxy;

g is 1, 2, 3, 4, 5, 6, 7 or 8; and $X_{18}$ is H or $C_{1-4}$-alkyl,

B is 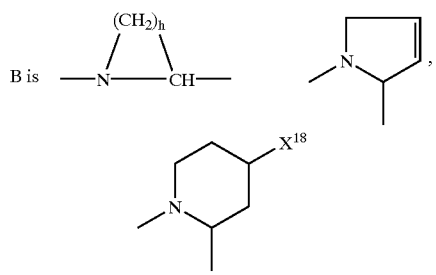

wherein h is 2, 3, or 4, and a $CH_2$ group is replaced by a $NX^1$, SO group or an O or S atom, and $X^{18}$ is H or $C_{1-4}$-alkyl and $R^1$ is H or $C_{1-4}$-alkyl, $R^2$ is H or $C_{1-4}$-alkyl, $R^3$ is H, $C_{1-8}$-alkyl, phenyl, phenyl-$C_{1-4}$-alkylene, $CH_2OH$, —CO—$X^{20}$, —CO—CO—$X^{20}$, wherein $X^{20}$ is H, $C_{1-4}$-alkoxy, $C_{1-4}$-alkyl, phenyl, phenyl-$C_{1-4}$-alkylene, phenyl-$C_{1-4}$-alkoxy, $CF_3$, $C_2F_5$, an N-terminally linked natural amino acid, $CH_2OH$, —$CH_2$—O—$C_{1-4}$-alkyl, —NH—($C_{1-4}$-alkylene)-phenyl or NH—$C_{1-6}$-alkyl, m is 0, 1, 2 or 3, n is 0 or 1, D is phenylene on which $(CH_2)_m$ and $(NH)_n$ are linked in the meta position to one another and which can be substituted in the ortho position to $(CH_2)_m$ by F, Cl, Br, HO—$CH_2$—, OH, $NH_2$, $NO_2$, $C_{1-4}$-alkoxy, $C_{1-6}$-alkyl or $COX^{21}$—O—$(CH_2)_{1-3}$—CO—$X^{21}$ or —$(CH_2)_{1-3}$—CO—$X^{21}$, pyridinylene, pyrimidinylene, pyrazinylene or pyridazinylene, on which $(CH_2)_m$ and $(NH)_n$ are linked in the para or meta position to one another and which can be substituted in the ortho position to $(CH_2)_m$ by F, Cl, Br, HO—$CH_2$—, OH, $NH_2$, $N_2$, $C_{1-4}$-alkoxy, $C_{1-6}$-alkyl or $COX^{21}$, —O—$(CH_2)_{1-3}$—CO—$X^{21}$ or —$(CH_2)_{1-3}$—CO—$X^{21}$, wherein $X^{21}$ is H, $C_{1-4}$-alkyl, $C_{1-4}$-alkoxy, OH, $NH_2$, or NH—$C_{1-4}$-alkyl, $R^4$ is H, —CO—$C_{1-20}$-alkyl, —CO—O—$C_{1-20}$-alkyl, OH or $NH_2$.

* * * * *